United States Patent
Seitz et al.

(10) Patent No.: US 11,203,592 B2
(45) Date of Patent: Dec. 21, 2021

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: Steven P. Seitz, Swarthmore, PA (US); Emily Charlotte Cherney, Newtown, PA (US); Xiao Zhu, Winchester, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/754,175

(22) PCT Filed: Oct. 8, 2018

(86) PCT No.: PCT/US2018/054822
§ 371 (c)(1),
(2) Date: Apr. 7, 2020

(87) PCT Pub. No.: WO2019/074824
PCT Pub. Date: Apr. 18, 2019

(65) Prior Publication Data
US 2021/0221806 A1    Jul. 22, 2021

Related U.S. Application Data

(60) Provisional application No. 62/569,752, filed on Oct. 9, 2017.

(51) Int. Cl.
*C07D 471/04* (2006.01)
*C07D 307/94* (2006.01)
*C07D 405/06* (2006.01)
*C07K 16/28* (2006.01)

(52) U.S. Cl.
CPC .......... *C07D 471/04* (2013.01); *C07D 307/94* (2013.01); *C07D 405/06* (2013.01); *C07K 16/2818* (2013.01)

(58) Field of Classification Search
CPC ... C07D 471/04; C07D 307/94; C07D 405/06
See application file for complete search history.

(56) References Cited

U.S. PATENT DOCUMENTS

| 2005/0261327 A1 | 11/2005 | Bock et al. |
| 2010/0233166 A1 | 9/2010 | Prendergast et al. |
| 2021/0122757 A1* | 4/2021 | Kinzel .............. A61P 35/00 |

FOREIGN PATENT DOCUMENTS

| JP | 2009-173629 A | 8/2009 |
| WO | 99/29310 A2 | 6/1999 |
| WO | 2004/094409 A1 | 11/2004 |
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |
| WO | 2008/132601 A1 | 11/2008 |
| WO | 2009/009116 | 1/2009 |
| WO | 2009/044273 A2 | 4/2009 |
| WO | 2009/073620 A2 | 6/2009 |
| WO | 2009/156652 A1 | 12/2009 |
| WO | 2010/019570 A2 | 2/2010 |
| WO | 2010/077634 A1 | 7/2010 |
| WO | 2011/028683 | 3/2011 |
| WO | 2011/056652 A1 | 5/2011 |
| WO | 2011/070024 A1 | 6/2011 |
| WO | 2011/107553 A1 | 9/2011 |
| WO | 2011/109400 A2 | 9/2011 |
| WO | 2011/131407 A1 | 10/2011 |
| WO | 2011/140249 A2 | 11/2011 |
| WO | 2012/032433 A1 | 3/2012 |
| WO | 2012/142237 A1 | 10/2012 |

(Continued)

OTHER PUBLICATIONS

Luo et al. Cell, 2009, 136, pp. 823-837 (Year: 2009).*
Feder-Mengus et al. European Journal of Cancer, 2008, 44, 2266-2275 (Year: 2008).*
Inaba et al. Gynecologic Oncology 2009, 115, 185-192 (Year: 2009).*
Speeckaert et al. European Journal of Cancer, 2012, 48, 2004-2011 (Year: 2012).*

(Continued)

*Primary Examiner* — Matthew P Coughlin
(74) *Attorney, Agent, or Firm* — BakerHostetler

(57) ABSTRACT

The present invention provides compounds of formula (I): wherein all of the variables are as defined herein. These compounds are inhibitors of indoleamine 2,3-dioxygenase (IDO), which may be used as medicaments for the treatment of proliferative disorders, such as cancer, viral infections and/or autoimmune diseases.

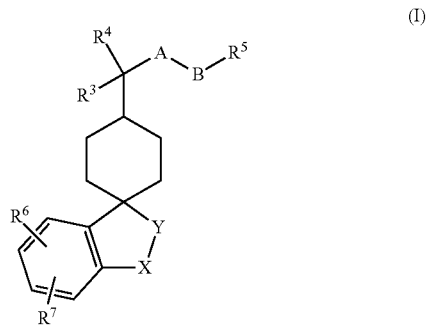

(I)

20 Claims, No Drawings

(56) References Cited

FOREIGN PATENT DOCUMENTS

| WO | 2012/145493 A1 | 10/2012 |
|---|---|---|
| WO | 2013/079174 A1 | 6/2013 |
| WO | 2013/087699 A1 | 6/2013 |
| WO | 2013/119716 A1 | 8/2013 |
| WO | 2013/132044 A1 | 9/2013 |
| WO | 2013/169264 A1 | 11/2013 |
| WO | 2014/008218 A1 | 1/2014 |
| WO | 2014/036357 A1 | 3/2014 |
| WO | 2016/073738 A2 | 5/2016 |
| WO | 2016/073770 A1 | 5/2016 |
| WO | 2016/073774 A2 | 5/2016 |

OTHER PUBLICATIONS

Ball, H.J. et al, ,3-dioxygenase-like protein found in humans and mice [published correction appears in Gene. Oct. 1, 2010;465(1-2):66], Gene. 2007;396(1):203-213.

Brandacher, G. et al., Prognostic value of indoleamine 2,3-dioxygenase expression in colorectal cancer: effect on tumor-infiltrating T cells, Clin Cancer Res. 2006; 12(4):1144-1151.

Bundgaard, H., Chapter 5: "Design and Application of Prodrugs", A Textbook of Drug Design and Development, pp. 113-191, Krogsgaard-Larsen, P. et al., eds., Harwood Academic Publishers (1991.

Bundgaard, H., Prodrugs as a means to improve the delivery of peptide drugs. Adv. Drug Del. Rev. 8:1-38 (1992).

Goldstein et al., J. Biological efficacy of a chimeric antibody to the epidermal growth factor receptor in a human tumor xenograft model. Clin Cancer Res. 1995;1(11):1311-1318.

Kakeya, N et al., Chem. Pharm. Bull., 32:692-698 (1984).

Kohl et al., Inhibition of farnesyltransferase induces regression of mammary and salivary carcinomas in ras transgenic mice, Nat. Med., 1,792-797 (1995).

L.F. Fieser and M. Fieser, Reagentsfor Organic Synthesis, vol. 1, p. 584, Wiley, New York (1967).

Littlejohn, T.K. et al., Expression and Purification of Recombinant Human Indoleamine 2,3-Dioxygenase, Protein Expression Purification, 19:22-29 (Jun. 2000).

Nielsen, N.M et al., Glycolamide esters as biolabile prodrugs of carboxylic acid agents: synthesis, stability, bioconversion, and physicochemical properties. J Pharm Sci. 1988;77(4):285-298.

Sarkar, S.A. et al., Induction of Indoleamine 2,3-Dioxygenase by Interferon-y in Human Islets, Diabetes, 56:72-74 (2007).

Sausville, Cyclin-Dependent Kinase Modulators Studied at the NCI: Pre-Clinical and Clinical Studies, Curr. Med. Chem. Anti-Canc. Agents, 3:47-56 (2003).

Scheller et al., Paclitaxel Balloon Coating, a Novel Method for Prevention and Therapy of Restenosis, Circulation, 110:810-814 (2004).

Sekulic et al, A Direct Linkage Between the Phosphoinositide 3-Kinase-AKT Signaling Pathway and the Mammalian Target of Rapamycin in Mitogen-stimulated and Transformed Cells, Cancer Res., 60:3504-3513 (Jul. 2000).

Serafini P, et al., Myeloid suppressor cells in cancer: Recruitment, phenotype, properties, and mechanisms of immune suppression, Seminars in Cancer Biology, 16(I):53-65 (Feb. 2006).

Vlahos et al., J. Biol. Chem., 269:5241-5248 (1994.

Widder, K. et al., eds., Methods in Enzymology, 112:309-396, Academic Press (1985).

\* cited by examiner

INHIBITORS OF INDOLEAMINE 2,3-DIOXYGENASE AND METHODS OF THEIR USE

CROSS-REFERENCE TO RELATED APPLICATIONS

This application is the National Stage Application of International Patent Application No. PCT/US2018/054822 filed Oct. 8, 2018, which claims the priority benefit of U.S. Provisional Application No. 62/569,752, filed Oct. 9, 2017; the contents of which are herein incorporated by reference in their entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDO) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini P, et al., *Semin. Cancer Biol.*, 16(1):53-65 (February 2006) and Ball, H. J. et al., Gene, 396(1):203-213 (July 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant tumor metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in, for example, WO 2004/094409, WO2016/073770, WO2016/073738, and WO2016/073774.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula (I):

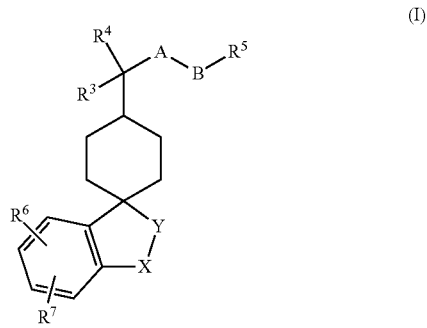

(I)

wherein all of the variables are as defined herein below.

Also within the scope of the invention are pharmaceutically acceptable salts, stereoisomers, tautomers, and solvates of the compounds of formula (I).

The invention is also directed to pharmaceutical compositions comprising one or more compounds of the invention. The invention is also directed to methods of treating cancer using one or more compounds of the invention.

The invention also provides processes and intermediates for making the compounds of formula (I) or pharmaceutically acceptable salts, stereoisomers, tautomers, and solvates thereof.

The compounds of the invention may be used in therapy.

The compounds of the invention may be used for the manufacture of a medicament for the treatment of cancer.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

Compounds of the Invention

In a first aspect, the present invention provides, inter alia, a compound of formula

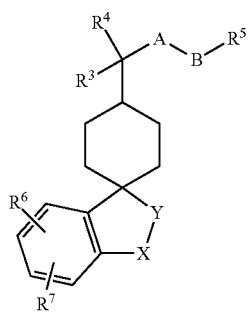

(I)

wherein:

-A-B— is a bond, —NH—CO— or —CO—NH—;

—X—Y— is —O—$CR^1R^2$— or —$CR^1R^2$—;

$R^1$ and $R^2$ are independently H or $C_1$-$C_6$ alkyl optionally substituted with one, two, or three substituents that are independently F, OH or CN;

$R^3$ and $R^4$ are independently H or $C_1$-$C_6$ alkyl optionally substituted with one, two, or three substituents that are independently F, OH or CN;

$R^5$ is $C_1$-$C_6$ alk-O—$C_1$-$C_6$ alkyl;

aryl optionally substituted with one, two, or three substituents that are independently selected from: halo, CN, $C_1$-$C_6$ alkyl, —$OC_1$-$C_6$ alkyl, and 5- to 6-membered heteroaryl optionally substituted with $C_1$-$C_6$ alkyl;

$C_3$-$C_{10}$ cycloalkyl optionally substituted with one, two, or three substituents independently selected from: halo, CN, $C_1$-$C_6$ alkyl, —$OC_1$-$C_6$ alkyl, and 5- to 6-membered heteroaryl optionally substituted with $C_1$-$C_6$ alkyl;

5- to 6-membered cycloheteroalkyl optionally substituted with one, two, or three substituents independently selected from: halo, CN, $C_1$-$C_6$ alkyl, —$OC_1$-$C_6$ alkyl, and 5- to 6-membered heteroaryl optionally substituted with $C_1$-$C_6$ alkyl; or 5- to 10-membered heteroaryl optionally substituted with one, two, or three substituents that are independently selected from: halo, CN, $C_1$-$C_6$ alkyl, —$OC_1$-$C_6$ alkyl, and 5- to 6-membered heteroaryl optionally substituted with $C_1$-$C_6$ alkyl; and $R^6$ and $R^7$ are independently H, halo, $C_1$-$C_6$ alkyl, —$OC_1$-$C_6$ alkyl, or $C_1$-$C_6$ haloalkyl;

or a pharmaceutically acceptable salt, a stereoisomer, a tautomer, or a solvate thereof.

In a second aspect, the present invention provides a compound of formula (I), within the scope of the first aspect, wherein:

$R^1$ and $R^2$ are independently H or $C_1$-$C_4$ alkyl optionally substituted with one OH;

$R^3$ and $R^4$ are independently H or $C_1$-$C_4$ alkyl;

$R^5$ is phenyl optionally substituted with one, two, or three substituents that are independently selected from: halo, CN, $C_1$-$C_6$ alkyl, and —$OC_1$-$C_6$ alkyl;

$C_6$-$C_{10}$ cycloalkyl optionally substituted with one, two, or three substituents independently selected from: halo, CN, $C_1$-$C_6$ alkyl, and —$OC_1$-$C_6$ alkyl; or 5- to 10-membered heteroaryl optionally substituted with one, two, or three substituents that are independently selected from: halo, CN, $C_1$-$C_6$ alkyl, and —$OC_1$-$C_6$ alkyl; and $R^6$ and $R^7$ are independently H, F, Cl, $CH_3$, $CF_3$, —$OCH_3$, or —$OCF_3$.

In a third aspect, the present invention provides a compound of formula (I), within the scope of the first or second aspect, wherein:

$R^5$ is selected from: phenyl, cyclohexyl, bicyclo[2.2.2]octanyl, adamantanyl, and 9- to 10 membered heteroaryl; wherein each moiety is optionally substituted with one or two substituents that independently selected from: halo, CN, $C_1$-$C_4$ alkyl, and —$OC_1$-$C_4$ alkyl.

In a fourth aspect, the present invention provides a compound of formula (I), within the scope of the first to third aspects, wherein:

—X—Y— is —O—$CH_2$—, —O—$CH(CH_2OH)$—, or —$CH_2$—O—;

$R^3$ is H or $CH_3$;

$R^4$ is H;

$R^5$ is selected from:

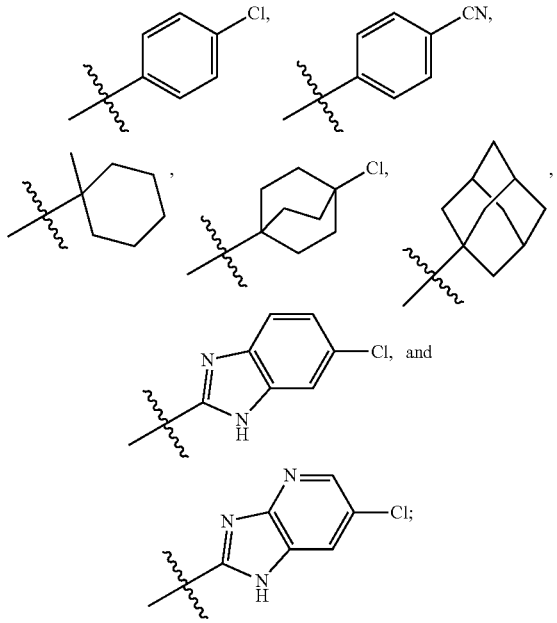

$R^6$ is H or $CH_3$; and $R^7$ is H.

In a fifth aspect, the present invention provides a compound of formula (I), within the scope of the first to fourth aspects, wherein -A-B— is a bond In a sixth aspect, the present invention provides a compound of formula (I), within the scope of the first to fourth aspects, wherein -A-B— is —NH—CO—.
In a seventh aspect, the present invention provides a compound of formula (I), within the scope of the first to fourth aspects, wherein -A-B— is —CO—NH—.
In an eighth aspect, the compound of the invention is selected from:
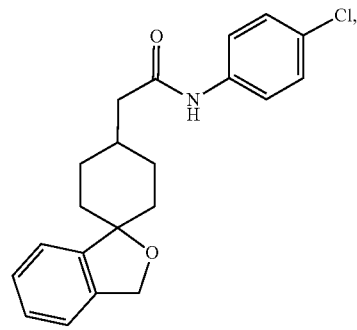
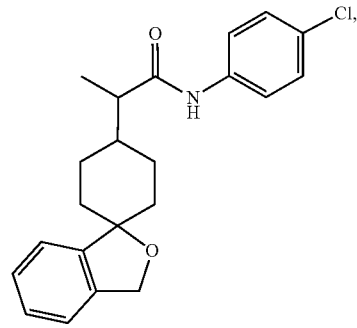
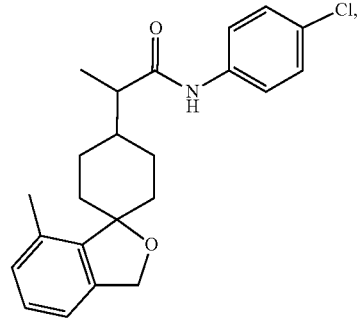
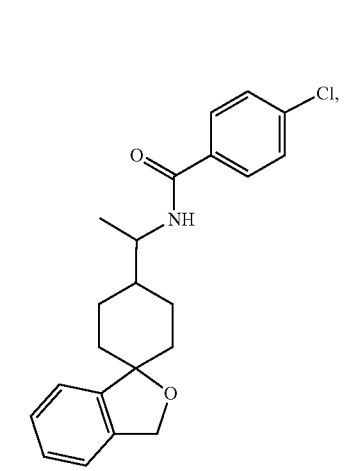
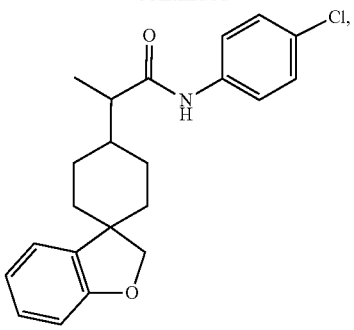
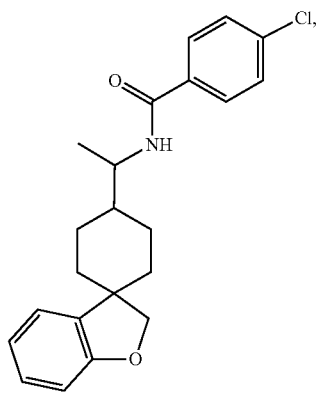
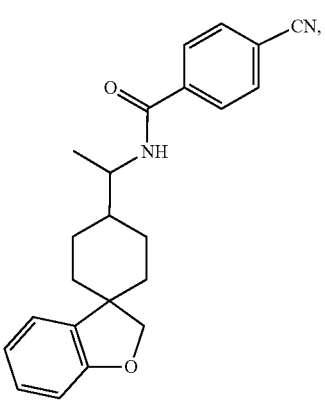
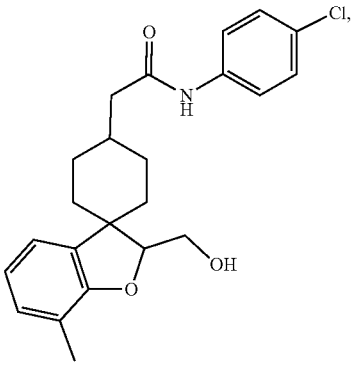

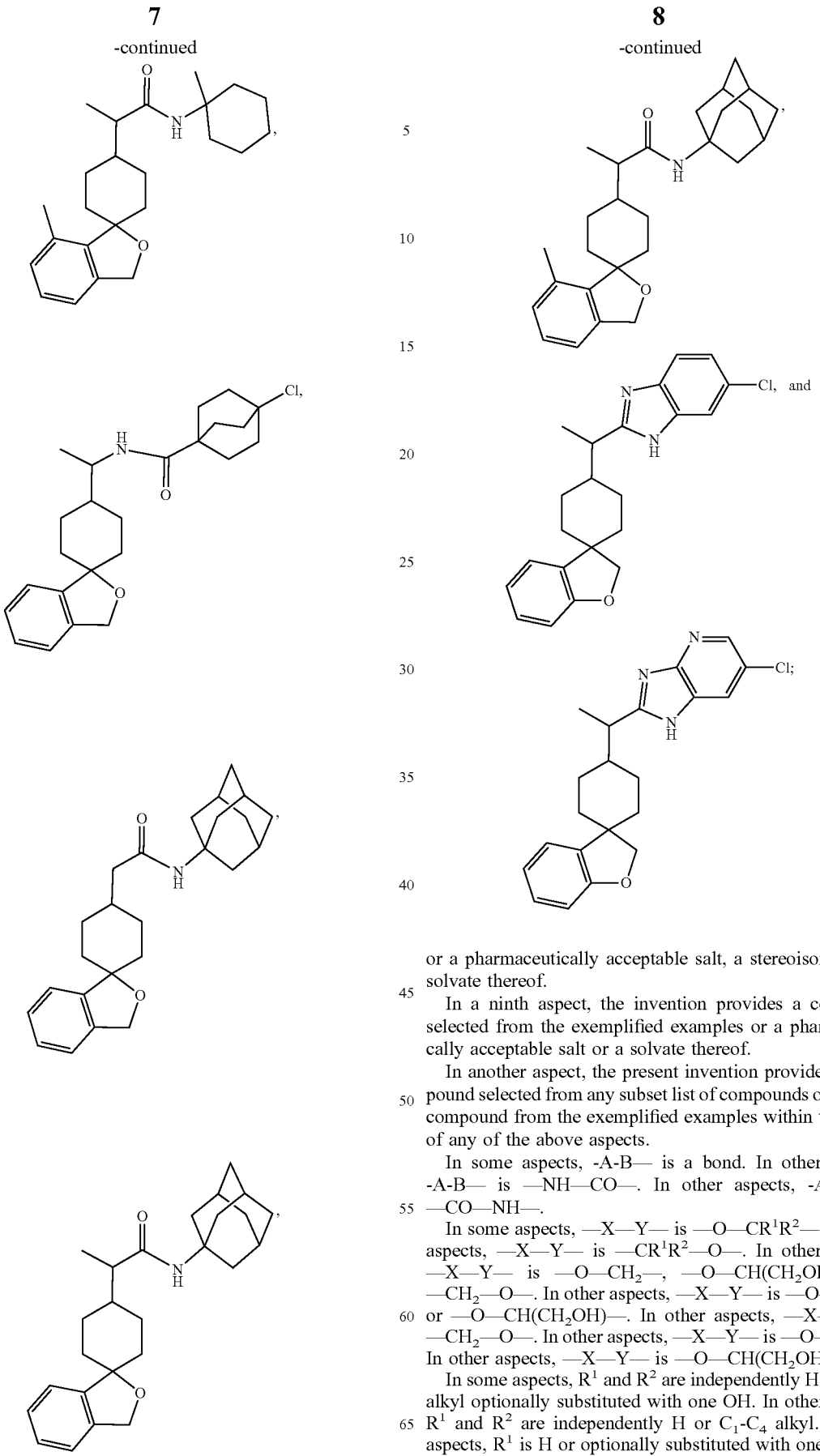

or a pharmaceutically acceptable salt, a stereoisomer, or a solvate thereof.

In a ninth aspect, the invention provides a compound selected from the exemplified examples or a pharmaceutically acceptable salt or a solvate thereof.

In another aspect, the present invention provides a compound selected from any subset list of compounds or a single compound from the exemplified examples within the scope of any of the above aspects.

In some aspects, -A-B— is a bond. In other aspects, -A-B— is —NH—CO—. In other aspects, -A-B— is —CO—NH—.

In some aspects, —X—Y— is —O—CR$^1$R$^2$—. In other aspects, —X—Y— is —CR$^1$R$^2$—O—. In other aspects, —X—Y— is —O—CH$_2$—, —O—CH(CH$_2$OH)—, or —CH$_2$—O—. In other aspects, —X—Y— is —O—CH$_2$— or —O—CH(CH$_2$OH)—. In other aspects, —X—Y— is —CH$_2$—O—. In other aspects, —X—Y— is —O—CH$_2$—. In other aspects, —X—Y— is —O—CH(CH$_2$OH)—.

In some aspects, R$^1$ and R$^2$ are independently H or C$_1$-C$_4$ alkyl optionally substituted with one OH. In other aspects, R$^1$ and R$^2$ are independently H or C$_1$-C$_4$ alkyl. In other aspects, R$^1$ is H or optionally substituted with one OH and R is H. In other aspects, R$^1$ is H or C$_1$-C$_4$ alkyl and R$^2$ is H.

In some aspects, $R^3$ and $R^4$ are independently H or $C_1$-$C_4$ alkyl. In other aspects, $R^3$ is H or $C_1$-$C_4$ alkyl and $R^4$ is H. In other aspects, $R^3$ is H or $CH_3$ and $R^4$ is H.

In some aspects, $R^5$ is aryl optionally substituted with one, two, or three substituents that are independently selected from: halo, CN, $C_1$-$C_6$ alkyl, —$OC_1$-$C_6$ alkyl, and 5- to 6-membered heteroaryl optionally substituted with $C_1$-$C_6$ alkyl; $C_3$-$C_{10}$ cycloalkyl optionally substituted with one, two, or three substituents independently selected from: halo, CN, $C_1$-$C_6$ alkyl, —$OC_1$-$C_6$ alkyl, and 5- to 6-membered heteroaryl optionally substituted with $C_1$-$C_6$ alkyl; or 5- to 10-membered heteroaryl optionally substituted with one, two, or three substituents that are independently selected from: halo, CN, $C_1$-$C_6$ alkyl, —$OC_1$-$C_6$ alkyl, and 5- to 6-membered heteroaryl optionally substituted with $C_1$-$C_6$ alkyl; In other aspects, $R^5$ is phenyl optionally substituted with one, two, or three substituents that are independently selected from: halo, CN, $C_1$-$C_6$ alkyl, and —$OC_1$-$C_6$ alkyl; $C_6$-$C_{10}$ cycloalkyl optionally substituted with one, two, or three substituents independently selected from: halo, CN, $C_1$-$C_6$ alkyl, and —$OC_1$-$C_6$ alkyl; or 5- to 10-membered heteroaryl optionally substituted with one, two, or three substituents that are independently selected from: halo, CN, $C_1$-$C_6$ alkyl, and —$OC_1$-$C_6$ alkyl. In other aspects, $R^5$ is phenyl optionally substituted with one, two, or three substituents that are independently selected from: halo, CN, $C_1$-$C_6$ alkyl, and —$OC_1$-$C_6$ alkyl. In other aspects, $R^5$ is $C_6$-$C_{10}$ cycloalkyl optionally substituted with one, two, or three substituents independently selected from: halo, CN, $C_1$-$C_6$ alkyl, and —$OC_1$-$C_6$ alkyl. In other aspects, $R^5$ is 5- to 10-membered heteroaryl optionally substituted with one, two, or three substituents that are independently selected from: halo, CN, $C_1$-$C_6$ alkyl, and —$OC_1$-$C_6$ alkyl. In other aspects, $R^5$ is selected from: phenyl, cyclohexyl, bicyclo[2.2.2]octanyl, adamantanyl, and 9- to 10 membered heteroaryl; wherein each moiety is optionally substituted with one or two substituents that independently selected from: halo, CN, $C_1$-$C_4$ alkyl, and —$OC_1$-$C_4$ alkyl. In other aspects, $R^5$ is phenyl optionally substituted with one or two substituents that independently selected from: halo, CN, $C_1$-$C_4$ alkyl, and —$OC_1$-$C_4$ alkyl. In other aspects, $R^5$ is cyclohexyl, bicyclo[2.2.2]octanyl and adamantanyl; wherein each moiety is optionally substituted with one or two substituents that independently selected from: halo, CN, $C_1$-$C_4$ alkyl, and —$OC_1$-$C_4$ alkyl. In other aspects, $R^5$ is 9- to 10 membered heteroaryl; wherein each moiety is optionally substituted with one or two substituents that independently selected from: halo, CN, $C_1$-$C_4$ alkyl, and —$OC_1$-$C_4$ alkyl. In other aspects, $R^5$ is benzimidazolyl or imidazopyridinyl; wherein each moiety is optionally substituted with one or two substituents that independently selected from: halo, CN, $C_1$-$C_4$ alkyl, and —$OC_1$-$C_4$ alkyl. In other aspects, $R^5$ is,

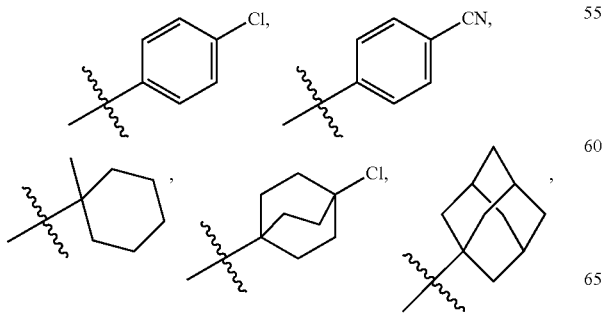

-continued

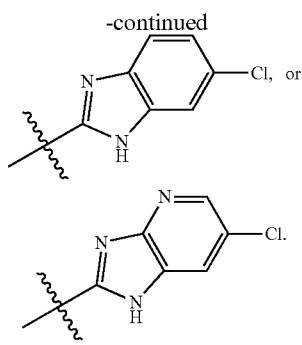

In other aspects, $R^5$ is

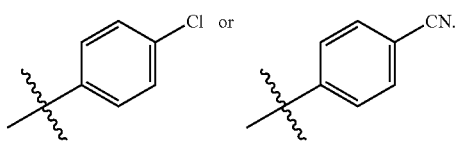 [SMILES: *c1ccc(Cl)cc1 ; *c1ccc(C#N)cc1]

In other aspects, $R^5$ is

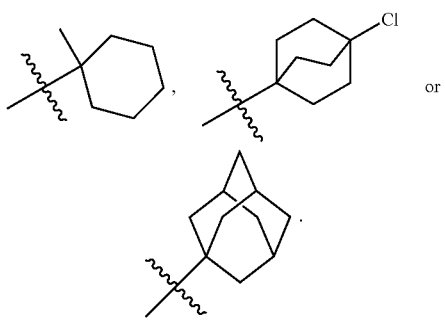

In other aspects, $R^5$ is

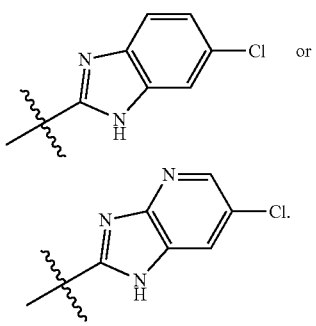

In some aspects, $R^6$ is H, halo, $C_1$-$C_6$ alkyl, —$OC_1$-$C_6$ alkyl, or $C_1$-$C_6$ haloalkyl, and $R^1$ is H. In other aspects, $R^6$ and $R^7$ are independently H, F, Cl, $CH_3$, $CF_3$, —$OCH_3$, or —$OCF_3$. In other aspects, $R^6$ is H, F, Cl, $CH_3$, $CF_3$, —$OCH_3$, or —$OCF_3$, and $R^7$ is H. In other aspects, $R^6$ and $R^7$ are independently H or $CH_3$. In other aspects, $R^6$ is H or $CH_3$; and $R^7$ is H.

In another embodiment, the compounds of the invention have human IDO $IC_{50}$ values >50 nM but ≤1 µM. In another embodiment, the compounds of the invention have human IDO IC$_{50}$ values ≤50 nM. In another embodiment, the compounds of the invention have human IDO IC$_{50}$ values <5 nM.

Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another embodiment, the additional therapeutic agent(s) are YERVOY, OPDIVO, or KEYTRUDA, or a combination thereof.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as farnesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-01 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J Biol. Chem., 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation,* 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emtricitabine [(−)-FTC]; beta-L-FD4 (also called beta-L-D4C and named beta-L-2′,3′-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of the present invention is administered with one or more immuno-oncology agents. The immuno-oncology agents used herein, also known as cancer immunotherapies, are effective to enhance, stimulate, and/or upregulate immune responses in a subject.

In one aspect, the Compound of the present invention is sequentially administered prior to administration of the immuno-oncology agent. In another aspect, the Compound of the present invention is administered concurrently with the immunology-oncology agent. In yet another aspect, the Compound of the present invention is sequentially administered after administration of the immuno-oncology agent.

In another aspect, the Compound of the present invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the Compound of the present invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of the present invention for the treatment of cancer include antagonists of inhibitory receptors on NK cells or agonists of activating receptors on NK cells. For example, the Compound of the present invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of the present invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MED14736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of the present invention, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol ⊥ is used in formulas and tables to show the bond that is the point of attachment of the moiety or substituent to the core/nucleus of the structure.

Additionally, for purposes of clarity, where a substituent has a dash (—) that is not between two letters or symbols; this is used to indicate a point of attachment for a substituent. For example, —OCH$_3$ is attached through the oxygen atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). "C$_1$-C$_6$ alkylene" denotes alkylene having 1 to 6 carbon atoms. Example alkylene groups include, but are not limited to, methylene (—CH$_2$—), ethylene (—CH$_2$CH$_2$—), and the like.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to hydrocarbon rings having the indicated number of ring atoms (e.g., C$_{3-10}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, adamantane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A cycloheteroalkyl group can be attached to the remainder of the molecule through a ring carbon or a heteroatom.

As used herein, "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, 1,2,4-thiadiazolyl, isothiazolyl, purinyl, carbazolyl, indazolyl, quinolyl, isoquinolyl, benzimidazolyl, imidazopyridinyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

As referred to herein, the term "substituted" means that at least one hydrogen atom is replaced with a non-hydrogen group, provided that normal valencies are maintained and that the substitution results in a stable compound.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012). The disclosure of which is hereby incorporated by reference.

In addition, compounds of the present invention may have prodrug forms. Any compound that will be converted in vivo to provide the bioactive agent (i.e., a compound of formula (I)) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);

c) Bundgaard, H., *Adv. Drug Deliv. Rev.*, 8:1-38 (1992);

d) Nielsen, N. M. et al., *J Pharm. Sci.*, 77:285 (1988);

e) Kakeya, N. et al., *Chem. Pharm. Bull.*, 32:692 (1984); and f) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of the present invention include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared in a number of ways known to one skilled in the art of organic synthesis. The compounds of the present invention may be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The compounds of the present invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The compounds of formula (I) may be prepared by the exemplary processes described in the following schemes and working examples, as well as relevant published literature procedures that are used by one skilled in the art. Exemplary reagents and procedures for these reactions appear hereinafter and in the working examples. Protection and de-protection in the processes below may be carried out by procedures generally known in the art (see, for example, Greene, T. W. et al., *Protecting Groups in Organic Synthesis*, 3rd Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry Reactions, Mechanisms, and Structure*, Fifth Edition, Wiley-Interscience, New York (2001); Katritzky, A. R. et al., eds., *Comprehensive Organic Functional Groups Transformations*, 1st Edition, Elsevier Science Inc., Tarrytown, N.Y. (1995); Larock, R. C., *Comprehensive Organic Transformations*, VCH Publishers, Inc., New York, N.Y. (1989), and references therein.

In some embodiments, synthesis of compounds of this invention is illustrated in Schemes 1 to 4.

As shown in Scheme 1, treatment of the commercially available monoketal of cyclohexan-1,4-dione (i) with an organometallic derivative formed from an optionally substituted 2-halobenzyl alcohol (ii) provides the diol (iii). The organometallic (ii) may be conveniently prepared from a 2-bromobenzyl alcohol by halogen-metal exchange with n-butyllithium (M=Li). One trained in the art could readily envisage the use of other halogens or stannane derivatives to prepare (ii). In addition, directed orthometallation using the alcohol as a directing group could be anticipated to be a useful way to prepare intermediates of this type. Formation of the five membered ring could be accomplished by treatment with TFA or another strong acid to give the cyclized compound (iv).

Scheme 1
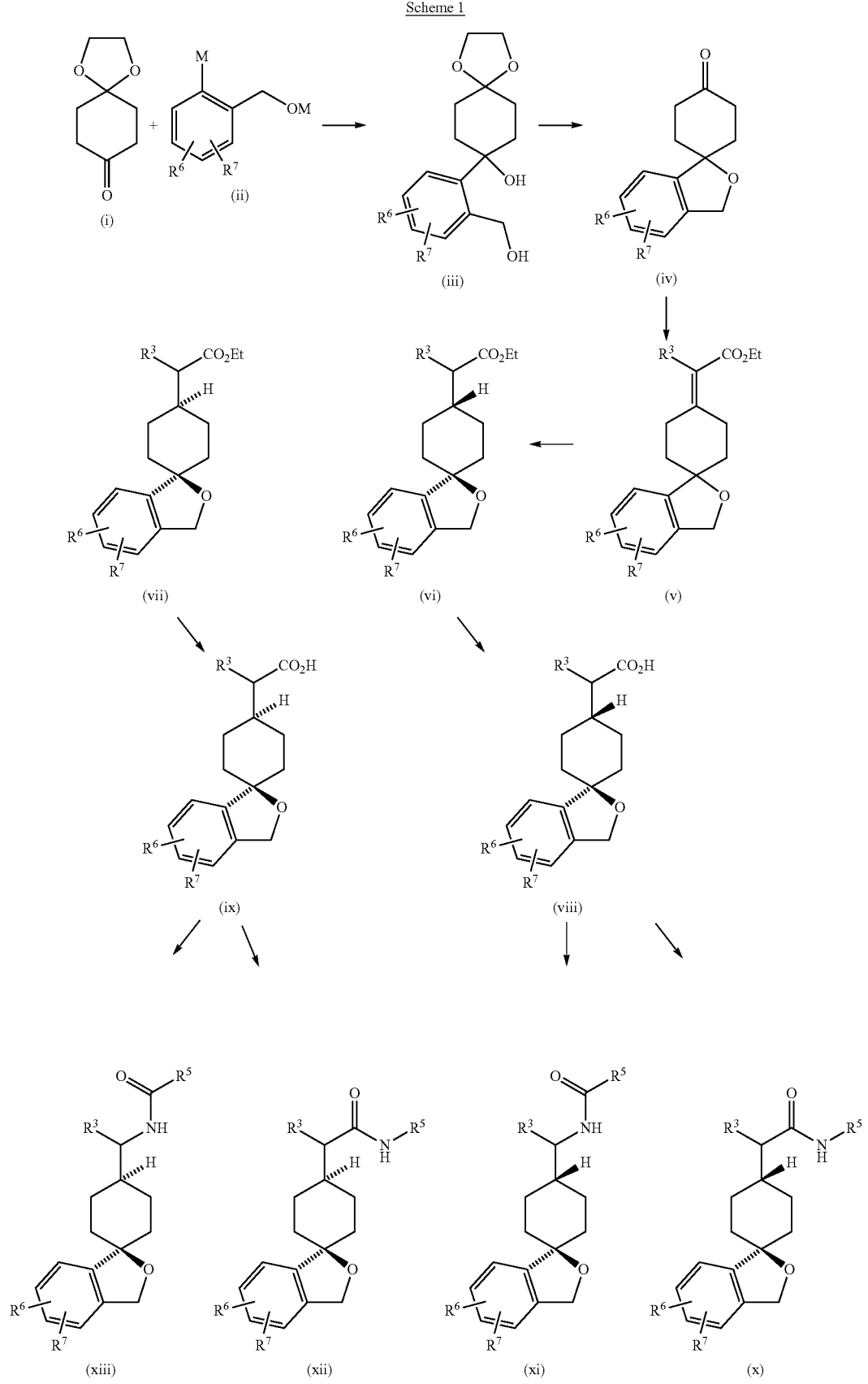

Removal of the ketal protecting group frequently occurs under cyclization conditions. The ketone (iv) can be olefinated under Wadsworth-Horner-Emmons conditions (anion derived from a phosphonoacetate derivative deprotonated with a base such as sodium hexamethyldisilazide) to give the enoate (v). The reduction of the alkene could be accomplished via hydrogenation in the presence of a noble metal catalyst such as Pd, Pt or Rh. The reduction often generates a mixture of cis and trans-isomers which are conveniently separated at this point. The separated isomers (vi) and (vii) could be converted to the corresponding acid with exposure to aqueous base such as lithium, sodium or potassium hydroxide.

The carboxylic acids (viii) and (ix) can be converted into two aspects of this invention. Exposure of the acids to an amine or aniline in the presence of a coupling agent such as BOP, HATU, or PyBOP gives the amides (x) and (xii). Alternatively the carboxylic acid can be subjected to Curtius rearrangement conditions (e.g. DPPA, triethylamine, elevated temperature) to give an isocyanate which can be hydrolyzed to give an amine. This intermediate may be acylated by a variety of methods to give the compounds like (xi) and (xiii).

Compounds like (x), (xi), (xii) and (xiii) in which $R^3$ and $R^4$ (or $R^3$ is not H) are nonequivalent are chiral and exist as a pair of enantiomers. The pure enantiomers may be obtained by chiral chromatography or other methods known to those skilled in the art.

The synthesis of compounds of another aspect of this invention is shown in Scheme 2. Diels-Alder reaction of the diene (2-i) with an acrylate ester gave the cyclohexene derivative (2-iii). Exposure of (2-iii) to ethylene glycol in the presence of acid generates the enoate (2-iv) in which the ketone is protected as a ketal. Reduction of the ester to the allylic alcohol (2-v) can be accomplished with hydrides such as DIBAL, LAH or other similar reagents. The allylic alcohol (2-v) can participate in the Mitsunobu reaction with optionally substituted 2-bromophenols to give the ether (2-vi). This compound is a good substrate for radical cyclization and may be converted to the spirocycle (2-vii) upon treatment with tri-n-butyltin hydride and AIBN at elevated temperature. Acid hydrolysis of (2-vii) gives the ketone (2-ix). This compound is analogous to intermediate (2-iv) in Scheme 1 and may be processed in a similar fashion to give (2-xiii), (2-xiv), (2-xv) and (2-xvi) of this invention.

Scheme 2

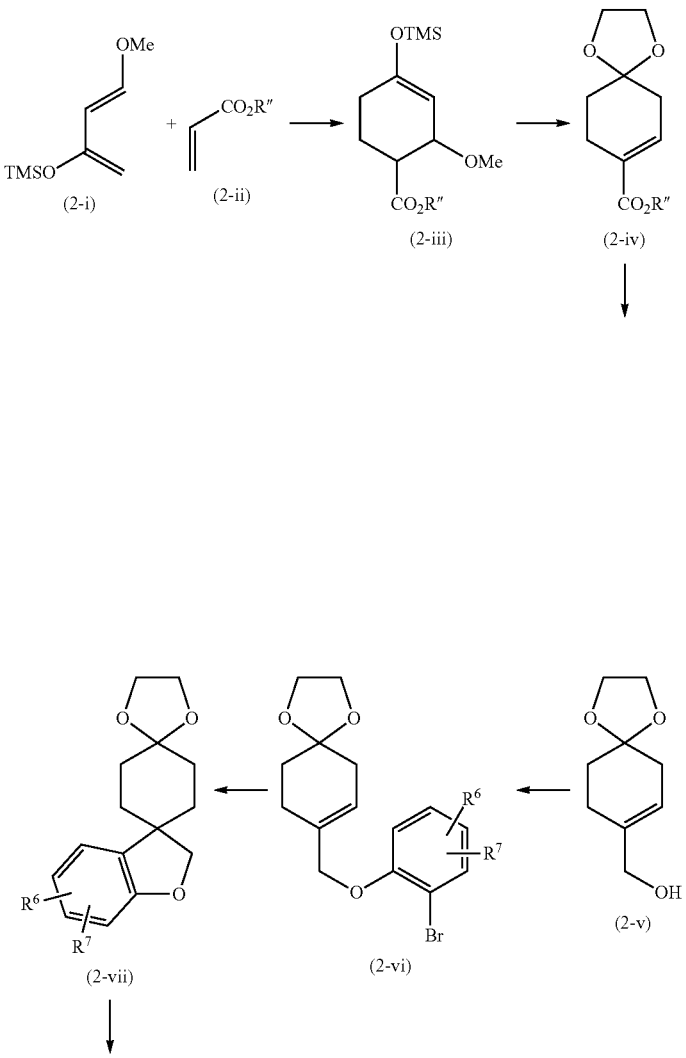

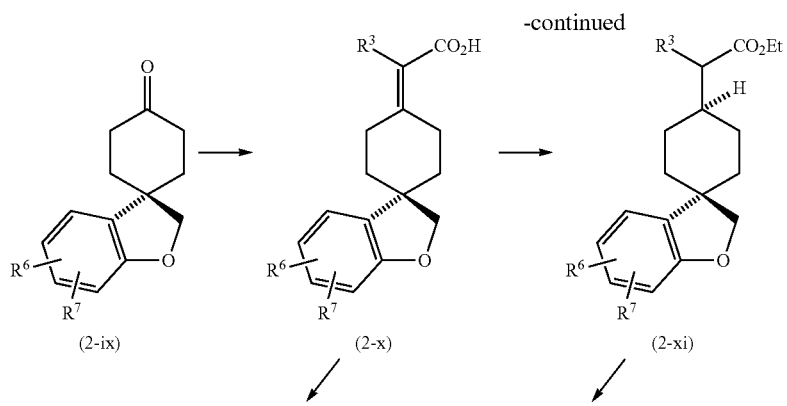

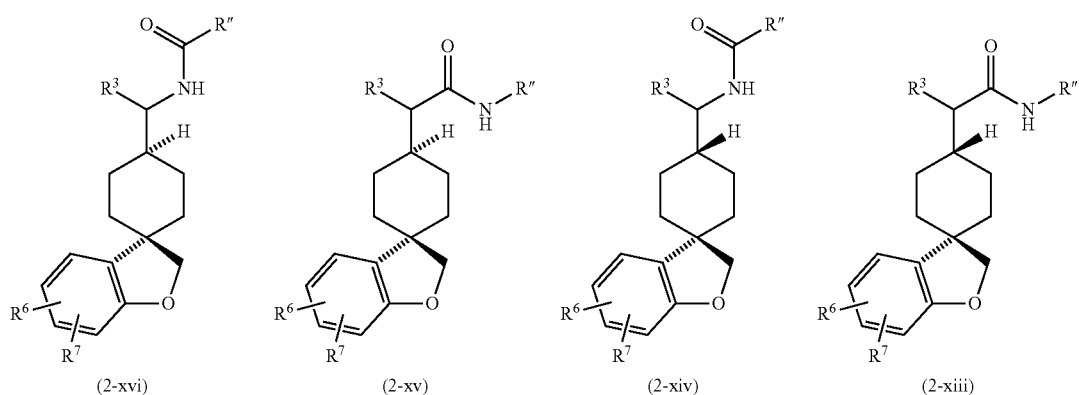

The synthesis of another aspect of this invention is shown in Scheme 3. Compounds of this type feature a substituent on the five membered ring of the spirocycle. The monoketal of cyclohexan-1,4-dione (i) can undergo condensation with aryloxyacetates (3-ii) under basic conditions. Dehydration of the primary condensation product could be accomplished with phosphorus oxychloride to give (3-iv). Compound (3-iv) is a good substrate for radical cyclization and readily cyclizes under appropriate conditions (tri-n-butyltin hydride and AIBN at elevated temperature) to give the spirocycle (3-v). Reduction of the ester and acidic removal of the ketal protecting group then provided (3-vi). This compound is analogous to intermediate (iv) in Scheme 1 and may be processed in a similar fashion to give (3-ix), (3-x), (3-xi) and (3-xii) in Scheme 3 of this invention.

The examples of this invention shown in Schemes 1-3 contain amide bonds; however, it is well known in the art that amides may frequently be replaced with a variety of other groups, especially appropriate heterocycles. This type of replacement may also be used in this invention. An example of this transformation is shown in Scheme 4 where the carboxylic acids (4-i) and (4-ii) (preparation shown previously) may be converted in a three step sequence (formation of acid chloride with thionyl chloride, reaction with a optionally substituted 1,2-diaminobenzene, and cyclization with phosphorus oxychloride) to the target compounds with $R^5$ being a bicyclic heteroaryl (4-iii) and (4-iv) (e.g., $R^5$ is optionally substituted benzimidazole).

Scheme 3
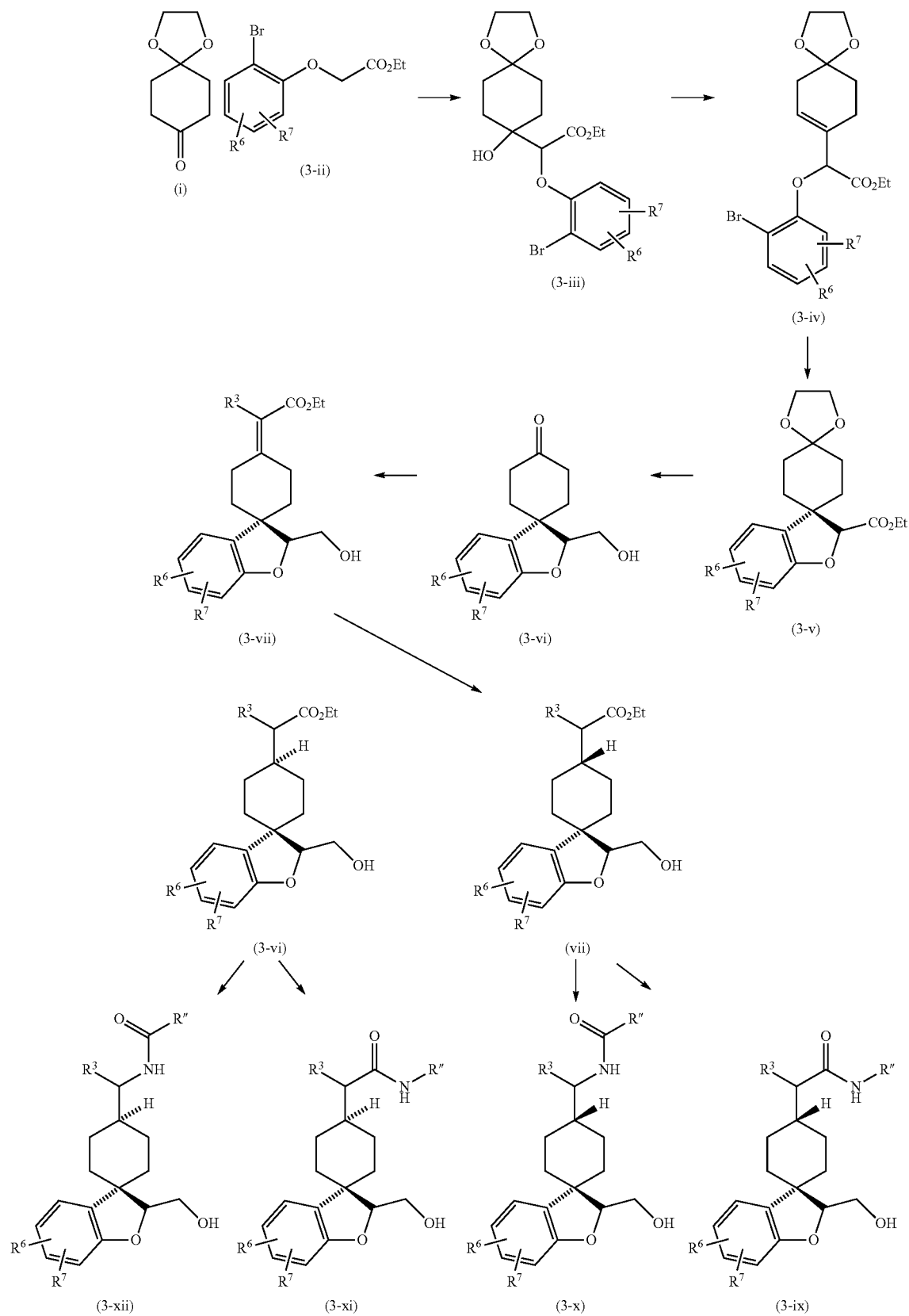

Scheme 4

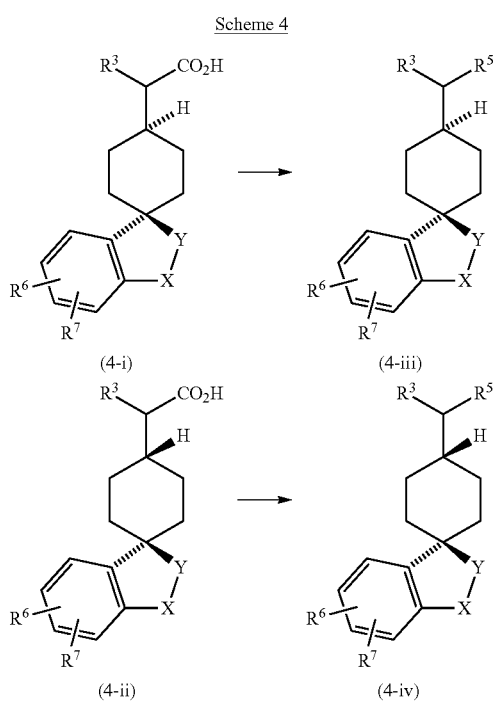

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: 1×=once; 2×=twice; 3×=thrice; rt or RT room temperature; $T_r$=retention time; wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; BW=body weight; U=unit; ns=not statistically significant; PBS=phosphate-buffered saline; IHC=immunohistochemistry; DMEM=Dulbecco's Modification of Eagle's Medium; LG=leaving group; conc.=concentrate or concentrated; aq=aqueous; sat or sat'd=saturated; MW=molecular weight; mp=melting point; MS or Mass Spec=mass spectrometry; ESI=electrospray ionization mass spectroscopy; HR=high resolution; HRMS=high resolution mass spectrometry; LCMS liquid chromatography mass spectrometry; HPLC=high performance liquid chromatography; RP HPLC=reverse phase HPLC; SFC=Supercritical Fluid Chromatography; TLC or tlc=thin layer chromatography; NMR=nuclear magnetic resonance spectroscopy; "$^1$H" for proton, "δ" for delta, "s" for singlet, "d" for doublet, "t" for triplet, "q" for quartet, "m" for multiplet, "br" for broad, "Hz" for hertz; and "α", "β", "R", "S", "E", and "Z" are stereochemical designations familiar to one skilled in the art.
Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
BOP (Benzotriazol-1-yloxy)tris(dimethylamino)phosphonium hexafluorophosphate
$CDCl_3$ deutero-chloroform
$CHCl_3$ chloroform
cDNA complimentary DNA
DMF dimethyl formamide
DMSO dimethyl sulfoxide
DIAD Diisopropyl azodicarboxylate
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
HCl hydrochloric acid
$H_2SO_4$ sulfuric acid
Hunig's base diisopropylethylamine
$K_2CO_3$ potassium carbonate
mCPBA or m-CPBA meta-chloroperbenzoic acid
Pd/C palladium on carbon
PS polystyrene
$SiO_2$ silica oxide
$SnCl_2$ tin (II) chloride
TEA triethylamine
TFA trifluoroacetic acid
TFAA trifluoroacetic anhydride
THF tetrahydrofuran
$TMSCHN_2$ trimethylsilyldiazomethane
KOAc potassium acetate
LHMDS Lithium hexamethyldisilazide
$MgSO_4$ magnesium sulfate
NMP N-Methylpyrrolidone
MsOH or MSA methylsulfonic acid
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia NH$_4$Cl ammonium chloride
NH$_4$OH ammonium hydroxide
HPLC/MS and Preparatory/Analytical HPLC Methods Employed in Characterization or Purification of Examples
Analytical HPLC/MS was performed using the following methods:
Method A: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.
Method B: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.
Method C: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.
Method D: Analytical SFC—Shimadzu Nexera UC SFC, Column: Chiralpak AD, 4.6×100 mm, 5 micron (analytical, Flow Rate: 2 mL/min., Oven Temperature: 40 C, BPR setting: 1700 psi, UV wavelength: 220 nm, Mobile Phase: 80% CO2/20% Methanol-0.1% DEA (isocratic).
Method E: Analytical SFC—Shimadzu Nexera UC SFC, Column: Chiralpak AD, 4.6×100 mm, 5 micron (analytical), Flow Rate: 2 mL/min., Oven Temperature: 40 C, BPR setting: 1700 psi, UV wavelength: 220 nm. Mobile Phase: 75% CO2/25% Isopropanol-0.1% DEA (isocratic).

Example 1

N-(4-Chlorophenyl)-2-((1r,4r)-3'H-spiro[cyclohexane-1,1'-isobenzofuran]-4-yl)acetamide

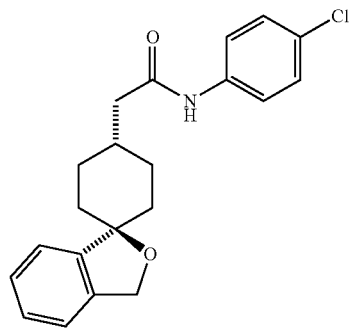 [SMILES: O=C(C[C@H]1CC[C@@]2(CC1)OCc1ccccc12)Nc1ccc(Cl)cc1]

1A. 8-(2-(Hydroxymethyl)phenyl)-1,4-dioxaspiro[4.5]decan-8-ol

An oven dried three necked flask was charged with (2-bromophenyl)methanol (2.08 g, 11.12 mmol) and sealed under nitrogen. The starting material was dissolved in dry THF (23 mL) and cooled to −78° C. A solution of n-butyllithium in hexanes (10.23 ml, 25.6 mmol) was added dropwise. The reaction was then stirred for 0.5 hour. 1,4-Dioxaspiro[4.5]decan-8-one (1.737 g, 11.12 mmol) was dissolved in THF (5 mL) and added to the reaction. The reaction was allowed to warm gradually to room temperature. The reaction was quenched with ammonium chloride solution and extracted twice with ether. The combined organic layers were washed with brine. The solution was dried over magnesium sulfate, filtered and evaporated to give the crude product. This material was purified on an 80 g Isco silica gel column, eluting with 0-100% ethyl acetate in hexanes. Evaporation of the appropriate fractions gave 8-(2-(hydroxymethyl)phenyl)-1,4-dioxaspiro[4.5]decan-8-ol (756 mg, 2.86 mmol, 25.7% yield) as a colorless solid. $^1$H NMR (400 MHz, DMSO-d$_6$) δ 7.54 (dd, J=7.4, 1.8 Hz, 1H), 7.38 (dd, J=7.6, 1.7 Hz, 1H), 7.20 (quind, J=7.3, 1.7 Hz, 2H), 5.09-5.02 (m, 1H), 4.99 (s, 1H), 4.82 (d, J=5.5 Hz, 2H), 3.89 (s, 4H), 2.05-1.93 (m, 4H), 1.88-1.78 (m, 2H), 1.54 (br d, J=9.0 Hz, 2H).

1B. 3'H-spiro[Cyclohexane-1,1'-isobenzofuran]-4-one 8-(2-(Hydroxymethyl)phenyl)-1,4-dioxaspiro[4.5]decan-8-ol (756 mg, 2.86 mmol) was dissolved in 80% TFA (8 mL). The reaction was stirred overnight. In the morning, the reaction was cooled to −20° C. and THF (6 mL) was added. The pH was adjusted to ~11 with the careful addition of 25% NaOH. Water was added to induce precipitation. The solution was filtered and rinsed well with water. The resulting solid was dried in vacuo for 0.5 hour at 70° C. 3'H-spiro[cyclohexane-1,1'-isobenzofuran]-4-one (0.86 g, 4.25 mmol, 66.1% yield) was isolated as a tan solid. $^1$H NMR (400 MHz, DMSO-d$_6$) δ 7.40-7.25 (m, 4H), 5.10 (s, 2H), 2.84-2.61 (m, 2H), 2.31-2.16 (m, 4H), 2.05-1.91 (m, 2H).

1C. rac-(R,Z)-Ethyl 2-(3'H-spiro[cyclohexane-1,1'-isobenzofuran]-4-ylidene)acetate A two neck flask was charged with sodium hydride (128 mg, 3.20 mmol) under nitrogen. THF (6.4 mL) was added and the reaction cooled in an ice bath. Triethyl phosphonoacetate (641 μl, 3.20 mmol) was added dropwise and stirring continued for 10 minutes. 3'H-spiro[cyclohexane-1,1'-isobenzofuran]-4-one (405 mg, 2.002 mmol) was dissolved in THF (3 mL) and added dropwise. The reaction was stirred for a few minutes then the cooling bath was removed. The reaction was then quenched with saturated ammonium chloride. This mixture was transferred to a separatory funnel and twice extracted with ethyl acetate. The combined organic layers were washed with water then brine. The organic phase was dried over magnesium sulfate, filtered and evaporated. The crude product was applied to a 40 g Isco silica gel column and eluted with 0-100% ethyl acetate in hexanes. Evaporation of the appropriate fractions gave rac-(R,Z)-ethyl 2-(3'H-spiro[cyclohexane-1,1'-isobenzofuran]-4-ylidene)acetate (387 mg, 1.421 mmol, 71.0% yield). $^1$H NMR (400 MHz, CHLOROFORM-d) δ 7.31-7.22 (m, 4H), 7.12-7.06 (m, 1H), 5.75 (s, 1H), 5.13 (s, 2H), 4.20 (q, J=7.2 Hz, 2H), 3.90-3.80 (m, 1H), 2.75 (td, J=13.4, 4.6 Hz, 1H), 2.47 (td, J=13.7, 4.6 Hz, 1H), 2.34-2.24 (m, 1H), 2.06-1.95 (m, 2H), 1.92-1.79 (m, 2H), 1.32 (t, J=7.2 Hz, 3H). $^{13}$C NMR (101 MHz, CHLOROFORM-d) δ 166.8, 161.8, 145.2, 138.9, 127.7, 127.3, 121.2, 120.6, 113.8, 86.1, 70.9, 59.6, 38.3, 37.6, 33.9, 14.4.

1D. Ethyl 2-((1r,4r)-3'H-spiro[cyclohexane-1,1'-isobenzofuran]-4-yl)acetate and

1E. Ethyl 2-((1s,4s)-3'H-spiro[cyclohexane-1,1'-isobenzofuran]-4-yl)acetate

A Parr bottle was charged with rac-(R,Z)-ethyl 2-(3'H-spiro[cyclohexane-1,1'-isobenzofuran]-4-ylidene)acetate (285 mg, 1.046 mmol) in ethyl acetate (ca. 15 mL). 10% Pd/C (100 mg) was added and a hydrogen atmosphere was introduced (ca. 40 psi). Upon completion of the reduction, the catalyst was filtered off and the filtrate was evaporated. The mixture was purified by RP-HPLC (methanol-water gradient+0.1% TFA). Evaporation provided ethyl 2-((r,4r)-3'H-spiro[cyclohexane-1,1'-isobenzofuran]-4-yl)acetate (46.6 mg, 0.170 mmol, 16.23% yield) and ethyl 2-((1s,4s)-3'H-spiro[cyclohexane-1,1'-isobenzofuran]-4-yl)acetate (188 mg, 0.685 mmol, 65.5% yield). 1D: $^1$H NMR (500 MHz, CHLOROFORM-d) δ 7.35-7.32 (m, 1H), 7.31-7.26 (m, 2H), 7.24-7.20 (m, 1H), 5.08 (s, 2H), 4.19 (q, J=7.2 Hz, 2H), 2.46 (d, J=7.3 Hz, 2H), 2.21 (tquin, J=7.5, 3.8 Hz, 1H), 2.02-1.93 (m, 2H), 1.93-1.85 (m, 2H), 1.81-1.71 (m, 2H), 1.66-1.54 (m, 3H), 1.30 (t, J=7.1 Hz, 3H). $^{13}$C NMR (126 MHz, CHLOROFORM-d) δ 173.1, 146.1, 139.4, 127.4, 127.0, 121.5, 121.2, 86.5, 70.5, 60.3, 38.9, 34.3, 31.5, 27.5, 14.3. 1E: $^1$H NMR (500 MHz, CHLOROFORM-d) δ 7.31-7.26 (m, 2H), 7.24-7.20 (m, 1H), 7.14-7.08 (m, 1H), 5.16-4.95 (m, 2H), 4.17 (q, J=7.1 Hz, 2H), 2.30 (d, J=7.0 Hz, 2H), 2.00-1.89 (m, 1H), 1.88-1.81 (m, 2H), 1.79-1.67 (m, 4H), 1.61-1.47 (m, 2H), 1.29 (t, J=7.2 Hz, 3H). $^{13}$C NMR (126 MHz, CHLOROFORM-d) δ 173.2, 146.4, 138.8, 127.4, 127.3, 121.1, 120.6, 86.2, 70.7, 60.2, 41.9, 36.5, 33.9, 28.9, 14.3.

1F. rel-2-((1r,4r)-3'H-spiro[Cyclohexane-1,1'-isobenzofuran]-4-yl)acetic Acid

Ethyl 2-((1r,4r)-3'H-spiro[cyclohexane-1,1'-isobenzofuran]-4-yl)acetate (46 mg, 0.168 mmol) was dissolved in THF-water (3:1, 4 mL). A 1 M solution of lithium hydroxide (251 µl, 0.251 mmol) was added. Ethanol was added dropwise until a homogeneous solution was obtained. After stirring overnight, 1 N hydrochloric acid (251 uL) was added. The reaction was concentrated under a stream of nitrogen. The product was then extracted with methylene chloride. Drying over magnesium sulfate, filtration and evaporation gave rel-2-((1r,4r)-3'H-spiro[cyclohexane-1,1'-isobenzofuran]-4-yl)acetic acid (37.3 mg, 0.151 mmol, 90% yield) as a colorless oil. $^1$H NMR (400 MHz, CHLOROFORM-d) δ 7.41-7.13 (m, 4H), 5.09 (s, 2H), 2.52 (d, J=7.3 Hz, 2H), 2.32-2.18 (m, 1H), 2.06-1.95 (m, 2H), 1.91-1.85 (m, 2H), 1.83-1.72 (m, 2H), 1.69-1.57 (m, 2H).

Example 1

A reaction vial was charged with rel-2-((1r,4r)-3'H-spiro[cyclohexane-1,1'-isobenzofuran]-4-yl)acetic acid (12.7 mg, 0.052 mmol) in DMF (250 mL). Reaction was initiated with the sequential addition of 4-chloroaniline (9.87 mg, 0.077 mmol), triethylamine (21.56 µl, 0.155 mmol) and BOP (34.2 mg, 0.077 mmol). After stirring overnight, the reaction was diluted with DMF (0.75 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-85% B over 20 minutes, then a 5-minute hold at 100% B; Flow: 20 mL/min. Fractions containing the desired product were combined and dried via centrifugal evaporation to give N-(4-chlorophenyl)-2-((r,4r)-3'H-spiro[cyclohexane-1,1'-isobenzofuran]-4-yl)acetamide (8.3 mg, 0.023 mmol, 44%). $^1$H NMR (500 MHz, DMSO-d6) δ 10.09 (s, 1H), 7.64 (m 2H), 7.39 (br d, J=3.2 Hz, 1H), 7.35 (br d, J=8.7 Hz, 2H), 7.28 (br s, 3H), 4.95 (s, 2H), 2.48 (br d, J=7.6 Hz, 2H), 2.16 (br s, 1H), 1.84 (br d, J=9.4 Hz, 4H), 1.65-1.41 (m, 4H). LC-MS Anal. Calc'd for $C_{21}H_{22}ClNO_2$ 355.13, found [M+H] 356.2, $T_r$=2.03 min (Method A).

Example 2

N-((1R,3S)-Adamantan-1-yl)-2-((1R,4r)-3'H-spiro[cyclohexane-1,1'-isobenzofuran]-4-yl)acetamide

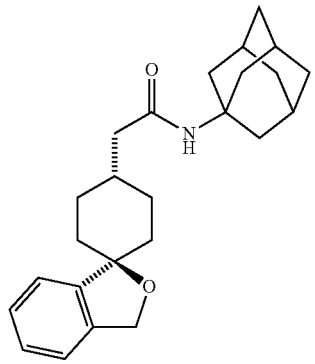 [SMILES: O=C(C[C@H]1CC[C@@]2(CC1)OCc1ccccc12)NC12CC3CC(CC(C3)C1)C2]

A reaction vial was charged with rel-2-((1r,4r)-3'H-spiro[cyclohexane-1,1'-isobenzofuran]-4-yl)acetic acid (12.7 mg, 0.052 mmol) (Intermediate 1D) in DMF (250 mL). The reaction was initiated with the sequential addition of (3s,5s,7s)-adamantan-1-amine (7.80 mg, 0.052 mmol), triethylamine (21.56 µl, 0.155 mmol) and BOP (34.2 mg, 0.077 mmol). The reaction was stirred overnight. DMF (1.75 mL) was added. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 5-minute hold at 100% B; Flow: 20 mL/min. Fractions containing the desired product were combined and dried via centrifugal evaporation to give N-((1R,3S)-adamantan-1-yl)-2-((1R,4r)-3'H-spiro[cyclohexane-1,1'-isobenzofuran]-4-yl)acetamide (4.7 mg, 0.012 mmol, 24%). $^1$H NMR (500 MHz, DMSO-$d_6$) δ 7.45-7.33 (m, 2H), 7.26 (br s, 3H), 4.92 (s, 2H), 2.15 (br d, J=7.5 Hz, 2H), 1.98 (br s, 4H), 1.91 (br s, 6H), 1.84-1.68 (m, 4H), 1.60 (br s, 6H), 1.55-1.48 (m, 2H), 1.43 (br d, J=7.1 Hz, 2H). LC-MS Anal. Calc'd for $C_{25}H_{33}NO_2$ 379.25, found [M+H] 380.0, $T_r$=2.25 min (Method A).

Example 3

N-(4-Chlorophenyl)-2-((1s,4s)-3'H-spiro[cyclohexane-1,1'-isobenzofuran]-4-yl)acetamide

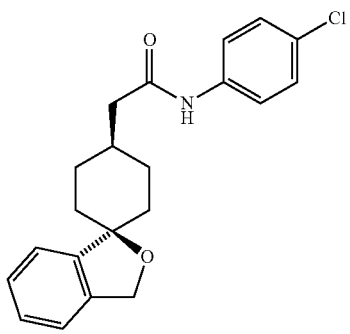 [SMILES: O=C(C[C@H]1CC[C@]2(CC1)OCc1ccccc12)Nc1ccc(Cl)cc1]

A reaction vial was charged with 2-((1s,4s)-3'H-spiro[cyclohexane-1,1'-isobenzofuran]-4-yl)acetic acid (12.2 mg, 0.050 mmol) in DMF (250 mL). The reaction was initiated with the sequential addition of 4-chloroaniline (9.48 mg, 0.074 mmol), triethylamine (20.71 µl, 0.149 mmol) and BOP (32.9 mg, 0.074 mmol). The reaction was stirred overnight when it was diluted with DMF (0.75 mL). The crude material was purified via preparative LC/MS with the following conditions: Column: XBridge Shield RP18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 10-minute hold at 100% B; Flow: 20 mL/min. Fractions containing the desired product were combined and dried via centrifugal evaporation. $^1$H NMR (500 MHz, DMSO-$d_6$) δ 10.06 (s, 1H), 7.62 (br d, J=8.7 Hz, 2H), 7.34 (br d, J=8.7 Hz, 2H), 7.28-7.13 (m, 4H), 4.94 (s, 2H), 2.25 (br d, J=7.0 Hz, 2H), 1.90 (br s, 1H), 1.78-1.57 (m, 6H), 1.50-1.32 (m, 2H). LC-MS Anal. Calc'd for $C_{21}H22ClNO_2$ 355.13, found [M+H] 356.2, $T_r$=2.10 min (Method A).

Example 4 rac-N-(4-Chlorophenyl)-2-((1r,4r)-3'H-spiro[cyclohexane-1,1'-isobenzofuran]-4-yl)propanamide

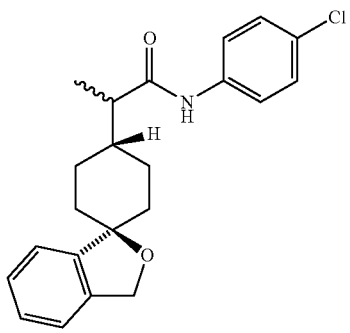 [SMILES: CC(C(=O)Nc1ccc(Cl)cc1)[C@H]1CC[C@@]2(CC1)OCc1ccccc12]

4A. rac-(R,Z)-ethyl 2-(3'H-spiro[cyclohexane-1,1'-isobenzofuran]-4-ylidene)propanoate A two neck flask was charged with sodium hydride (272 mg, 6.80 mmol) under nitrogen. THF (12 mL) was added and the reaction cooled in an ice bath. Triethyl 2-phosphonopropionate (1368 µl, 6.38 mmol) was added dropwise and stirring continued for 10 minutes. 3'H-spiro[cyclohexane-1,1'-isobenzofuran]-4-one (860 mg, 4.25 mmol) (Intermediate 1B) was dissolved in THF (5 mL) and added dropwise. After stirring for a few minutes, the cooling bath was removed. LCMS suggested rapid conversion to the desired product. The reaction was quenched with saturated ammonium chloride and transferred to a separatory funnel. The mixture was extracted with ethyl acetate. Some additional water was added to dissolve suspended salts. The aqueous layer was extracted with an additional portion of ethyl acetate. The combined organic layers were washed with water and then brine. Drying over magnesium sulfate, filtration and evaporation provided the crude product. This material was applied to an 80 g Isco silica gel column and eluted with 0-25% ethyl acetate in hexanes. Evaporation of the appropriate fractions gave rac-(R,Z)-ethyl 2-(3'H-spiro[cyclohexane-1,1'-isobenzofuran]-4-ylidene)propanoate (973 mg, 3.40 mmol, 80% yield). $^1$H NMR (400 MHz, CHLOROFORM-d) δ 7.32-7.21 (m, 3H), 7.13-7.07 (m, 1H), 5.12 (s, 2H), 4.24 (q, J=7.1 Hz, 2H), 3.11-3.02 (m, 1H), 2.70-2.60 (m, 1H), 2.52-2.37 (m, 2H), 2.05-1.90 (m, 5H), 1.89-1.73 (m, 2H), 1.34 (t, J=7.2 Hz, 3H). $^{13}$C NMR (101 MHz, CHLOROFORM-d) δ 170.5, 146.2, 145.5, 139.0, 127.6, 127.3, 121.1, 120.7, 120.7, 86.4, 70.8, 60.3, 38.1, 37.7, 28.1, 27.1, 15.3, 14.3.

4B. rac-ethyl 2-((1r,4r)-3'H-spiro[cyclohexane-1,1'-isobenzofuran]-4-yl)propanoate and

4C. rac-ethyl 2-((1s,4s)-3'H-spiro[cyclohexane-1,1'-isobenzofuran]-4-yl)propanoate A Parr bottle was charged with rac-(R,Z)-ethyl 2-(3'H-spiro[cyclohexane-1,1'-isobenzofuran]-4-ylidene)propanoate (162 mg, 0.566 mmol) in ethyl acetate (5 mL). 5% Rh/C (44 mg) was added and the bottle pressurized with 45 psi hydrogen. After three hours, the catalyst was filtered off and the solvent evaporated. TLC (silica 9:1 hexanes-ethyl acetate) showed two spots, a major fast and a minor slow. The material was purified by RP-HPLC (methanol-water gradient+0.1% TFA). Evaporation of the appropriate fractions gave rac-ethyl 2-((1s,4s)-3'H-spiro[cyclohexane-1,1'-isobenzofuran]-4-yl)propanoate (64.2 mg, 0.223 mmol, 39.4% yield) and rac-ethyl 2-((1r,4r)-3'H-spiro[cyclohexane-1,1'-isobenzofuran]-4-yl)propanoate (38.6 mg, 0.134 mmol, 23.66% yield) as colorless oils.

4B: $^1$H NMR (400 MHz, CHLOROFORM-d) δ 7.39-7.35 (m, 1H), 7.33-7.26 (m, 2H), 7.25-7.19 (m, 1H), 5.08 (s, 2H), 4.26-4.13 (m, 2H), 2.60 (quin, J=7.3 Hz, 1H), 2.00-1.80 (m, 5H), 1.80-1.54 (m, 4H), 1.31 (t, J=7.2 Hz, 3H), 1.24 (d, J=7.0 Hz, 3H).

4C: $^1$H NMR (400 MHz, METHANOL-d4) δ 7.29-7.21 (m, 3H), 7.19-7.10 (m, 1H), 5.02 (s, 2H), 4.22-4.08 (m, 2H), 2.34 (quin, J=7.0 Hz, 1H), 1.89-1.67 (m, 6H), 1.64-1.46 (m, 3H), 1.29 (t, J=7.2 Hz, 3H), 1.17 (d, J=7.0 Hz, 3H).

4D. rac-2-((1r,4r)-3'H-spiro[cyclohexane-1,1'-isobenzofuran]-4-yl)propanoic Acid rac-ethyl 2-((1r,4r)-3'H-spiro[cyclohexane-1,1'-isobenzofuran]-4-yl)propanoate (65 mg, 0.225 mmol) was dissolved in THF (3 mL) and water (1 mL). Lithium hydroxide (1 M solution)(676 µl, 0.676 mmol) was added. Ethanol was added dropwise until a clear solution was obtained. The reaction was then heated to 55° C. and stirred overnight. Additional lithium hydroxide solution (0.676 mL, 0.676 mmol) was added and heating continued. The next day the cooled reaction was quenched with 1 N hydrochloric acid (1.35 mL). The reaction was concentrated under a stream of nitrogen. The resulting solid was filtered and rinsed with water. This crude material was purified by RP-HPLC (methanol-water gradient+0.1% TFA). Evaporation of the product containing fractions gave rac-2-((1r,4r)-3'H-spiro[cyclohexane-1,1'-isobenzofuran]-4-yl)propanoic acid (16.6 mg, 0.064 mmol, 28%) as a colorless oil. $^1$H NMR (400 MHz, CHLOROFORM-d) δ 7.40-7.35 (m, 1H), 7.34-7.29 (m, 1H), 7.28-7.25 (m, 1H), 7.25-7.21 (m, 1H), 5.10 (s, 2H), 2.65 (quin, J=7.2 Hz, 1H), 2.05-1.85 (m, 6H), 1.84-1.64 (m, 4H), 1.29 (d, J=7.0 Hz, 3H). $^{13}$C NMR (101 MHz, CHLOROFORM-d) δ 182.3, 145.6, 139.3, 127.5, 127.0, 121.7, 121.3, 86.9, 70.4, 42.5, 37.8, 35.2, 35.0, 26.3, 24.6, 14.9.

Example 4

A reaction vial was charged with rac-2-((1r,4r)-3'H-spiro[cyclohexane-1,1'-isobenzofuran]-4-yl)propanoic acid (8.3 mg, 0.032 mmol) in DMF (375 uL). Reaction was initiated with the sequential addition of 4-chloroaniline (6.10 mg, 0.048 mmol), triethylamine (13.33 µl, 0.096 mmol) and BOP (21.15 mg, 0.048 mmol). After stirring for 3 days, the reaction was diluted with DMF (0.65 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation to give rac-N-(4-chlorophenyl)-2-((1r,4r)-3'H-spiro[cyclohexane-1,1'-isobenzofuran]-4-yl)propanamide (4.5 mg, 0.012 mmol, 38%). $^1$H NMR (500 MHz, DMSO-d$_6$) δ 10.09 (s, 1H), 7.66 (br d, J=8.8 Hz, 2H), 7.41 (br d, J=3.7 Hz, 1H), 7.36 (br d, J=8.7 Hz, 2H), 7.28 (br d, J=3.1 Hz, 3H), 4.94 (s, 2H), 2.69 (br s, 1H), 1.98-1.82 (m, 2H), 1.81-1.66 (m, 3H), 1.64-1.46 (m, 4H), 1.15 (br d, J=6.6 Hz, 3H). LC-MS Anal. Calc'd for C$_{22}$H$_{24}$ClNO$_2$ 369.15, found [M–H] 368.1, T$_r$=2.26 min (Method B).

Example 5

N-(4-Chlorophenyl)-2-((1s,4s)-3'H-spiro[cyclohexane-1,1'-isobenzofuran]-4-yl)propanamide

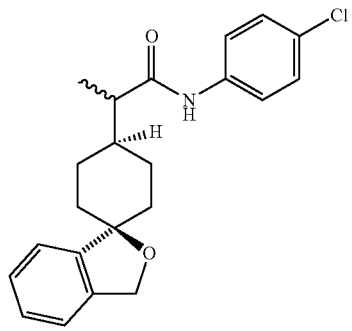 [SMILES: CC(C(=O)Nc1ccc(Cl)cc1)[C@H]1CC[C@]2(CC1)OCc1ccccc12]

5A. rac-2-((1s,4s)-3'H-spiro[cyclohexane-1,1'-isobenzofuran]-4-yl)propanoic Acid rac-Ethyl 2-((1s,4s)-3'H-spiro[cyclohexane-1,1'-isobenzofuran]-4-yl)propanoate (325 mg, 1.127 mmol) (Intermediate 4C) was dissolved in THF (8 mL) and water (2 mL). A 1 M solution of lithium hydroxide (2254 µl, 2.254 mmol) was added. Ethanol was added until a clear solution was obtained. The reaction was then heated to 55° C. and stirred overnight. An additional aliquot of lithium hydroxide solution (1.0 mL) was added and heating continued until the next day. The cooled solution was quenched with 1 N hydrochloric acid (3.25 mL) and concentrated under a stream of nitrogen. The resulting solid was filtered and rinsed with water. This material was dried at 70° C. This treatment provided rac-2-((1s,4s)-3'H-spiro[cyclohexane-1,1'-isobenzofuran]-4-yl)propanoic acid (260 mg, 0.979 mmol, 87% yield) as an off-white solid. $^1$H NMR (400 MHz, DMSO-d$_6$) δ 12.04 (s, 1H), 7.44-7.13 (m, 4H), 4.95 (s, 2H), 2.21 (quin, J=6.9 Hz, 1H), 1.77-1.35 (m, 9H), 1.06 (d, J=7.0 Hz, 3H). $^{13}$C NMR (101 MHz, DMSO-d$_6$) δ 177.4, 146.8, 139.1, 127.8, 127.6, 121.6, 121.2, 85.9, 70.3, 44.9, 36.5, 36.5, 27.1, 25.4, 14.2 (CH—CO2H likely obscured under the DMSO peak). LC-MS Anal. Calc'd for C$_{16}$H$_{20}$O$_3$ 260.14, found [M+H] 361.1, T$_r$=0.88 min (Method C).

Example 5

A reaction vial was charged with rac-2-((1s,4s)-3'H-spiro[cyclohexane-1,1'-isobenzofuran]-4-yl)propanoic acid (20 mg, 0.077 mmol) in DMF (500 uL). The reaction was initiated with the sequential addition of 4-chloroaniline (14.70 mg, 0.115 mmol), triethylamine (32.1 µl, 0.230 mmol) and BOP (51.0 mg, 0.115 mmol). After stirring overnight, the reaction was diluted with DMF (1.5 mL). The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-80% B over 20 minutes, then a 5-minute hold at 100% B; Flow: 20 mL/min. Fractions containing the desired product were combined and dried via centrifugal evaporation to give rac-N-(4-chlorophenyl)-2-((1s,4s)-3'H-spiro[cyclohexane-1,1'-isobenzofuran]-4-yl)propanamide (21.1 mg, 0.057 mmol, 74%). $^1$H NMR (500 MHz, DMSO-d$_6$) δ 10.03 (s, 1H), 7.65 (br d, J=8.8 Hz, 2H), 7.34 (br d, J=8.8 Hz, 2H), 7.24 (s, 3H), 7.21 (br d, J=2.5 Hz, 1H), 4.93 (s, 2H), 2.27 (br t, J=7.2 Hz, 1H), 1.82-1.45 (m, 8H), 1.41-1.26 (m, 1H), 1.10 (br d, J=6.7 Hz, 3H). LC-MS Anal. Calc'd for C$_{22}$H$_{24}$ClNO$_2$ 369.15, found [M+H]370.2, T$_r$=2.23 min (Method A).

Example 6 rac-N-((1R,3S)-Adamantan-1-yl)-2-((1S,4s)-3'H-spiro[cyclohexane-1,1'-isobenzofuran]-4-yl)propanamide

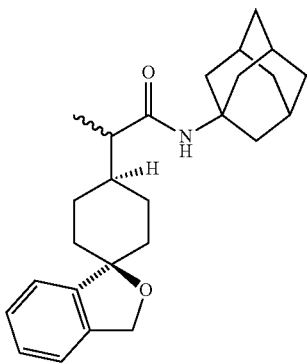 [SMILES: CC(C(=O)NC12CC3CC(CC(C3)C1)C2)[C@H]1CC[C@]2(CC1)OCc1ccccc12]

A reaction vial was charged with rac-2-((s,4s)-3'H-spiro[cyclohexane-1,1'-isobenzofuran]-4-yl)propanoic acid (20 mg, 0.077 mmol) (Intermediate 5A) in DMF (250 uL). The reaction was initiated with the sequential addition of (3s,5s,7s)-adamantan-1-amine (11.62 mg, 0.077 mmol), triethylamine (32.1 µl, 0.230 mmol) and BOP (51.0 mg, 0.115 mmol). After stirring overnight the reaction was diluted with DMF (1.75 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 5-minute hold at 100% B; Flow: 20 mL/min. Fractions containing the desired product were combined and dried via centrifugal evaporation to give rac-N-((1R,3S)-adamantan-1-yl)-2-((1S,4s)-3'H-spiro[cyclohexane-1,1'-isobenzofuran]-4-yl)propanamide (15.3 mg, 0.039 mmol, 51%). $^1$H NMR (500 MHz, DMSO-$d_6$) δ 7.31-7.17 (m, 5H), 4.93 (s, 2H), 1.99 (br s, 4H), 1.92 (br s, 6H), 1.75-1.50 (m, 11H), 1.41 (br d, J=4.9 Hz, 2H), 1.32-1.15 (m, 1H), 0.95 (br d, J=6.7 Hz, 3H). LC-MS Anal. Calc'd for $C_{26}H_{35}NO_2$ 393.56, found [M+H] 394.4, $T_r$=2.45 min (Method A).

Example 7 rac-N-(4-Chlorophenyl)-2-((1r,4r)-7'-methyl-3'H-spiro[cyclohexane-1,1'-isobenzofuran]-4-yl)propanamide

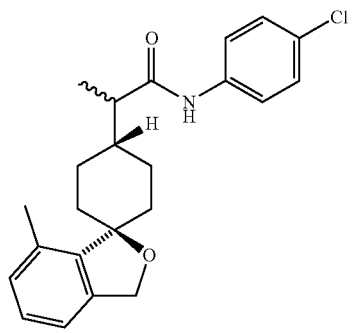 [SMILES: Cc1cccc2c1[C@]1(CC[C@@H](C(C)C(=O)Nc3ccc(Cl)cc3)CC1)OC2]

7A. 8-(2-(Hydroxymethyl)-6-methylphenyl)-1,4-dioxaspiro[4.5]decan-8-ol

An oven dried two necked flask was charged with (2-bromo-3-methylphenyl)methanol (620 mg, 3.08 mmol) and sealed under nitrogen. The starting material was dissolved in dry THF (10 mL) and cooled to −78° C. A solution of n-butyllithium (2529 µl, 6.32 mmol)(2.5 M in hexanes) was added dropwise and stirring continued for 0.5 hour. 1,4-dioxaspiro[4.5]decan-8-one (482 mg, 3.08 mmol) in THF (2 mL) was then added. The reaction was allowed to warm gradually to RT. The reaction was quenched with ammonium chloride solution. This solution was extracted twice with ether. The combined organic layers were washed with brine. Drying over magnesium sulfate, filtration and evaporation provided the crude product. Purification was accomplished on a 40 g Isco silica gel column eluting with 0-50% ethyl acetate in hexanes. Evaporation of the appropriate fractions gave 8-(2-(hydroxymethyl)-6-methylphenyl)-1,4-dioxaspiro[4.5]decan-8-ol (216 mg, 0.776 mmol, 25.2% yield) as a colorless film. $^1$H NMR (400 MHz, CHLOROFORM-d) δ 7.14 (br d, J=6.6 Hz, 1H), 7.11-6.97 (m, 2H), 4.93 (br s, 2H), 3.99 (s, 4H), 2.73-2.55 (m, 5H), 2.12 (td, J=13.1, 4.8 Hz, 2H), 1.77 (br d, J=13.7 Hz, 2H), 1.63 (br d, J=12.2 Hz, 2H). $^{13}$C NMR (101 MHz, CHLOROFORM-d) δ 145.5, 138.3, 135.8, 134.1, 130.8, 126.4, 108.9, 76.0, 68.6 (br s, 1C), 64.4, 64.3, 34.7, 30.2, 23.6.

7B. 7'-Methyl-3'H-spiro[cyclohexane-1,1'-isobenzofuran]-4-one 8-(2-(hydroxymethyl)-6-methylphenyl)-1,4-dioxaspiro[4.5]decan-8-ol (216 mg, 0.776 mmol) was dissolved in 80% aqueous TFA (5 mL). After stirring for 2 hours, the flask was cooled to −20° C. THF (1 mL) was added, followed by sodium hydroxide solution (until alkaline). The colorless precipitate that formed was filtered and rinsed with water. The solid was dried in vacuo at 70° C. for an hour. 7'-methyl-3'H-spiro[cyclohexane-1,1'-isobenzofuran]-4-one (134 mg, 0.620 mmol, 80% yield) was isolated as a colorless solid. $^1$H NMR (400 MHz, CHLOROFORM-d) δ 7.24-7.17 (m, 1H), 7.07 (d, J=7.5 Hz, 1H), 7.04 (d, J=7.5 Hz, 1H), 5.12 (s, 2H), 2.97 (m, 2H), 2.46 (m, 2H), 2.39 (m, 2H), 2.35 (s, 3H), 2.13 (m, 2H). $^{13}$C NMR (101 MHz, CHLOROFORM-d) δ 212.0, 141.5, 139.5, 131.3, 130.1, 128.1, 118.9, 86.2, 70.8, 38.0, 34.7, 18.6.

7C. rac-(R,Z)-Ethyl 2-(7'-methyl-3'H-spiro[cyclohexane-1,1'-isobenzofuran]-4-ylidene)propanoate A two neck flask was charged with sodium hydride (39.1 mg, 0.977 mmol) under nitrogen. THF (2 mL) was added and the reaction cooled in an ice bath. Triethyl 2-phosphonopropionate (196 µl, 0.915 mmol) was added dropwise and stirring continued for 10 minutes. 7'-Methyl-3'H-spiro[cyclohexane-1,1'-isobenzofuran]-4-one (132 mg, 0.610 mmol) was dissolved in THF (1 mL) and added dropwise. After stirring for a few minutes, the cooling bath was removed. Upon completion, the reaction was quenched with saturated ammonium chloride. The mixture was transferred to a separatory funnel and extracted twice with ethyl acetate. The combined organic layers were washed with brine. Drying over magnesium sulfate, filtration and evaporation provided the crude product. This material was applied to a 24 g Isco silica gel column and eluted with 0-25% ethyl acetate in hexanes. Evaporation of the appropriate fractions gave rac-(R,Z)-ethyl 2-(7'-methyl-3'H-spiro[cyclohexane-1,1'- isobenzofuran]-4-ylidene)propanoate (78 mg, 0.260 mmol, 42.5% yield). $^1$H NMR (400 MHz, CHLOROFORM-d) δ 7.22-7.14 (m, 1H), 7.05 (dd, J=10.7, 7.5 Hz, 2H), 5.07 (s, 2H), 4.24 (q, J=7.1 Hz, 2H), 3.09 (ddt, J=13.7, 4.3, 2.4 Hz, 1H), 2.71-2.60 (m, 1H), 2.57-2.40 (m, 2H), 2.37 (s, 3H), 2.16-2.09 (m, 1H), 2.09-2.02 (m, 1H), 1.96 (t, J=1.5 Hz, 3H), 1.95-1.86 (m, 2H), 1.34 (t, J=7.1 Hz, 3H). $^{13}$C NMR (101 MHz, CHLOROFORM-d) δ 170.5, 146.7, 142.5, 139.6, 131.4, 129.9, 127.6, 120.5, 118.7, 87.3, 70.4, 60.2, 35.8, 35.3, 27.9, 27.1, 18.7, 15.3, 14.3.

7D. rac-Ethyl 2-((1r,4r)-7'-methyl-3'H-spiro[cyclohexane-1,1'-isobenzofuran]-4-yl)propanoate and 7E. rac-Ethyl 2-((1s,4s)-7'-methyl-3'H-spiro[cyclohexane-1,1'-isobenzofuran]-4-yl)propanoate A Parr bottle was charged with rac-(R,Z)-ethyl 2-(7'-methyl-3'H-spiro[cyclohexane-1,1'-isobenzofuran]-4-ylidene)propanoate (78 mg, 0.260 mmol) in ethanol (ca. 10 mL). 5% Rh/C (42.5 mg) was added and the bottle was pressurized to 40 psi hydrogen. Upon completion, the reaction was filtered and evaporated. The sample was purified by RP-HPLC (methanol-water gradient+0.1% TFA). Evaporation of the appropriate fractions provided rac-ethyl 2-((1s,4s)-7'-methyl-3'H-spiro[cyclohexane-1,1'-isobenzofuran]-4-yl)propanoate (46.4 mg, 0.153 mmol, 59.1% yield) and rac-ethyl 2-((1r,4r)-7'-methyl-3'H-spiro[cyclohexane-1,1'-isobenzofuran]-4-yl)propanoate (16.4 mg, 0.054 mmol, 20.89% yield).

7D: $^1$H NMR (500 MHz, CHLOROFORM-d) δ 7.21-7.16 (m, 1H), 7.05 (overlapping Hs, 2H), 5.03 (s, 2H), 4.26-4.10 (m, 2H), 2.82 (ds, J=11.2, 6.8 Hz, 1H), 2.45 (s, 3H), 2.27-2.13 (m, 1H), 2.09-1.92 (m, 4H), 1.83-1.74 (m, 1H), 1.60-1.54 (m, 1H), 1.53-1.46 (m, 1H), 1.29 (t, J=7.1 Hz, 3H), 1.24 (d, J=6.9 Hz, 3H). $^{13}$C NMR (126 MHz, CHLOROFORM-d) δ 177.1, 143.5, 139.4, 131.2, 130.0, 127.5, 118.7, 87.6, 70.4, 60.2, 39.2, 35.4, 29.3, 28.9, 25.3, 22.7, 18.6, 16.1, 14.3.

7E: $^1$H NMR (400 MHz, CHLOROFORM-d) δ 7.21-7.14 (m, 1H), 7.11-6.97 (m, 2H), 5.05 (s, 2H), 4.30-4.09 (m, 2H), 2.41 (s, 3H), 2.36 (quin, J=7.0 Hz, 1H), 2.10-1.96 (m, 2H), 1.94-1.43 (m, 7H), 1.31 (t, J=7.1 Hz, 3H), 1.20 (d, J=7.0 Hz, 3H). $^{13}$C NMR (101 MHz, CHLOROFORM-d) δ 177.2, 143.0, 139.2, 131.3, 130.0, 127.6, 118.7, 87.8, 70.3, 60.4, 45.4, 39.7, 34.2 (d, J=1.1 Hz, 1C), 27.2, 25.3, 18.6, 14.3, 14.1.

7F. rac-2-((1r,4r)-7'-Methyl-3'H-spiro[cyclohexane-1,1'-isobenzofuran]-4-yl)propanoic Acid A reaction vial was charged with rac-ethyl 2-((1r,4r)-7'-methyl-3'H-spiro[cyclohexane-1,1'-isobenzofuran]-4-yl)propanoate (16.9 mg, 0.056 mmol) in THF (2 mL), water (1 mL) and sodium hydroxide (279 µl, 0.279 mmol)(1 N). Ethanol was added dropwise until a homogeneous solution was obtained. Nitrogen was bubbled through the solution for a few minutes when the vial was sealed and warmed to 55° C. After stirring overnight, LCMS analysis showed partial conversion to product. An additional aliquot of sodium hydroxide (0.279 mL) was added and heating continued for 3 hours. The reaction was then allowed to stir at RT for two days. 1 N hydrochloric acid (0.66 mL) was added and the solvent was concentrated under a stream of nitrogen. The solution was extracted twice with ethyl acetate and the combined organic layers were dried over magnesium sulfate, filtered and evaporated. This treatment provided rac-2-((1r,4r)-7'-methyl-3'H-spiro[cyclohexane-1,1'-isobenzofuran]-4-yl)propanoic acid (13.9 mg, 0.051 mmol, 91% yield) as a yellow oil.

Example 7 rac-2-((1r,4r)-7'-methyl-3'H-spiro[cyclohexane-1,1'-isobenzofuran]-4-yl)propanoic acid (13.9 mg, 0.051 mmol) was dissolved in DMF (0.5 mL). 4-Chloroaniline (7.76 mg, 0.061 mmol) and triethylamine (35.3 µl, 0.253 mmol) were added. The reaction was initiated with the addition of BOP (31.4 mg, 0.071 mmol). After 2 hours, LCMS analysis suggested formation of the looks HOBT ester. A catalytic amount of DMAP was added and the reaction warmed to 55° C. The cooled reaction was diluted with methanol and purified by RP-HPLC (methanol-water gradient+0.1% TFA). Evaporation of the product containing fractions to gave rac-N-(4-chlorophenyl)-2-((1r,4r)-7'-methyl-3'H-spiro[cyclohexane-1,1'-isobenzofuran]-4-yl)propanamide (2.5 mg, 6.37 µmol, 12.57% yield). $^1$H NMR (500 MHz, CHLOROFORM-d) δ 7.51 (d, J=8.9 Hz, 2H), 7.32 (d, J=8.9 Hz, 2H), 7.21-7.17 (m, 1H), 7.13 (s, 1H), 7.06 (d, J=7.5 Hz, 2H), 5.04 (s, 2H), 2.47 (s, 3H), 2.22-1.94 (m, 6H), 1.81 (br d, J=13.7 Hz, 1H), 1.65 (br d, J=11.4 Hz, 3H), 1.35 (d, J=6.9 Hz, 3H). LC-MS Anal. Calc'd for $C_{23}H_{26}ClNO_2$ 383.16, found [M+H] 384.2, $T_r$=1.10 min (Method C).

Example 8 rac-N-(4-chlorophenyl)-2-((1s,4s)-7'-methyl-3'H-spiro[cyclohexane-1,1'-isobenzofuran]-4-yl)propanamide

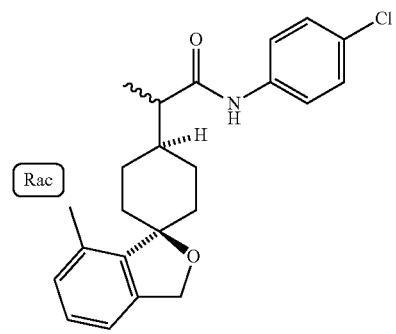 [SMILES: Cc1cccc2c1[C@]1(CC[C@H](C(C)C(=O)Nc3ccc(Cl)cc3)CC1)OC2]

8A. rac-2-((1s,4s)-7'-Methyl-3'H-spiro[cyclohexane-1,1'-isobenzofuran]-4-yl)propanoic Acid Reaction vial charged with rac-ethyl 2-((1s,4s)-7'-methyl-3'H-spiro[cyclohexane-1,1'-isobenzofuran]-4-yl)propanoate (46.4 mg, 0.153 mmol) (Intermediate 7E) in THF (2 mL), water (1 mL) and sodium hydroxide (460 µl, 0.460 mmol)(1 N). A little ethanol was added until a homogeneous solution was obtained. Nitrogen was bubbled through the solution for a few minutes when the vials was sealed and warmed to 55° C. After stirring overnight, LCMS analysis suggested partial conversion to product. An additional aliquot of sodium hydroxide (0.2 mL) was added and heating continued for 3 hours. The reaction was then allowed to stir at RT over the weekend. 1 N hydrochloric acid (0.66 mL) was added and the solvent concentrated under a stream of nitrogen. The solution was extract with twice with ethyl acetate. The combined organic layers were dried over magnesium sulfate, filtered and evaporated to give rac-2-((1s,4s)-7'-methyl-3'H-spiro[cyclohexane-1,1'-isobenzofuran]-4-yl)propanoic acid (41.7 mg, 0.152 mmol, 99% yield) as a yellow oil. $^1$H NMR (400 MHz, CHLOROFORM-d) δ 7.21-7.14 (m, 1H), 7.04 (dd, J=7.3, 3.7 Hz, 2H), 5.03 (s, 2H), 2.46-2.37 (m, 4H), 2.06-1.90 (m, 3H), 1.89-1.80 (m, 2H), 1.78-1.66 (m, 4H), 1.60 (td, J=12.8, 3.2 Hz, 1H), 1.23 (d, J=7.0 Hz, 3H).

Example 8

A reaction vial was charged with rac-2-((1s,4s)-7'-methyl-3'H-spiro[cyclohexane-1,1'-isobenzofuran]-4-yl)propanoic acid (13.9 mg, 0.051 mmol) (Intermediate 7E) in DMF (0.5 uL). The reaction was initiated with the sequential addition of 4-chloroaniline (9.69 mg, 0.076 mmol), triethylamine (21.18 μl, 0.152 mmol) and BOP (33.6 mg, 0.076 mmol). Partial conversion to product and HOBT ester was observed after stirring for a day. A spatula tip of DMAP was added and the reaction warmed to 55° C. for 2 hours. The cooled reaction was diluted with DMF (0.5 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 5-minute hold at 100% B; Flow: 20 mL/min. Fractions containing the desired product were combined and dried via centrifugal evaporation to give rac-N-(4-chlorophenyl)-2((1s,4s)-7'-methyl-3'H-spiro[cyclohexane-1,1'-isobenzofuran]-4-yl)propanamide (6.1 mg, 0.015 mmol, 30%). $^1$H NMR (500 MHz, DMSO-d$_6$) δ 10.03 (s, 1H), 7.65 (br d, J=8.7 Hz, 2H), 7.34 (br d, J=8.7 Hz, 2H), 7.17-7.11 (m, 1H), 7.05 (br d, J=7.3 Hz, 1H), 7.01 (br d, J=7.3 Hz, 1H), 4.89 (s, 2H), 2.33 (s, 3H), 2.27 (br t, J=7.1 Hz, 1H), 2.01-1.85 (m, 2H), 1.76 (br d, J=11.9 Hz, 1H), 1.66 (br d, J=13.0 Hz, 1H), 1.63-1.47 (m, 4H), 1.45-1.33 (m, 1H), 1.11 (br d, J=6.6 Hz, 3H). LC-MS Anal. Calc'd for C$_{23}$H$_{26}$ClNO$_2$ 383.16, found [M+H] 384.2, T$_r$=2.40 min (Method A).

Example 9 rac-N-((1R,3S)-adamantan-1-yl)-2-((1S,4s)-7'-methyl-3'H-spiro[cyclohexane-1,1'-isobenzofuran]-4-yl)propanamide

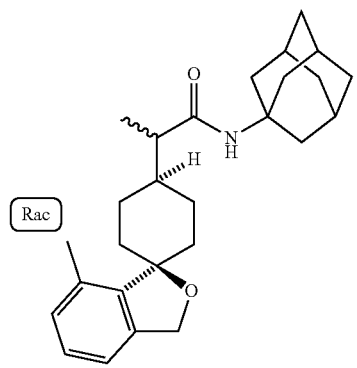 [SMILES: Cc1cccc2c1[C@]1(CC[C@H](C(C)C(=O)NC34CC5CC(CC(C5)C3)C4)CC1)OC2]

A reaction vial was charged with rac-2-((1s,4s)-7'-methyl-3'H-spiro[cyclohexane-1,1'-isobenzofuran]-4-yl)propanoic acid (13.9 mg, 0.051 mmol) (Intermediate 8A) in DMF (0.5 mL). The reaction was initiated with the sequential addition of (3s,5s,7s)-adamantan-1-amine (7.66 mg, 0.051 mmol), triethylamine (21.18 μl, 0.152 mmol) and BOP (33.6 mg, 0.076 mmol). After stirring for a day, a spatula tip of DMAP was added and the reaction warmed to 55° C. for two hours. The cooled reaction was diluted with DMF (0.5 mL). The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 50-100% B over 20 minutes, then a 5-minute hold at 100% B; Flow: 20 mL/min. Fractions containing the desired product were combined and dried via centrifugal evaporation to give rac-N-((1R,3S)-adamantan-1-yl)-2-((1S,4s)-7'-methyl-3'H-spiro[cyclohexane-1,1'-isobenzofuran]-4-yl)propanamide (13.0 mg, 0.031 mmol, 62%). $^1$H NMR (500 MHz, DMSO-d$_6$) δ 7.23 (s, 1H), 7.17-7.11 (m, 1H), 7.06 (br d, J=7.4 Hz, 1H), 7.04-6.97 (m, 1H), 4.88 (s, 2H), 2.33 (s, 3H), 2.08-1.80 (m, 12H), 1.75-1.50 (m, 10H), 1.49-1.35 (m, 2H), 1.34-1.24 (m, 1H), 0.95 (br d, J=6.6 Hz, 3H). LC-MS Anal. Calc'd for C$_{27}$H$_{37}$NO$_2$ 407.28, found [M+H] 408.0, T$_r$=2.62 min (Method B).

Example 10 rac-2-((1s,4s)-7'-methyl-3'H-spiro[cyclohexane-1,1'-isobenzofuran]-4-yl)-N-(1-methylcyclohexyl)propanamide

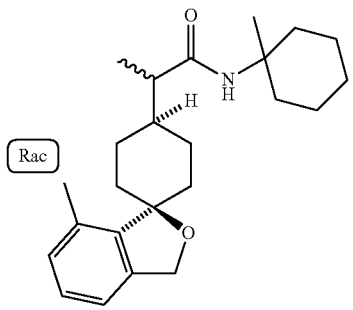 [SMILES: Cc1cccc2c1[C@]1(CC[C@H](C(C)C(=O)NC3(C)CCCCC3)CC1)OC2]

rac-2-((1s,4s)-7'-methyl-3'H-spiro[cyclohexane-1,1'-isobenzofuran]-4-yl)-N-(1-methylcyclohexyl)propanamide was prepared using the method of Example 9 starting with rac-2-((1s,4s)-7'-methyl-3'H-spiro[cyclohexane-1,1'-isobenzofuran]-4-yl)propanoic acid (13.9 mg, 0.051 mmol). The procedure generated 5.5 mg (28%) of Example 10. $^1$H NMR (500 MHz, DMSO-d$_6$) δ 7.17-7.12 (m, 1H), 7.08 (s, 1H), 7.05 (br d, J=7.3 Hz, 1H), 7.01 (br d, J=7.3 Hz, 1H), 4.88 (s, 2H), 2.33 (s, 3H), 2.13-1.98 (m, 3H), 1.97-1.80 (m, 2H), 1.75-1.51 (m, 4H), 1.49-1.28 (m, 8H), 1.22 (s, 6H), 0.97 (br d, J=6.7 Hz, 3H). LC-MS Anal. Calc'd for C$_{24}$H$_{35}$NO$_2$ 369.27, found [M+H] 370.2, T$_r$=2.36 min (Method A).

Example 11 rac-N-(1-((1s,4s)-3'H-spiro[cyclohexane-1,1'-isobenzofuran]-4-yl)ethyl)-4-chlorobenzamide

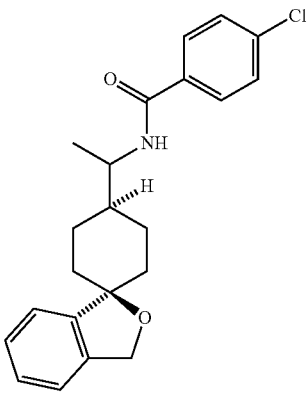 [SMILES: CC(NC(=O)c1ccc(Cl)cc1)[C@H]1CC[C@]2(CC1)OCc1ccccc12]

11A. rac-1-((1s,4s)-3'H-spiro[cyclohexane-1,1'-isobenzofuran]-4-yl)ethanamine A vial was charged with rac-2-((1s,4s)-3'H-spiro[cyclohexane-1,1'-isobenzofuran]-4-yl)propanoic acid (213 mg, 0.818 mmol) (Intermediate 5A) in dry toluene (4 mL) under nitrogen. Diphenylphosphoryl azide (212 µl, 0.982 mmol) and triethylamine (171 µl, 1.227 mmol) were then added. The reaction was heated to 75° C. After 5 hours, TLC (9:1 hexanes-ethyl acetate showed a major new spot). The cooled reaction was evaporated. This material was redissolved in THF (10 mL). A 1 N solution of lithium hydroxide (4091 µl, 4.09 mmol) was added and stirring continued overnight. The reaction was transferred to a separatory funnel and diluted with water. 1 N hydrochloric acid was added until the solution was acidic. The aqueous layer was extracted with ethyl acetate. The aqueous layer was then made basic with 1 N sodium hydroxide. The aqueous layer was the extracted three times with ethyl acetate. The combined organic phase was dried with magnesium sulfate, filtered and evaporated. The procedure provided rac-1-((1s,4s)-3'H-spiro[cyclohexane-1,1'-isobenzofuran]-4-yl)ethanamine (96.5 mg, 0.417 mmol, 51.0% yield) as an oil in sufficient purity for the subsequent transformations. $^1$H NMR (400 MHz, CHLOROFORM-d) δ 7.30-7.24 (m, 2H), 7.23-7.18 (m, 1H), 7.12-7.06 (m, 1H), 5.06 (s, 2H), 2.80 (quin, J=6.3 Hz, 1H), 1.94-1.84 (m, 2H), 1.83-1.74 (m, 1H), 1.74-1.61 (m, 3H), 1.59-1.43 (m, 2H), 1.36-1.29 (m, 1H), 1.12 (d, J=6.5 Hz, 3H).

11. rac-N-(1-((1s,4s)-3'H-spiro[cyclohexane-1,1'-isobenzofuran]-4-yl)ethyl)-4-chlorobenzamide A reaction vial was charged with rac-1-((s,4s)-3'H-spiro[cyclohexane-1,1'-isobenzofuran]-4-yl)ethanamine (14 mg, 0.061 mmol) in DMF (0.5 mL). 4-Chlorobenzoic acid (11.37 mg, 0.073 mmol) and triethylamine (25.3 µl, 0.182 mmol) were added followed by BOP (34.8 mg, 0.079 mmol). After stirring overnight, the reaction was diluted with DMF (1.5 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 19 minutes, then a 5-minute hold at 100% B; Flow: 20 mL/min. Fractions containing the desired product were combined and dried via centrifugal evaporation to give rac-N-(1-((1s,4s)-3'H-spiro[cyclohexane-1,1'-isobenzofuran]-4-yl)ethyl)-4-chlorobenzamide (11.1 mg, 0.029 mmol, 47%). $^1$H NMR (500 MHz, DMSO-d$_6$) δ 8.31 (br d, J=8.5 Hz, 1H), 7.88 (br d, J=8.3 Hz, 2H), 7.53 (d, J=8.3 Hz, 2H), 7.24 (s, 3H), 7.20 (br s, 1H), 4.93 (s, 2H), 3.97-3.84 (m, 1H), 1.77-1.52 (m, 7H), 1.41 (br d, J=8.8 Hz, 2H), 1.15 (br d, J=6.7 Hz, 3H). LC-MS Anal. Calc'd for C$_{22}$H$_{24}$ClNO$_2$ 369.15, found [M+H] 370.1, T$_r$=2.05 min (Method A).

Example 12 rac-(1R,3S)—N-(1-((1S,4s)-3'H-spiro[cyclohexane-1,1'-isobenzofuran]-4-yl)ethyl)adamantane-1-carboxamide

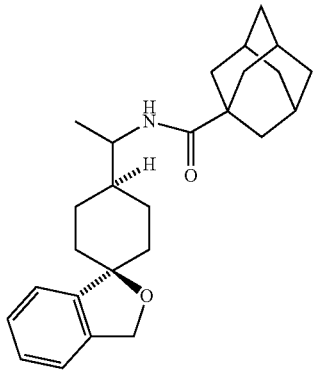 [SMILES: CC(NC(=O)C12CC3CC(CC(C3)C1)C2)[C@H]1CC[C@]2(CC1)OCc1ccccc12]

A reaction vial was charged with rac-1-((1s,4s)-3'H-spiro[cyclohexane-1,1'-isobenzofuran]-4-yl)ethanamine (14 mg, 0.061 mmol) (Intermediate 11A) in DMF (0.5 mL). (3r,5r,7r)-Adamantane-1-carboxylic acid (10.91 mg, 0.061 mmol) and triethylamine (25.3 µl, 0.182 mmol) were added followed by BOP (34.8 mg, 0.079 mmol). The reaction was then stirred overnight. The sample was then diluted with DMF (1.5 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 25 minutes, then a 5-minute hold at 100% B; Flow: 20 mL/min. Fractions containing the desired product were combined and dried via centrifugal evaporation to give rac-(1R,3S)—N-(1-((1S,4s)-3'H-spiro[cyclohexane-1,1'-isobenzofuran]-4-yl)ethyl)adamantane-1-carboxamide (13.4 mg, 0.034 mmol, 56%). $^1$H NMR (500 MHz, DMSO-d$_6$) δ 7.24 (d, J=2.4 Hz, 3H), 7.20-7.15 (m, 1H), 7.01 (br d, J=8.9 Hz, 1H), 4.93 (s, 2H), 3.72-3.60 (m, 1H), 1.95 (br s, 3H), 1.77 (d, J=2.1 Hz, 6H), 1.71-1.55 (m, 12H), 1.45 (br d, J=7.6 Hz, 1H), 1.39-1.24 (m, 2H), 1.02 (d, J=6.7 Hz, 3H). LC-MS Anal. Calc'd for C$_{26}$H$_{35}$NO$_2$ 393.27, found [M+H] 394.3, T$_r$=2.54 min (Method A).

Example 13 rac-N-(1-((1s,4s)-3'H-Spiro[cyclohexane-1,1'-isobenzofuran]-4-yl)ethyl)-4-chlorobicyclo[2.2.2]octane-1-carboxamide

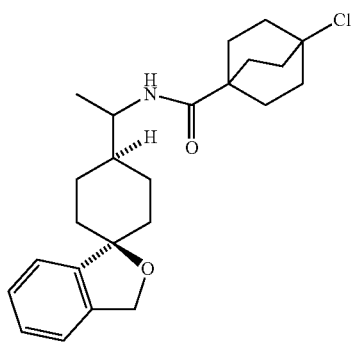 [SMILES: CC(NC(=O)C12CCC(Cl)(CC1)CC2)[C@H]1CC[C@]2(CC1)OCc1ccccc12]

A vial was charged with rac-1-((1s,4s)-3'H-spiro[cyclohexane-1,1'-isobenzofuran]-4-yl)ethanamine (14 mg, 0.061 mmol) in DMF (0.5 mL). 4-Chlorobicyclo[2.2.2]octane-1-carboxylic acid (11.42 mg, 0.061 mmol), triethylamine (25.3 µl, 0.182 mmol) and BOP (34.8 mg, 0.079 mmol) were then added and stirring continued overnight. The reaction was then diluted with DMF (1.5 mL). The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 45-90% B over 22 minutes, then a 5-minute hold at 100% B; Flow: 20 mL/min. Fractions containing the desired product were combined and dried via centrifugal evaporation to give rac-N-(1-((1s,4s)-3'H-spiro[cyclohexane-1,1'-isobenzofuran]-4-yl)ethyl)-4-chlorobicyclo[2.2.2]octane-1-carboxamide (12.9 mg, 0.032 mmol, 53%). $^1$H NMR (500 MHz, DMSO-$d_6$) δ 7.24 (s, 3H), 7.19 (br s, 1H), 7.13 (br d, J=8.6 Hz, 1H), 4.93 (s, 2H), 3.69-3.56 (m, 1H), 2.06-1.94 (m, 6H), 1.90-1.76 (m, 6H), 1.71-1.53 (m, 6H), 1.41 (br s, 1H), 1.37-1.24 (m, 2H), 1.00 (br d, J=6.7 Hz, 3H). LC-MS Anal. Calc'd for $C_{24}H_{32}ClNO_2$ 401.21, found [M+H] 402.2, $T_r$=2.12 min (Method A).

Example 14 rac-N-(4-Chlorophenyl)-2-((1'r,4'r)-2H-spiro[benzofuran-3,1'-cyclohexan]-4'-yl)propanamide

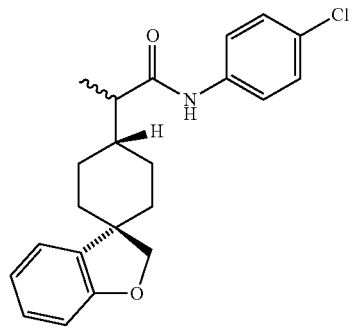 [SMILES: CC(C(=O)Nc1ccc(Cl)cc1)[C@H]1CC[C@@]2(CC1)COc1ccccc12]

14A. Methyl 1,4-dioxaspiro[4.5]dec-7-ene-8-carboxylate

A sealed tube was charged with (E)-((4-methoxybuta-1,3-dien-2-yl)oxy)trimethylsilane (4.45 g, 25.8 mmol) in benzene (25 mL). Nitrogen was bubbled through the solution for a few minutes. Methyl acrylate (4.65 ml, 51.7 mmol) was then added and the tube was sealed and heated to 85° C. After two days, the cooled reaction was treated with ethylene glycol (2.88 ml, 51.7 mmol) and p-toluenesulfonic acid monohydrate (0.246 g, 1.291 mmol). The reaction was warmed to 80° C. for 3 hours. The cooled reaction was transferred to a separatory funnel and partitioned between ether and saturated sodium bicarbonate solution. The organic phase was washed with water and brine. After drying over magnesium sulfate, filtration and evaporation, the crude material was purified on a flash silica gel column eluting with 20-25% ethyl acetate in hexanes. Evaporation provided methyl 1,4-dioxaspiro[4.5]dec-7-ene-8-carboxylate (2.74 g, 13.82 mmol, 53.5% yield) as a yellow liquid. $^1$H NMR (400 MHz, CHLOROFORM-d) δ 6.87 (tt, J=3.8, 1.8 Hz, 1H), 3.99 (s, 4H), 3.73 (s, 3H), 2.53 (tq, J=6.6, 2.1 Hz, 2H), 2.46-2.41 (m, 2H), 1.79 (t, J=6.6 Hz, 2H).

14B. 1,4-Dioxaspiro[4.5]dec-7-en-8-ylmethanol

Methyl 1,4-dioxaspiro[4.5]dec-7-ene-8-carboxylate (2.74 g, 13.82 mmol) was dissolved in dry methylene chloride (25 mL) under nitrogen. The reaction was cooled in a dry ice acetone bath when a solution of DIBAL-H (34.6 ml, 34.6 mmol) (1 M in methylene chloride) was added dropwise. After ca. 1 hour, the flask was briefly warmed in the palm of a hand and then recooled. Excess reagent was quenched with methanol (0.5 mL). A saturated solution of sodium potassium tartrate (10 mL) was added and stirring continued until the emulsion of aluminum salts had clarified. The reaction was transferred to a separatory funnel and extracted with methylene chloride. The organic phase was washed with water and brine. Drying over magnesium sulfate, filtration and evaporation provided 1,4-dioxaspiro[4.5]dec-7-en-8-ylmethanol (2.25 g, 13.22 mmol, 96% yield) as a colorless liquid. $^1$H NMR (400 MHz, CHLOROFORM-d) δ 5.75-5.44 (m, 1H), 4.04 (s, 2H), 3.99 (s, 4H), 2.34-2.22 (m, 4H), 1.81 (t, J=6.5 Hz, 2H).

14C. 8-((2-Bromophenoxy)methyl)-1,4-dioxaspiro[4.5]dec-7-ene 1,4-Dioxaspiro[4.5]dec-7-en-8-ylmethanol (1.55 g, 9.11 mmol) was dissolved in THF (20 mL) under nitrogen. Triphenylphosphine (3.58 g, 13.66 mmol) and 2-bromophenol (1.267 ml, 10.93 mmol) were added and stirred until dissolved. The reaction was cooled in an ice bath. DIAD (2.66 ml, 13.66 mmol) was added dropwise with gradual warming to RT. Upon completion, the reaction was applied to a 120 g Isco silica gel column and eluted with 0-50% ethyl acetate in hexanes. Evaporation of the product containing fractions gave 8-((2-bromophenoxy)methyl)-1,4-dioxaspiro[4.5]dec-7-ene (2.37 g, 7.29 mmol, 80% yield) as a colorless oil. $^1$H NMR (400 MHz, CHLOROFORM-d) δ 7.55 (dd, J=7.9, 1.7 Hz, 1H), 7.28-7.23 (m, 1H), 6.92 (dd, J=8.3, 1.3 Hz, 1H), 6.85 (td, J=7.6, 1.5 Hz, 1H), 5.81 (td, J=3.5, 1.9 Hz, 1H), 4.51 (s, 2H), 4.02 (s, 4H), 2.46-2.34 (m, 4H), 1.86 (t, J=6.5 Hz, 2H).

14D. 2H-Dispiro[benzofuran-3,1'-cyclohexane-4',2''-[1,3]dioxolane]

8-((2-bromophenoxy)methyl)-1,4-dioxaspiro[4.5]dec-7-ene (2.37 g, 7.29 mmol) was dissolved in toluene (50 mL).

The solution was subjected to three cycles of vacuum/nitrogen purge. Tri-n-butyltin hydride (2.335 ml, 8.75 mmol) and AIBN (0.120 g, 0.729 mmol) were added and the reaction was subjected to three additional cycles of vacuum/nitrogen purge. The vessel was then warmed to 100° C. for an hour. The cooled reaction was partially evaporated and applied to a flash silica gel column (3:1 hexanes/ethyl acetate). Evaporation of the product containing fractions gave 2H-dispiro[benzofuran-3,1'-cyclohexane-4',2''-[1,3]dioxolane](1.37 g, 5.56 mmol, 76% yield) as a crystalline solid. $^1$H NMR (400 MHz, CHLOROFORM-d) δ 7.18 (dd, J=7.3, 1.0 Hz, 1H), 7.13 (td, J=7.7, 1.3 Hz, 1H), 6.87 (td, J=7.4, 0.9 Hz, 1H), 6.79 (d, J=7.9 Hz, 1H), 4.38 (s, 2H), 4.02-3.97 (m, 4H), 2.07-1.95 (m, 2H), 1.89-1.75 (m, 4H), 1.71-1.59 (m, 2H), 0.92 (t, J=7.3 Hz, 1H).

14E. 2H-spiro[benzofuran-3,1'-cyclohexan]-4'-one 2H-dispiro[benzofuran-3,1'-cyclohexane-4',2''-[1,3]dioxolane] (1.37 g, 5.56 mmol) was dissolved in THF-water-acetic acid (3:2:2, 70 mL). The flask was sealed and warmed to 55° C. Heating was continued for two days. The cooled reaction was diluted with ether and carefully washed with saturated sodium bicarbonate solution. The organic phase was then washed with brine. Drying over magnesium sulfate, filtration and evaporation provided the crude product. Residual acetic acid was removed by azeotropic distillation with toluene. This material was crystallized from hot ethyl acetate Filtration provided 2H-spiro[benzofuran-3,1'-cyclohexan]-4'-one (629 mg, 3.11 mmol, 55.9% yield) as a colorless solid. A second crop of product was also obtained (109 mg, 66% yield). $^1$H NMR (400 MHz, CHLOROFORM-d) δ 7.21 (td, J=7.8, 1.3 Hz, 1H), 7.17 (dd, J=7.5, 0.9 Hz, 1H), 6.94 (td, J=7.4, 0.9 Hz, 1H), 6.88 (d, J=8.1 Hz, 1H), 4.58 (s, 2H), 2.62-2.43 (m, 4H), 2.26-2.09 (m, 4H).

14F. rac-(R,Z)-Ethyl 2-(2H-spiro[benzofuran-3,1'-cyclohexan]-4'-ylidene)propanoate A two neck flask was charged with sodium hydride (198 mg, 4.95 mmol) under nitrogen. THF (10 mL) was added and the reaction cooled in an ice bath. Triethyl 2-phosphonopropionate (1062 μl, 4.95 mmol) was added dropwise and stirring continued for 30 minutes. 2H-Spiro[benzofuran-3,1'-cyclohexan]-4'-one (626 mg, 3.10 mmol) was dissolved in THF (4 mL) with gentle heating and added rapidly. After stirring for a few minutes, the cooling bath was removed. The completed reaction was quenched with near saturated ammonium chloride. The quenched reaction was twice extracted with ethyl acetate. The combined organic layers were washed with brine. The organic phase was dried over magnesium sulfate, filtered and evaporated. The crude product was applied to a 120 g Isco silica gel column and eluted with 0-75% ethyl acetate in hexanes. Evaporation of the appropriate fractions gave rac-(R,Z)-ethyl 2-(2H-spiro[benzofuran-3,1'-cyclohexan]-4'-ylidene)propanoate (823 mg, 2.87 mmol, 93% yield). $^1$H NMR (400 MHz, CHLOROFORM-d) δ 7.21-7.08 (m, 2H), 6.89 (td, J=7.4, 0.9 Hz, 1H), 6.83 (d, J=7.9 Hz, 1H), 4.53-4.42 (m, 2H), 4.24 (q, J=7.1 Hz, 2H), 3.13-3.01 (m, 1H), 2.76-2.65 (m, 1H), 2.20-2.00 (m, 2H), 1.95 (s, 3H), 1.94-1.77 (m, 4H), 1.34 (t, J=7.2 Hz, 3H). $^{13}$C NMR (101 MHz, CHLOROFORM-d) δ 170.3, 159.4, 144.5, 134.8, 128.4, 122.9, 121.6, 120.6, 109.8, 80.9, 60.4, 46.38-46.32 (m, 1C), 37.6, 37.1, 28.7, 27.7, 15.3, 14.3.

14G. rac-2-((1'r,4'r)-2H-Spiro[benzofuran-3,1'-cyclohexan]-4'-yl)propanoic Acid and 14H. rac-2-((1's,4's)-2H-Spiro[benzofuran-3,1'-cyclohexan]-4'-yl)propanoic Acid A Parr bottle was charged with rac-(R,Z)-ethyl 2-(2H-spiro[benzofuran-3,1'-cyclohexan]-4'-ylidene)propanoate (823 mg, 2.87 mmol) in ethyl acetate (20 mL). 5% Rh/C (131 mg) was added and the bottle pressurized to 42 psi hydrogen. After 4 hours of reaction time, the reaction was filtered and evaporated. This material was carried into the next transformation without purification. The starting materials were dissolved in THF (3 mL) and water (1 mL) under nitrogen. sodium hydroxide (5555 μl, 5.56 mmol) (1 N) was then added. Ethanol was added dropwise until the reaction became homogeneous. The reaction was stirred overnight. The vessel was warmed to 55° C. and stirred overnight. The cooled reaction was neutralized with 1 N hydrochloric acid (5.6 mL). The organic solvents were removed by evaporation and the residue was extracted with ethyl acetate. The organic phase was washed with brine, dried over magnesium sulfate, filtered and evaporated. The crude material was purified by RP-HPLC (methanol-water gradient +0.1% TFA). Evaporation of the appropriate fractions gave rac-2-((1'r,4'r)-2H-spiro[benzofuran-3,1'-cyclohexan]-4'-yl)propanoic acid (16.6 mg, 0.064 mmol) and rac-2-((1's,4's)-2H-spiro[benzofuran-3,1'-cyclohexan]-4'-yl)propanoic acid (259 mg, 0.995 mmol).

14G: $^1$H NMR (500 MHz, BENZENE-d6) δ 7.27-7.22 (m, 1H), 7.06-7.00 (m, 1H), 6.92 (dd, J=7.9, 0.6 Hz, 1H), 6.80 (td, J=7.4, 1.1 Hz, 1H), 3.92-3.84 (m, 2H), 2.29 (quin, J=7.1 Hz, 1H), 1.69-1.63 (m, 1H), 1.61-1.54 (m, 1H), 1.54-1.45 (m, 2H), 1.41-1.23 (m, 3H), 1.16-1.02 (m, 2H), 1.01 (d, J=7.0 Hz, 3H). $^{13}$C NMR (126 MHz, BENZENE-d$_6$) δ 181.6, 160.6, 134.9, 128.4, 125.0, 120.1, 110.2, 83.6, 44.6, 43.5, 38.6, 35.0, 29.7, 26.3, 24.6, 14.1.

14H: $^1$H NMR (500 MHz, BENZENE-d$_6$) δ 7.03-6.99 (m, 1H), 6.90 (d, J=7.9 Hz, 1H), 6.89-6.86 (m, 1H), 6.85-6.81 (m, 1H), 4.06-4.01 (m, 2H), 2.01 (quin, J=7.1 Hz, 1H), 1.56-1.46 (m, 2H), 1.46-1.38 (m, 2H), 1.37-1.31 (m, 2H), 1.31-1.24 (m, 1H), 1.01 (d, J=7.0 Hz, 1H), 0.94 (d, J=7.0 Hz, 3H), 0.74 (qd, J=13.2, 3.4 Hz, 1H), 0.54 (qd, J=13.3, 4.1 Hz, 1H). $^{13}$C NMR (126 MHz, BENZENE-d$_6$) δ 182.2, 159.8, 135.8, 128.4, 122.5, 120.4, 109.8, 80.0, 45.6, 44.8, 39.1, 36.3, 36.2, 27.7, 25.9, 13.6.

Example 14

A flask was charged with rac-2-((1'r,4'r)-2H-spiro[benzofuran-3,1'-cyclohexan]-4'-yl)propanoic acid (44.3 mg, 0.170 mmol) in DMF (500 mL). The reaction was initiated with the sequential addition of 4-chloroaniline (32.6 mg, 0.255 mmol), triethylamine (71.2 μl, 0.511 mmol) and BOP (113 mg, 0.255 mmol). A small amount of DMAP (6 mg) was added and the flask was warmed to 55° C. overnight. The cooled reaction was diluted with DMF (1.0 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-90% B over 19 minutes, then a 7-minute hold at 100% B; Flow: 20 mL/min. Fractions containing the desired product were combined and dried via centrifugal evaporation to give rac-N-(4-chlorophenyl)-2-((1'r,4'r)-2H-spiro[benzofuran-3,1'-cyclohexan]-4'-yl)propanamide (37 mg, 0.098 mmol, 58%). $^1$H NMR (500 MHz, DMSO-d$_6$) δ 10.11 (s, 1H), 7.63 (br d, J=8.7 Hz, 2H), 7.40 (br d, J=7.4 Hz, 1H), 7.35 (br d, J=8.7 Hz, 2H), 7.18-7.04 (m, 1H), 6.83 (t, J=7.4 Hz, 1H), 6.75 (d, J=7.9 Hz, 1H), 4.18 (q, J=8.6 Hz, 2H), 1.84-1.59 (m, 4H), 1.58-1.38 (m, 5H), 1.12 (br d, J=6.6 Hz, 3H). LC-MS Anal. Calc'd for C$_{22}$H$_{24}$ClNO$_2$ 369.15, found [M+H] 370.2, T$_r$=2.28 min (Method A).

Examples 15 and 16

(S)—N-(4-Chlorophenyl)-2-((1'S,4'r)-2H-spiro[benzofuran-3,1'-cyclohexan]-4'-yl)propanamide and (R)—N-(4-Chlorophenyl)-2-((1'R,4'r)-2H-spiro[benzofuran-3,1'-cyclohexan]-4'-yl)propanamide

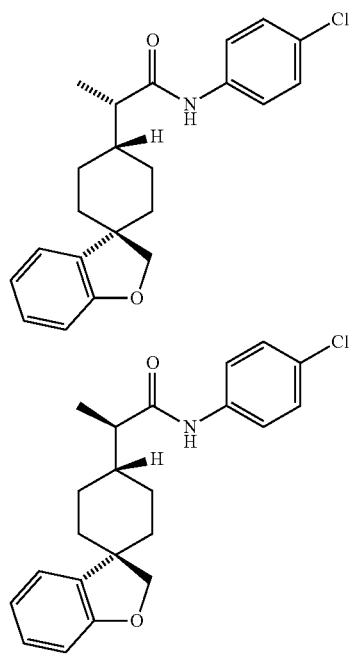

An approximately 35 mg sample of Example 14 was resolved into enantiomers using chiral SFC under the following conditions: Column: Chiralpak AD, 30×250 mm, 5 micron, Flow Rate: 100 mL/min, Oven Temperature: 40 C, BPR Setting: 120 bar, UV wavelength: 220 nm, Mobile Phase: 80% CO2/20%, Methanol-0.1% DEA (isocratic), Injection: 3000 uL of 35 mg/3.0 mL MeOH. Evaporation of the product containing fractions provided En-1 (12.1 mg) and En-2 (12.1 mg).

En-1. $^1$H NMR (500 MHz, DMSO-d$_6$) δ 10.09 (s, 1H), 7.65 (br d, J=8.4 Hz, 2H), 7.40 (br d, J=7.3 Hz, 1H), 7.35 (br d, J=8.4 Hz, 2H), 7.12 (br t, J=7.6 Hz, 1H), 6.84 (br t, J=7.3 Hz, 1H), 6.76 (br d, J=7.8 Hz, 1H), 4.19 (q, J=8.8 Hz, 2H), 1.86-1.61 (m, 4H), 1.59-1.37 (m, 5H), 1.13 (br d, J=6.6 Hz, 3H). LC-MS Anal. Calc'd for C$_{22}$H$_{24}$ClNO$_2$ 369.15, found [M+H] 370.1, T$_r$=2.26 min (Method A). Chiral HPLC: T$_r$=3.50 (100%) (Method D).

En-2: $^1$H NMR (500 MHz, DMSO-d$_6$) δ 10.09 (s, 1H), 7.65 (br d, J=8.4 Hz, 2H), 7.40 (br d, J=7.2 Hz, 1H), 7.35 (br d, J=8.2 Hz, 2H), 7.15-7.09 (m, 1H), 6.84 (br t, J=7.3 Hz, 1H), 6.76 (br d, J=7.9 Hz, 1H), 4.19 (q, J=8.6 Hz, 2H), 1.85-1.61 (m, 4H), 1.59-1.39 (m, 5H), 1.13 (br d, J=6.5 Hz, 3H). LC-MS Anal. Calc'd for C$_{22}$H$_{24}$ClNO$_2$ 369.15, found [M+H] 369.8, T$_r$=2.26 min (Method A). Chiral HPLC: T$_r$=4.57 (95.2%) (Method D).

Example 17 rac-N-(1-((1'r,4'r)-2H-Spiro[benzofuran-3,1'-cyclohexan]-4'-yl)ethyl)-4-chlorobenzamide

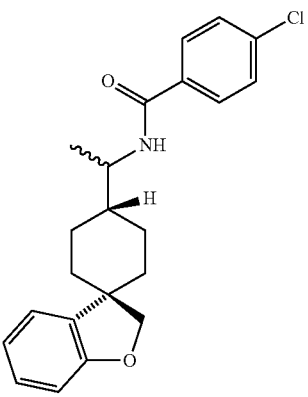

rac-2-((1'r,4'r)-2H-Spiro[benzofuran-3,1'-cyclohexan]-4'-yl)propanoic acid (45 mg, 0.173 mmol) (Intermediate 14G) was dissolved in dioxane (1 mL). Triethylamine (72.3 μl, 0.519 mmol) and diphenylphosphoryl azide (44.7 μl, 0.207 mmol) were then added. The flask was evacuated and flushed with nitrogen three times. The reaction was then sealed and heated to 80° C. for 2 hours. The cooled reaction was then treated with a 1 N solution of lithium hydroxide (519 μl, 0.519 mmol) and stirring was continued for 2 hours. The reaction was the filtered and transferred to a separatory funnel. The product was partitioned between ethyl acetate and a small amount of water. The aqueous layer was extracted with another portion of ethyl acetate. The combined organic layers were washed with brine. Drying over magnesium sulfate, filtration and evaporation provided 76 mg of the crude product. This material was used directly in the next step. rac-1-((1'r,4'r)-2H-Spiro[benzofuran-3,1'-cyclohexan]-4'-yl)ethanamine (40 mg, 0.173 mmol) was dissolved in DMF (1.0 mL). Triethylamine (72.3 μl, 0.519 mmol) and 4-chlorobenzoic acid (32.5 mg, 0.207 mmol) were then added. The reaction was initiated with the addition of BOP (92 mg, 0.207 mmol). Upon completion, the reaction was diluted with DMF (1 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 19 minutes, then a 5-minute hold at 100% B; Flow: 20 mL/min. Fractions containing the desired product were combined and dried via centrifugal evaporation to give rac-N-(1-((1'r,4'r)-2H-spiro[benzofuran-3,1'-cyclohexan]-4'-yl)ethyl)-4-chlorobenzamide (37.4 mg, 0.10 mmol). $^1$H NMR (500 MHz, DMSO-d$_6$) δ 8.32 (br d, J=8.5 Hz, 1H), 7.89 (br d, J=8.5 Hz, 2H), 7.54 (br d, J=8.2 Hz, 2H), 7.35 (br d, J=7.3 Hz, 1H), 7.13-7.07 (m, 1H), 6.81 (t, J=7.3 Hz, 1H), 6.76 (d, J=7.9 Hz, 1H), 4.19 (s, 3H), 1.80 (br t, J=13.9 Hz, 2H), 1.70-1.43 (m, 7H), 1.19 (br d, J=6.7 Hz, 3H). LC-MS Anal. Calc'd for C$_{22}$H$_{24}$ClNO$_2$ 369.15, found [M+H] 370.1, T$_r$=2.14 min (Method A).

Examples 18 and 19

N—((R)-1-((1'R,4'r)-2H-Spiro[benzofuran-3,1'-cyclohexan]-4'-yl)ethyl)-4-chlorobenzamide and N—((S)-1-((1'S,4'r)-2H-Spiro[benzofuran-3,1'-cyclohexan]-4'-yl)ethyl)-4-chlorobenzamide

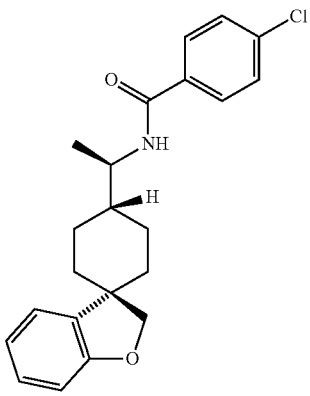

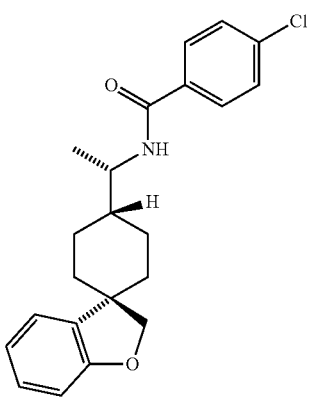 [SMILES: CC(NC(=O)c1ccc(Cl)cc1)[C@H]1CC[C@@]2(CC1)COc1ccccc12]

An approximately 36 mg sample of Example 17 was resolved into enantiomers using chiral SFC under the following conditions: Column: Chiralpak AD, 30×250 mm, 5 micron, Flow Rate: 100 mL/min, Oven Temperature: 40 C, BPR Setting: 120 bar, UV wavelength: 220 nm, Mobile Phase: 75% CO2/25%, Isopropanol-0.1% DEA (isocratic), Injection: 1000 uL of 36 mg/3.0 mL MeOH. Evaporation of the product containing fractions provided En-3 (14.7 mg) and En-4 (14.5 mg).

En-3. $^1$H NMR (500 MHz, DMSO-$d_6$) δ 8.35 (br d, J=8.4 Hz, 1H), 7.88 (br d, J=7.7 Hz, 2H), 7.55 (br d, J=7.7 Hz, 2H), 7.35 (br d, J=7.3 Hz, 1H), 7.15-6.98 (m, 1H), 6.81 (br t, J=7.3 Hz, 1H), 6.76 (br d, J=7.8 Hz, 1H), 4.19 (s and an obscured resonance, 3H), 1.85-1.73 (m, 2H), 1.70 [M+H] 370.1, $T_r$=2.15 min (Method A). Chiral HPLC: $T_r$=2.94 (100%) (Method E).

En-4. $^1$H NMR (500 MHz, DMSO-$d_6$) δ 8.35 (br d, J=8.3 Hz, 1H), 7.88 (br d, J=7.7 Hz, 2H), 7.55 (br d, J=7.6 Hz, 2H), 7.35 (br d, J=7.3 Hz, 1H), 7.16-7.05 (m, 1H), 6.81 (br t, J=7.4 Hz, 1H), 6.76 (br d, J=7.8 Hz, 1H), 4.19 (s and an obscured resonance, 3H), 1.79 (br t, J=13.8 Hz, 2H), 1.70-1.43 (m, 6H), 1.19 (br d, J=6.4 Hz, 3H). LC-MS Anal. Calc'd for $C_{22}H_{24}ClNO_2$ 369.15, found [M+H] 369.9, $T_r$=2.16 min (Method A). Chiral HPLC: $T_r$=4.26 (99.8%) (Method E).

Example 20 rac-N-(4-Chlorophenyl)-2-((1's,4's)-2H-spiro[benzofuran-3,1'-cyclohexan]-4'-yl)propanamide

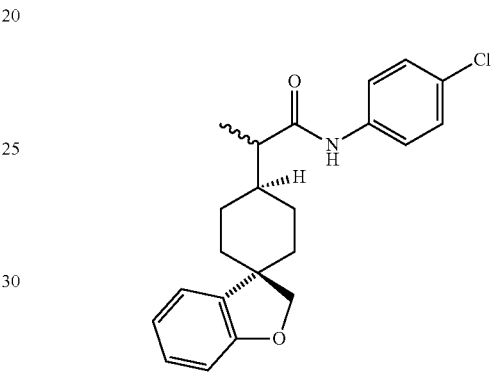

rac-2-((1's,4's)-2H-Spiro[benzofuran-3,1'-cyclohexan]-4'-yl)propanoic acid (19.4 mg, 0.075 mmol) (Intermediate 14H) and 4-chloroaniline (11.41 mg, 0.089 mmol) were dissolved in DMF (200 uL). Hunig's Base (39.0 µl, 0.224 mmol) and HATU (34.0 mg, 0.089 mmol) were then added. After stirring for 20 minutes, the reaction was warmed to 60° C. Heating was continued for 3 hours. The cooled reaction was diluted with DMF (1 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 20 minutes, then a 3-minute hold at 100% B; Flow: 20 mL/min. Fractions containing the desired product were combined and dried via centrifugal evaporation to give rac-N-(4-chlorophenyl)-2-((1's,4's)-2H-spiro[benzofuran-3,1'-cyclohexan]-4'-yl)propanamide (18.7 mg, 0.051 mmol, 68%). $^1$H NMR (500 MHz, DMSO-$d_6$) δ 10.01 (br s, 1H), 7.65 (br d, J=8.8 Hz, 2H), 7.35 (d, J=8.8 Hz, 2H), 7.17 (d, J=7.2 Hz, 1H), 7.08 (t, J=7.7 Hz, 1H), 6.83 (t, J=7.4 Hz, 1H), 6.73 (d, J=7.9 Hz, 1H), 4.43-4.21 (m, 2H), 2.24 (br t, J=7.3 Hz, 1H), 1.84 (br d, J=13.2 Hz, 1H), 1.75-1.50 (m, 6H), 1.21-1.12 (m, 1H), 1.10 (br d, J=6.7 Hz, 3H), 1.05-0.94 (m, 1H). LC-MS Anal. Calc'd for $C_{22}H_{24}ClNO_2$ 369.15, found [M+H] 370.0, $T_r$=2.24 min (Method A).

Example 21 rac-N-(1-((1's,4's)-2H-Spiro[benzofuran-3,1'-cyclo-hexan]-4'-yl)ethyl)-4-chlorobenzamide

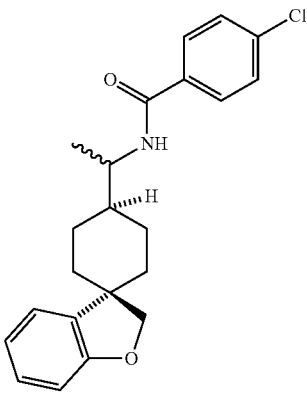 [SMILES: CC(NC(=O)c1ccc(Cl)cc1)[C@H]1CC[C@]2(CC1)COc1ccccc12]

rac-2-((1's,4's)-2H-Spiro[benzofuran-3,1'-cyclohexan]-4'-yl)propanoic acid (74 mg, 0.284 mmol) (Intermediate 14H) was dissolved in dioxane (1 mL). Triethylamine (119 µl, 0.853 mmol) and diphenylphosphoryl azide (73.5 µl, 0.341 mmol) were then added. The flask was evacuated and flushed with nitrogen three times. The reaction was then sealed and heated to 80° C. for 3 hours. The cooled reaction was treated with lithium hydroxide (853 µl, 0.853 mmol) solution (1 N) and stirred overnight. The reaction was partitioned between ether and water. The aqueous layer was further extracted twice with ether. The combined organic layers were washed with brine. Drying over magnesium sulfate, filtration and evaporation provided the crude product. This material was used without purification. A reaction vial was charged with rac-1-((1's,4's)-2H-spiro[benzofuran-3,1'-cyclohexan]-4'-yl)ethanamine (9.5 mg, 0.041 mmol) in DMF (0.5 mL). 4-Chlorobenzoic acid (9.64 mg, 0.062 mmol) and triethylamine (17.17 µl, 0.123 mmol) were added. Reaction was initiated with the addition of BOP (27.2 mg, 0.062 mmol). After stirring for a few hours, the reaction was diluted with DMF (1 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-90% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 50-75% B over 25 minutes, then a 2-minute hold at 75% B; Flow: 20 mL/min. Fractions containing the desired product were combined and dried via centrifugal evaporation to give rac-N-(1-((1's,4's)-2H-spiro[benzofuran-3,1'-cyclohexan]-4'-yl)ethyl)-4-chlorobenzamide (13.0 mg, 0.035 mmol, 86%). $^1$H NMR (500 MHz, DMSO-d$_6$) δ 8.33 (br d, J=8.4 Hz, 1H), 7.85 (br d, J=8.0 Hz, 2H), 7.52 (br d, J=7.9 Hz, 2H), 7.14 (br d, J=7.2 Hz, 1H), 7.08 (br t, J=7.6 Hz, 1H), 6.83 (br t, J=7.3 Hz, 1H), 6.73 (br d, J=7.9 Hz, 1H), 4.37-4.25 (m, 2H), 3.91-3.79 (m, 1H), 1.84-1.45 (m, 8H), 1.13 (br d, J=6.6 Hz, 3H), 1.10-0.97 (m, 2H). LC-MS Anal. Calc'd for C$_{22}$H$_{24}$ClNO$_2$ 369.15, found [M+H] 370.2, T$_r$=2.17 min (Method A).

Examples 22 and 23

2-((R)-1-((3R,4'r)-2H-spiro[benzofuran-3,1'-cyclohexan]-4'-yl)ethyl)-6-chloro-1H-benzo[d]imidazole and 2-((S)-1-((3S,4'r)-2H-spiro[benzofuran-3,1'-cyclohexan]-4'-yl)ethyl)-6-chloro-1H-benzo[d]imidazole

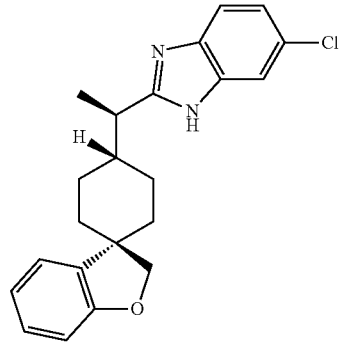

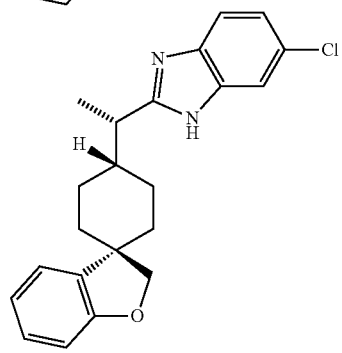

2-((1'r,4'r)-2H-Spiro[benzofuran-3,1'-cyclohexan]-4'-yl)propanoic acid (25 mg, 0.096 mmol) (Intermediate 14G) was dissolved in thionyl chloride (70.1 µl, 0.960 mmol) and DMF (3.72 µl, 0.048 mmol) was added. Reaction was stirred at room temperature for 1 hour. The reaction was then concentrated in vacuo, taken up in toluene, concentrated again and placed under high vacuum. After 15 minutes, the crude acyl chloride was taken up in acetonitrile (960 µl) and added to a solution of 4-chlorobenzene-1,2-diamine (27.4 mg, 0.192 mmol) in acetonitrile (960 µl) and triethylamine (66.9 µl, 0.480 mmol) at 0° C. The reaction was then allowed to warm to room temperature. After one hour, the reaction was diluted with water and extracted with ethyl acetate. The organic phase was dried with sodium sulfate, filtered and concentrated in vacuo. The crude residue was taken up in phosphorus oxychloride (90 µl, 0.960 mmol). The reaction was heated to 90° C. After an hour, the reaction was quenched into cold (over ice) 1N NaOH and extracted with ethyl acetate. The organic phase was dried with sodium sulfate, filtered and concentrated. The crude residue was taken up in DMF and filtered. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-60% B over 20 minutes, then a 5-minute hold at 100% B; Flow: 20 mL/min. Fractions containing the desired product were combined and dried via centrifugal evaporation. This sample was resolved into enantiomers using chiral SFC using a Chiralpak AD column 80% CO2/20%, isopropanol-0.1% DEA (isocratic). Evaporation of the appropriate fractions gave En-5 (5.1 mg, 0.014 mmol, 14.52% yield) and En-6 (5.3 mg, 0.014 mmol, 15.08% yield).

En-5. $^1$H NMR (500 MHz, DMSO-$d_6$) δ 7.59 (s, 1H), 7.55 (br d, J=8.5 Hz, 1H), 7.48 (s, 1H), 7.45 (br d, J=8.5 Hz, 1H), 7.30 (br d, J=7.0 Hz, 1H), 7.15 (br t, J=8.7 Hz, 1H), 7.09 (br t, J=7.6 Hz, 1H), 6.82-6.68 (m, 2H), 4.22-4.09 (m, 2H), 3.20-3.05 (m, 1H), 1.91-1.59 (m, 5H), 1.53 (br d, J=10.1 Hz, 1H), 1.45-1.29 (m, 6H) (presence of benzimidazole tautomers is evident in the spectrum). LC-MS Anal. Calc'd for $C_{22}H_{22}ClN_2O$, 366.14, found [M+H] 367.0, $T_r$=1.51 min (Method A). Chiral HPLC: $T_r$=3.63 (100%) (Chirapak AD, 80% CO2/20% isopropanol/0.1% DEA).

En-6. $^1$H NMR (500 MHz, DMSO-$d_6$) δ 7.59 (br s, 1H), 7.55 (br d, J=8.9 Hz, 1H), 7.48 (br s, 1H), 7.45 (br d, J=8.2 Hz, 1H), 7.30 (br d, J=7.0 Hz, 1H), 7.15 (br t, J=8.7 Hz, 1H), 7.11-7.02 (m, 1H), 6.80-6.69 (m, 2H), 4.21-4.10 (m, 2H), 3.21-3.06 (m, 1H), 1.94-1.58 (m, 5H), 1.52 (br t, J=9.3 Hz, 1H), 1.46-1.29 (m, 6H) (presence of benzimidazole tautomers is evident in the spectrum). LC-MS Anal. Calc'd for $C_{22}H_{22}ClN_2O$, 366.14, found [M+H] 367.1, $T_r$=1.51 min (Method A). Chiral HPLC: $T_r$=4.72 (98%) (Chirapak AD, 80% CO2/20% isopropanol/0.1% DEA).

Example 24 rac-2-(1-((1'r,4'r)-2H-Spiro[benzofuran-3,1'-cyclohexan]-4'-yl)ethyl)-6-chloro-1H-imidazo[4,5-b]pyridine TFA Salt

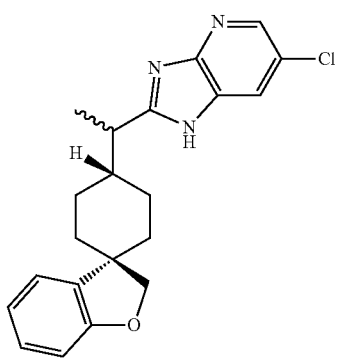 [SMILES: CC(c1nc2ncc(Cl)cc2[nH]1)[C@H]1CC[C@@]2(CC1)COc1ccccc12]

2-((1'r,4'r)-2H-spiro[benzofuran-3,1'-cyclohexan]-4'-yl) propanoic acid (25 mg, 0.096 mmol) was dissolved in thionyl chloride (70.1 μl, 0.960 mmol) and DMF (3.72 μl, 0.048 mmol) was added. The reaction was stirred at room temperature. After one hour, the reaction was concentrated in vacuo, taken up in toluene, concentrated again and placed under high vacuum. After 15 minutes, the crude acyl chloride was taken up in acetonitrile (960 μl) and added to a solution of 4-chlorobenzene-1,2-diamine (27.4 mg, 0.192 mmol) in acetonitrile (960 μl) and triethylamine (66.9 μl, 0.480 mmol) at 0° C. The reaction was then allowed to warm to room temperature. After 1 h, the reaction was diluted with water and extracted with ethyl acetate. The organic phase was dried with sodium sulfate, filtered and concentrated in vacuo. The crude residue was taken up in phosphorus oxychloride (90 μl, 0.960 mmol) and heated to 90° C. After one hour, the reaction was quenched into cold (over ice) TN NaOH and extracted with ethyl acetate. The organic layer was dried with sodium sulfate, filtered and concentrated. The crude residue was taken up in DMF and filtered. The crude material was purified via preparative LC/MS with the following conditions: Column: Xbridge C18, 19×200 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: 20-60% B over 20 minutes, then a 5-minute hold at 100% B; Flow: 20 mL/min. Fractions containing the desired product were combined and dried via centrifugal evaporation to give rac-2-(1-((1'r,4'r)-2H-spiro[benzofuran-3,1'-cyclohexan]-4'-yl)ethyl)-6-chloro-1H-imidazo[4,5-b]pyridine (15 mg) as its TFA salt. $^1$H NMR (500 MHz, DMSO-$d_6$) δ 8.34 (d, J=1.8 Hz, 1H), 8.11 (d, J=1.8 Hz, 1H), 7.33 (d, J=7.3 Hz, 1H), 7.23 (s, 1H), 7.12 (d, J=6.4 Hz, 1H), 7.11-7.06 (m, 1H), 7.03 (s, 1H), 6.79 (t, J=7.3 Hz, 1H), 6.75 (d, J=7.9 Hz, 1H), 4.23-4.11 (m, 2H), 3.30-3.17 (m, 1H), 1.89 (br s, 1H), 1.84-1.70 (m, 3H), 1.65 (br d, J=9.8 Hz, 1H), 1.58-1.50 (m, 1H), 1.48-1.34 (m, 6H). LC-MS Anal. Calc'd for $C_{21}H_{21}ClN_3O$, 367.15, found [M+H] 368.1, $T_r$=1.59 min (Method A).

Example 25 and 26

2-((R)-1-((3R,4'r)-2H-spiro[benzofuran-3,1'-cyclohexan]-4'-yl)ethyl)-6-chloro-1H-imidazo[4,5-b]pyridine and 2-((S)-1-((3S,4'r)-2H-spiro[benzofuran-3,1'-cyclohexan]-4'-yl)ethyl)-6-chloro-1H-imidazo[4,5-b]pyridine

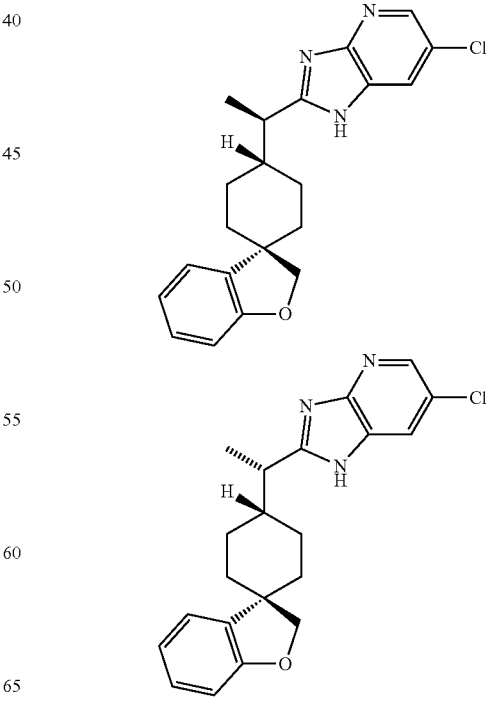

The compound of example 24 (15 mg) was resolved into enantiomers using chiral SFC using a Chiralpak OJ column 85% CO2/15%, methanol-0.1% DEA (isocratic). Evaporation of the appropriate fractions gave En-7 (3.5 mg) and En-8 (3.6 mg).

En-7. $^1$H NMR (500 MHz, DMSO-$d_6$) δ 8.26 (br s, 1H), 8.12-7.92 (m, 1H), 7.31 (br d, J=7.0 Hz, 1H), 7.15-7.04 (m, 1H), 6.77 (br t, J=7.3 Hz, 1H), 6.74 (br d, J=7.9 Hz, 1H), 4.16 (q, J=8.5 Hz, 2H), 3.17 (br d, J=5.2 Hz, 1H), 1.89 (br d, J=15.3 Hz, 1H), 1.81-1.68 (m, 3H), 1.63 (br d, J=9.8 Hz, 1H), 1.54 (br d, J=9.5 Hz, 1H), 1.57-1.49 (m, 1H), 1.46-1.29 (m, 6H). LC-MS Anal. Calc'd for $C_{21}H_{21}ClN_3O$, 367.15, found [M+H] 368.1, $T_r$=1.60 min (Method A). Chiral HPLC: $T_r$=2.17 (100%) (Chirapak OJ, 85% CO2/15% methanol/0.1% DEA).

En-8. $^1$H NMR (500 MHz, DMSO-$d_6$) δ 8.25 (br s, 1H), 8.12-7.90 (m, 1H), 7.31 (br d, J=7.0 Hz, 1H), 7.17-7.01 (m, 1H), 6.77 (br t, J=7.3 Hz, 1H), 6.74 (br d, J=7.9 Hz, 1H), 4.20-4.10 (m, 2H), 3.16 (br s, 1H), 1.89 (br d, J=18.3 Hz, 1H), 1.82-1.68 (m, 3H), 1.63 (br d, J=9.5 Hz, 1H), 1.53 (br t, J=9.6 Hz, 1H), 1.46-1.28 (m, 6H). LC-MS Anal. Calc'd for $C_{21}H_{21}ClN_3O$, 367.15, found [M+H] 368.1, $T_r$=1.52 min (Method A). Chiral HPLC: $T_r$=4.72 (98%) (Chirapak AD, 80% CO2/20% methanol/0.1% DEA).

Example 27 rac-N-(1-((1's,4's)-2H-Spiro[benzofuran-3,1'-cyclohexan]-4'-yl)ethyl)-4-cyanobenzamide

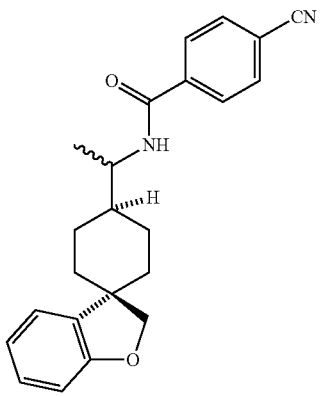 [SMILES: CC(NC(=O)c1ccc(C#N)cc1)[C@H]1CC[C@]2(CC1)COc1ccccc12]

A reaction vial was charged with rac-1-((1's,4's)-2H-spiro[benzofuran-3,1'-cyclohexan]-4'-yl)ethanamine (9.5 mg, 0.041 mmol)(from the intermediate in Example 21) in DMF (0.5 mL). 4-Cyanobenzoic acid (9.06 mg, 0.062 mmol) and triethylamine (17.17 µl, 0.123 mmol) were added. Reaction was initiated with the addition of BOP (27.2 mg, 0.062 mmol). After stirring overnight, the sample was diluted with DMF (1 mL). The crude material was purified via preparative LC/MS with the following conditions: Column: Xbridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 23 minutes, then a 5-minute hold at 100% B; Flow: 20 mL/min. Fractions containing the desired product were combined and dried via centrifugal evaporation to give rac-N-(1-((1's,4's)-2H-spiro[benzofuran-3,1'-cyclohexan]-4'-yl)ethyl)-4-cyanobenzamide (10.9 mg, 0.030 mmol, 74%). $^1$H NMR (500 MHz, DMSO-$d_6$) δ 8.49 (br d, J=8.2 Hz, 1H), 8.05-7.87 (m, 4H), 7.15 (br d, J=7.1 Hz, 1H), 7.08 (br t, J=7.5 Hz, 1H), 6.84 (br t, J=7.2 Hz, 1H), 6.74 (br d, J=7.9 Hz, 1H), 4.42-4.25 (m, 2H), 3.93-3.80 (m, 1H), 1.84-1.45 (m, 7H), 1.15 (br d, J=6.4 Hz, 3H), 1.13-1.02 (m, 2H). LC-MS Anal. Calc'd for $C_{23}H_{24}N_2O_2$ 360.18, found [M+H] 361.0, $T_r$=2.00 min (Method A).

Example 28 rac-N—((1R,3S)-Adamantan-1-yl)-2-((1R,4r)-3'H-spiro[cyclohexane-1,1'-isobenzofuran]-4'-yl)propanamide

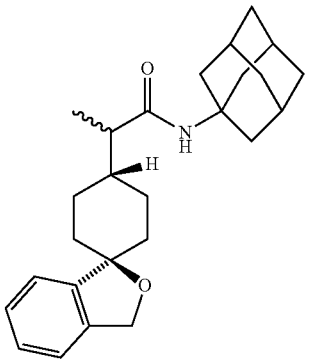 [SMILES: CC(C(=O)NC12CC3CC(CC(C3)C1)C2)[C@H]1CC[C@@]2(CC1)OCc1ccccc12]

A reaction vial was charged with rac-2-((1r,4r)-3'H-spiro[cyclohexane-1,1'-isobenzofuran]-4'-yl)propanoic acid (8.3 mg, 0.032 mmol) (Intermediate 4D) in DMF (250 uL). Reaction was initiated with the sequential addition of (3s,5s,7s)-adamantan-1-amine (4.82 mg, 0.032 mmol), triethylamine (13.33 µl, 0.096 mmol) and BOP (21.15 mg, 0.048 mmol). Upon reaction completion, the reaction was diluted with DMF (0.75 mL). The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation to give rac-N—((1R,3S)-adamantan-1-yl)-2-((1R,4r)-3'H-spiro[cyclohexane-1,1'-isobenzofuran]-4'-yl)propanamide (5 mg, 0.013 mmol, 40%). $^1$H NMR (500 MHz, DMSO-$d_6$) δ 7.41 (br d, J=6.4 Hz, 1H), 7.37 (s, 1H), 7.26 (s, 3H), 4.92 (s, 2H), 2.40 (br d, J=6.7 Hz, 1H), 2.04-1.37 (m, 22H), 0.97 (br d, J=6.6 Hz, 3H). LC-MS Anal. Calc'd for $C_{26}H_{35}NO_2$ 393.27, found [M+H] 394.3, $T_r$=2.35 min (Method A).

Example 29 rac-N-(4-Chlorophenyl)-2-((1'r,2R,4'R)-2-(hydroxymethyl)-7-methyl-2H-spiro[benzofuran-3,1'-cyclohexan]-4'-yl)acetamide

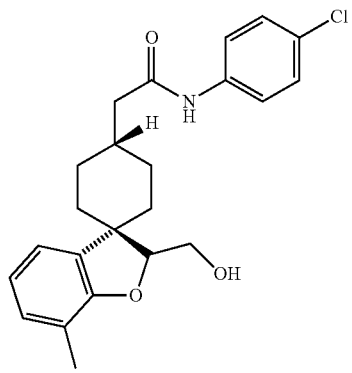

29A. Ethyl 2-(2-bromo-6-methylphenoxy)acetate

A three necked flask was equipped with a dropping funnel. The flask was charged with sodium hydride (1.283 g, 32.1 mmol)(60% dispersion in oil) and DMF (40 mL). The dropping funnel was charged with 2-bromo-6-methylphenol (5 g, 26.7 mmol) in DMF (5 mL). This solution was added dropwise and the reaction then stirred for 0.5 hour. The dropping funnel was then charged with ethyl 2-bromoacetate (3.26 ml, 29.4 mmol) in DMF (5 mL). This solution was added dropwise and the reaction stirred overnight. The reaction was then transferred to a separatory funnel and partitioned between ether and 1 N sodium hydroxide. The organic layer was further washed with water then brine. Drying over magnesium sulfate, filtration and evaporation provided the crude product. The crude product was applied to a 120 g Isco silica gel column and eluted with 0-25% ethyl acetate in hexanes. Evaporation of the product containing fractions provided ethyl 2-(2-bromo-6-methylphenoxy)acetate (4.7 g, 17.21 mmol, 64.4% yield) as a colorless liquid. $^1$H NMR (400 MHz, CHLOROFORM-d) δ 7.38 (dd, J=7.9, 1.0 Hz, 1H), 7.15-7.09 (m, 1H), 6.91 (t, J=7.8 Hz, 1H), 4.55 (s, 2H), 4.31 (q, J=7.2 Hz, 2H), 2.36 (s, 3H), 1.34 (t, J=7.2 Hz, 3H). $^{13}$C NMR (101 MHz, CHLOROFORM-d) δ 168.6, 153.7, 133.4, 131.2, 130.5, 125.8, 116.8, 69.3, 61.3, 16.7, 14.2.

29B. Ethyl 2-(2-bromo-6-methylphenoxy)-2-(8-hydroxy-1,4-dioxaspiro[4.5]decan-8-yl)acetate An oven dried 250 mL three neck flask was sealed under nitrogen. The flask was charged with lithium bis(trimethylsilyl)amide (34.4 ml, 34.4 mmol) (1 M in THF) and cooled in a dry ice-acetone bath. Ethyl 2-(2-bromo-6-methylphenoxy)acetate (4.7 g, 17.21 mmol) in THF (5 mL) was added dropwise. After 20 minutes, 1,4-dioxaspiro[4.5]decan-8-one (3.23 g, 20.65 mmol) in THF (5 mL) was added rapidly. After stirring for 0.5 hour, the reaction was quenched with saturated sodium bicarbonate solution and warmed to room temperature. The quenched reaction was extracted with ether. The organic phase was washed with 1 N hydrochloric acid, water and brine. The solution was dried over magnesium sulfate, filtered and evaporated. The crude product was applied to a 220 g Isco silica gel column and eluted with 0-10% methanol in methylene chloride. Evaporation of the product containing fractions gave ethyl 2-(2-bromo-6-methylphenoxy)-2-(8-hydroxy-1,4-dioxaspiro[4.5]decan-8-yl) acetate (3.05 g, 7.10 mmol, 41.3% yield) as a yellow oil. Although some impurities were evident in this material by $^1$H-NMR, it was carried forward into the next reaction.

29C. Ethyl 2-(2-bromo-6-methylphenoxy)-2-(1,4-dioxaspiro[4.5]dec-7-en-8-yl)acetate Ethyl 2-(2-bromo-6-methylphenoxy)-2-(8-hydroxy-1,4-dioxaspiro[4.5]decan-8-yl)acetate (3.05 g, 7.10 mmol) was dissolved in pyridine (15 mL) under nitrogen. Phosphorus oxychloride (1.324 ml, 14.21 mmol) was added and the reaction warmed to 90° C. After an hour, the cooled reaction was poured onto ice. The mixture was extracted with ether. The organic layer was washed successively with 1 N hydrochloric acid, water, saturated sodium bicarbonate and brine. The crude product was obtained after drying over magnesium sulfate, filtration and evaporation. This material was applied to a 120 g Isco silica gel column and eluted with 0-25% ethyl acetate in hexanes. Evaporation provided ethyl 2-(2-bromo-6-methylphenoxy)-2-(1,4-dioxaspiro[4.5]dec-7-en-8-yl)acetate (1.17 g, 2.84 mmol, 40%). H NMR (400 MHz, CHLOROFORM-d) δ 7.36 (dd, J=7.9, 1.0 Hz, 1H), 7.08 (dd, J=7.5, 0.8 Hz, 1H), 6.86 (t, J=7.8 Hz, 1H), 5.72-5.61 (m, 1H), 4.93 (s, 1H), 4.27 (qd, J=7.1, 1.2 Hz, 2H), 4.02-3.92 (m, 4H), 2.73-2.58 (m, 1H), 2.30 (s, 6H), 1.85-1.76 (m, 2H), 1.29 (t, J=7.1 Hz, 3H).

29D. Ethyl (R)-7-methyl-2H-dispiro[benzofuran-3,1'-cyclohexane-4',2''-[1,3]dioxolane]-2-carboxylate Ethyl 2-(2-bromo-6-methylphenoxy)-2-(1,4-dioxaspiro[4.5]dec-7-en-8-yl)acetate (1.16 g, 2.82 mmol) was dissolved in toluene (50 mL). The solution was subjected to three cycles of vacuum/nitrogen purge. Tri-n-butyltin hydride (0.904 ml, 3.38 mmol) was added and the vacuum/nitrogen purge cycle was repeated. AIBN (0.116 g, 0.705 mmol). was added and the vacuum/nitrogen purge cycle was repeated again. The reaction was then warmed to 105° C. for an hour. The cooled reaction was evaporated. The residue was applied to an 80 g Isco silica gel column and eluted with 0-25% ethyl acetate in hexanes. Evaporation provided ethyl (R)-7-methyl-2H-dispiro[benzofuran-3,1'-cyclohexane-4',2''-[1,3]dioxolane]-2-carboxylate (956 mg, 2.88 mmol, 102% yield) as a colorless oil. A small amount of difficult to remove tin byproduct likely accounts for the high mass recovery. $^1$H NMR (400 MHz, CHLOROFORM-d) δ 7.06 (d, J=7.5 Hz, 1H), 6.99 (d, J=7.1 Hz, 1H), 6.84-6.76 (m, 1H), 4.90 (s, 1H), 4.30-4.17 (m, 2H), 3.98 (s, 4H), 2.25 (s, 3H), 2.04-1.72 (m, 8H), 1.29 (t, J=7.2 Hz, 3H). $^{13}$C NMR (101 MHz, CHLOROFORM-d) δ 169.9, 156.9, 132.9, 129.9, 121.0, 120.7, 120.2, 108.0, 87.6, 64.4 (d, J=3.7 Hz, IC), 61.1, 49.0, 35.5, 31.6, 31.4, 29.6, 15.1, 14.2.

29E. (R)-(7-methyl-2H-dispiro[benzofuran-3,1'-cyclohexane-4',2''-[1,3]dioxolan]-2-yl)methanol Ethyl (R)-7-methyl-2H-dispiro[benzofuran-3,1'-cyclohexane-4',2''-[1,3]dioxolane]-2-carboxylate (956 mg, 2.88 mmol) was dissolved in dry THF (10 mL) under nitrogen. The reaction was cooled in an ice bath and a pellet of LAH (575 mg, 15.15 mmol) was added. After an hour, the reaction was worked up using the Fieser procedure (L. F. Fieser and M. Fieser, *Reagents for Organic Synthesis*, Vol. 1, p. 584

(1967)). After filtration and evaporation, the residue was azeotroped with ethanol and pumped down to give (R)-(7-methyl-2H-dispiro[benzofuran-3,1'-cyclohexane-4',2"-[1,3] dioxolan]-2-yl)methanol (762 mg, 2.62 mmol, 91% yield) as a viscous colorless oil. $^1$H NMR (400 MHz, DMSO-$d_6$) δ 7.01 (d, J=7.3 Hz, 1H), 6.93 (d, J=7.3 Hz, 1H), 6.76-6.69 (m, 1H), 4.79 (br s, 1H), 4.42 (dd, J=6.7, 4.4 Hz, 1H), 3.90 (s, 4H), 3.69-3.60 (m, 1H), 3.60-3.51 (m, 1H), 2.14 (s, 3H), 1.91-1.56 (m, 8H). 29F. (R)-2-(Hydroxymethyl)-7-methyl-2H-spiro[benzofuran-3,1'-cyclohexan]-4'-one (R)-(7-methyl-2H-dispiro[benzofuran-3,1'-cyclohexane-4',2"-[1,3] dioxolan]-2-yl)methanol (762 mg, 2.62 mmol) was dissolved in THF-acetic acid-water (3:2:2, 14 mL) under nitrogen. The reaction was warmed to 55° C. After two days, the cooled reaction was diluted with water and quenched carefully with saturated sodium bicarbonate solution. The mixture was extracted with ether. The organic phase was washed with water and then brine. Drying over magnesium sulfate, filtration and evaporation provided the crude product. This material was partially purified on an Isco silica gel column (ethyl acetate-hexanes gradient). The material obtained from the chromatography was further purified by crystallization from a small volume of hot ethyl acetate. Filtration and rinsing with 3:1 hexanes-ethyl acetate to gave (R)-2-(hydroxymethyl)-7-methyl-2H-spiro[benzofuran-3, 1'-cyclohexan]-4'-one (314 mg, 1.275 mmol, 48.6% yield) as a colorless solid. $^1$H NMR (500 MHz, CHLOROFORM-d) δ 7.03 (t, J=6.9 Hz, 2H), 6.91-6.78 (m, 1H), 4.67 (dd, J=6.9, 4.9 Hz, 1H), 3.89 (br d, J=6.7 Hz, 2H), 2.67-2.53 (m, 3H), 2.50-2.40 (m, 1H), 2.25 (s, 3H), 2.21-2.09 (m, 3H), 2.09-1.96 (m, 2H). $^{13}$C NMR (126 MHz, CHLOROFORM-d) δ 210.3, 156.0, 133.2, 130.3, 121.1, 120.7, 120.7, 89.5, 61.9, 46.2, 38.4, 38.1, 37.5, 30.1, 15.2.

29G. rac-(E)-Ethyl 2-((1'R,2S)-2-(hydroxymethyl)-7-methyl-2H-spiro[benzofuran-3,1'-cyclohexan]-4'-ylidene)acetate A two neck flask was charged with sodium hydride (40.6 mg, 1.015 mmol) under nitrogen. THF (2 mL) was added and the reaction cooled in an ice bath. Triethyl phosphonoacetate (201 µl, 1.015 mmol) was added dropwise and stirring continued for 10 minutes. The reaction bubbled vigorously and a clear solution was obtained. (R)-2-(hydroxymethyl)-7-methyl-2H-spiro[benzofuran-3,1'-cyclohexan]-4'-one (50 mg, 0.203 mmol) was dissolved in THF (1 mL) and added dropwise. After a few minutes, the cooling bath was removed. Upon completion the reaction was quenched with saturated ammonium chloride. After transfer to a separatory funnel, the reaction was extracted twice with ethyl acetate. The combined organic layers were washed with brine. After drying over magnesium sulfate, filtration and evaporation, the crude product was applied to a 24 g Isco silica gel column and eluted with 0-100% ethyl acetate in hexanes. Evaporation of the appropriate fractions gave rac-(E)-ethyl 2-((1'R,2S)-2-(hydroxymethyl)-7-methyl-2H-spiro[benzofuran-3,1'-cyclohexan]-4'-ylidene)acetate (34 mg, 0.107 mmol, 52.9% yield). $^1$H NMR (400 MHz, CHLOROFORM-d) δ 7.07-6.98 (m, 2H), 6.83 (t, J=7.4 Hz, 1H), 5.75 (s, 1H), 4.69-4.61 (m, 1H), 4.19 (qd, J=7.1, 2.4 Hz, 2H), 3.89-3.71 (m, 2H), 3.56-3.35 (m, 1H), 2.55-2.43 (m, 1H), 2.55-2.43 (m, 1H), 2.35-2.26 (m, 1H), 2.26 (s, 3H), 2.17-2.08 (m, 1H), 2.00-1.84 (m, 3H), 1.81-1.66 (m, 1H), 1.31 (td, J=7.1, 2.3 Hz, 3H).

29H. rac-Ethyl 2-((1'r,2R,4'R)-2-(hydroxymethyl)-7-methyl-2H-spiro[benzofuran-3,1'-cyclohexan]-4'-yl)acetate and 29. rac-Ethyl 2-((1's,2R,4'S)-2-(hydroxymethyl)-7-methyl-2H-spiro[benzofuran-3,1'-cyclohexan]-4'-yl)acetate A Parr bottle was charged with rac-(E)-ethyl 2-((1'R,2S)-2-(hydroxymethyl)-7-methyl-2H-spiro[benzofuran-3,1'-cyclohexan]-4'-ylidene)acetate (34 mg, 0.107 mmol) in ethyl acetate (ca. 5 mL). 5% Rh/C (34 mg) was added and the bottle was pressurized to 45 psi hydrogen. After three hours, the reaction was filtered and evaporated. The crude product was applied to a 0.5 mm silica gel prep plate and developed three times with 1:1 ether/hexanes. Extraction of the slow band gave rac-ethyl 2-((1'r,2R,4'R)-2-(hydroxymethyl)-7-methyl-2H-spiro[benzofuran-3,1'-cyclohexan]-4'-yl)acetate (10.8 mg, 0.034 mmol, 32%) while the fast band provided rac-ethyl 2-(('s,2R,4'S)-2-(hydroxymethyl)-7-methyl-2H-spiro[benzofuran-3,1'-cyclohexan]-4'-yl)acetate (4.2 mg, 0.013 mmol, 12%).

29H. $^1$H NMR (500 MHz, CHLOROFORM-d) δ 7.25 (d, J=7.0 Hz, 1H), 7.01 (d, J=7.2 Hz, 1H), 6.81 (t, J=7.5 Hz, 1H), 4.34 (dd, J=8.1, 3.5 Hz, 1H), 4.17 (q, J=7.2 Hz, 2H), 3.86 (qdd, J=12.0, 8.3, 3.4 Hz, 2H), 2.37 (d, J=7.0 Hz, 2H), 2.25 (s, 3H), 1.96 (br dd, J=7.9, 3.8 Hz, 1H), 1.90 (ddd, J=9.3, 4.0, 2.0 Hz, 1H), 1.82-1.75 (m, 2H), 1.73-1.67 (m, 1H), 1.66-1.64 (m, 1H), 1.59-1.53 (m, 2H), 1.30 (t, J=7.1 Hz, 4H). $^{13}$C NMR (126 MHz, CHLOROFORM-d) δ 172.8, 156.6, 134.6, 129.5, 122.9, 120.3, 120.3, 91.9, 61.7, 60.3, 46.2, 41.2, 36.2, 33.8, 29.9, 28.3, 27.7, 15.2, 14.3.

29I. $^1$H NMR (500 MHz, CHLOROFORM-d) δ 7.01-6.96 (m, 1H), 6.91-6.87 (m, 1H), 6.86-6.81 (m, 1H), 4.68 (dd, J=9.3, 2.9 Hz, 1H), 4.17 (q, J=7.2 Hz, 2H), 3.82-3.73 (m, 1H), 3.70-3.60 (m, 1H), 2.27 (d, J=7.0 Hz, 2H), 2.25 (s, 3H), 2.05 (dd, J=10.1, 2.6 Hz, 1H), 1.99-1.75 (m, 6H), 1.43 (td, J=13.5, 3.4 Hz, 1H), 1.30 (t, J=7.2 Hz, 4H), 1.14-1.00 (m, 1H). $^{13}$C NMR (126 MHz, CHLOROFORM-d) δ 172.7, 155.3, 135.3, 129.7, 121.0, 120.3, 119.8, 88.9, 61.9, 60.3, 46.8, 41.7, 38.4, 34.0, 30.7, 29.4, 29.3, 15.1, 14.3.

Example 29 rac-ethyl 2-((1'r,2R,4'R)-2-(hydroxymethyl)-7-methyl-2H-spiro[benzofuran-3,1'-cyclohexan]-4'-yl)acetate (10.8 mg, 0.034 mmol) was dissolved in a mixture of THF (300 µL) and water (100 µL). A solution of 1 N lithium hydroxide (100 µL) was introduced.

Methanol was then added until the reaction became until homogeneous. The vessel was flushed with nitrogen and warmed to 55° C. for 4 hours. The cooled reaction was quenched with 1 N hydrochloric acid (100 µL). The reaction was concentrated under a stream of nitrogen. The residue was transferred to a separatory funnel and partitioned between water and methylene chloride. The organic phase was washed with brine. Drying over magnesium sulfate, filtration and evaporation provided the crude product which was used directly in the next transformation. This material was dissolved in DMF (0.5 mL) under nitrogen. 4-Chloroaniline (6.46 mg, 0.051 mmol) and triethylamine (14.11 µl, 0.101 mmol) were added. The reaction was initiated with the addition of BOP (22.39 mg, 0.051 mmol). After stirring overnight, the reaction was diluted with DMF (1 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-75% B over 20 minutes, then a 3-minute hold at 100% B; Flow: 20 mL/min. Fractions containing the desired product were combined and dried via centrifugal evaporation to give rac-N-(4-chlorophenyl)-2-((1'r,2R,4'R)-2-(hydroxymethyl)-7-methyl-2H-spiro[benzofuran-3,1'-cyclohexan]-4'-yl)acetamide (4.3 mg, 10.8 μmol, 32%). $^1$H NMR (500 MHz, DMSO-$d_6$) δ 10.10 (s, 1H), 7.61 (br d, J=8.7 Hz, 2H), 7.34 (br d, J=8.7 Hz, 2H), 7.27 (br d, J=7.4 Hz, 1H), 6.95 (d, J=7.5 Hz, 1H), 6.73 (t, J=7.4 Hz, 1H), 4.16-4.04 (m, 1H), 3.62-3.50 (m, 2H), 3.17 (s, 1H), 2.33 (br d, J=7.0 Hz, 2H), 2.12 (s, 3H), 1.87 (br s, 1H), 1.76-1.59 (m, 4H), 1.60-1.44 (m, 3H), 1.44-1.33 (m, 1H). LC-MS Anal. Calc'd for $C_{23}H_{26}ClNO_3$ 399.16, found [M+H] 400.0, $T_r$=1.95 min (Method A).

Example 30 rac-N-(4-Chlorophenyl)-2-((1's,2R,4'S)-2-(hydroxymethyl)-7-methyl-2H-spiro[benzofuran-3,1'-cyclohexan]-4'-yl)acetamide

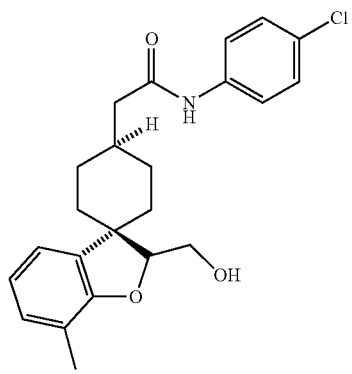

rac-Ethyl 2-((1's,2R,4'S)-2-(hydroxymethyl)-7-methyl-2H-spiro[benzofuran-3,1'-cyclohexan]-4'-yl)acetate (4.2 mg, 0.013 mmol) (Intermediate 291) was dissolved in THF (0.3 mL) and water (0.1 mL). A solution of 1 M sodium hydroxide (0.1 mL) was introduced. Finally, methanol was added dropwise until the reaction became homogeneous. The vessel was flushed with nitrogen, sealed and heated to 50° C. overnight. The cooled reaction was quenched with 1 N hydrochloric acid (0.1 mL). The reaction was partitioned between methylene chloride and water. The organic phase was washed with brine. Drying over magnesium sulfate, filtration and evaporation gave the crude product which was used directly in the amide forming reaction. This material was dissolved in DMF (0.5 mL). 4-Chloroaniline (2.504 mg, 0.020 mmol) and triethylamine (5.47 μl, 0.039 mmol) were then added. The reaction was initiated with the addition of BOP (8.68 mg, 0.020 mmol). After stirring overnight, the reaction was diluted with methanol and purified by RP-HPLC (methanol-water gradient+0.1% TFA). The product containing fraction was concentrated under a stream of nitrogen and then pumped down to give rac-N-(4-chlorophenyl)-2-((1's,2R,4'S)-2-(hydroxymethyl)-7-methyl-2H-spiro[benzofuran-3,1'-cyclohexan]-4'-yl)acetamide (1.1 mg, 2.7 μmol). $^1$H NMR (500 MHz, CHLOROFORM-d) δ 7.50-7.44 (m, 2H), 7.30 (d, J=8.7 Hz, 2H), 7.15 (br s, 1H), 6.97 (dd, J=7.2, 0.7 Hz, 1H), 6.90-6.85 (m, 1H), 6.84-6.79 (m, 1H), 4.68 (dd, J=9.4, 2.8 Hz, 1H), 3.77 (dd, J=11.7, 2.9 Hz, 1H), 3.66 (dd, J=11.7, 9.5 Hz, 1H), 2.30 (dd, J=7.0, 1.7 Hz, 2H), 2.22 (s, 3H), 2.11-1.99 (m, 1H), 1.94 (br d, J=13.3 Hz, 1H), 1.90-1.77 (m, 4H), 1.50-1.38 (m, 1H), 1.36-1.24 (m, 1H), 1.09 (qd, J=12.4, 4.7 Hz, 1H). LC-MS Anal. Calc'd for $C_{23}H_{26}ClNO_3$ 399.16, found [M+H] 400.1, $T_r$=1.01 min (Method C).

EVALUATION OF BIOLOGICAL ACTIVITY

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 μL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 μl sample with an equal volume of 100 mmol/L potassium phosphate buffer, pH 6.5, containing 40 mmol/L ascorbic acid (neutralized to pH 7.0), 100 μmol/L methylene blue, 200 μg/mL catalase, and 400 μmol/l L-Trp for 30 min at 37° C. The assay can be terminated by the addition of 16 μL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses. Groups of 1,000-1,200 islets incubated for 24 h in Miami medium in the presence of cytokines can be harvested and sonicated in PBS as above, and 50 µg protein samples can be electrophoresed on 10% SDS-PAGE gels. COS7 cells ($0.6 \times 10^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-STAT$_{1\alpha}$ p91, and STAT$_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO. Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1×81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif,* 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 µM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 µg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 µM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 µL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 µL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% CO2.

The compound treatments were stopped by adding trichloroacetic acid (Sigma-Aldrich) to a final concentration at 0.2%. The cell plate was further incubated at 50° C. for 30 minute. The equal volume supernatant (20 µL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Assessment of Inhibitor Activity in HeLa Cell-Based Indoleamine 2,3-dioxygenase (IDO) Assay:

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 µg/mL streptomycin (#SV30010, HyClone) and 10% fetal bovine serum (#SH30071.03 HyClone). Cells were maintained in a humidified incubator at 37° C. in 5% CO2.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 µL of culture medium. After a further 48 hour incubation, 170 µL of supernatant was transferred from each well to a fresh 96-well plate. 12.1 µL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 µL of the supernatant was transferred from each well to a fresh 96-well plate. 100 µl of 2% (w/v) p-dimethylaminobenzaldehyde (#15647-7, Sigma-Aldrich) in acetic acid (#A6283, Sigma-Aldrich) was added to each well mixed and incubated at room temperature for 20 inns. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Results of the IDO assays are shown in the table below.

| Ex. No. | IDO Hela $IC_{50}$ (µM) | IDO1 HEK Human $IC_{50}$ (µM) |
| --- | --- | --- |
| 1 | 0.114 | 0.1 |
| 2 | 0.189 | |
| 3 | 0.219 | 0.511 |
| 4 | 0.05 | |
| 5 | 0.092 | |
| 6 | 1.30 | |
| 7 | | 0.037 |
| 8 | | 0.024 |
| 9 | | 0.617 |
| 10 | | 0.980 |
| 11 | 0.045 | |
| 12 | 1.44 | |
| 13 | 0.628 | |
| 14 | | 0.005 |
| 15 | 0.02 | 0.017 |
| 16 | | 0.008 |
| 17 | | 0.059 |
| 18 | | 0.009 |
| 19 | | 0.914 |
| 20 | | 0.061 |
| 21 | | 0.059 |
| 22 | | 0.142 |
| 23 | | 0.254 |
| 24 | | 0.117 |
| 25 | | 0.794 |
| 26 | | 0.043 |
| 27 | | 0.093 |
| 28 | 0.201 | |
| 29 | | 0.068 |
| 30 | | 0.363 |

What is claimed:

1. A compound of formula I:

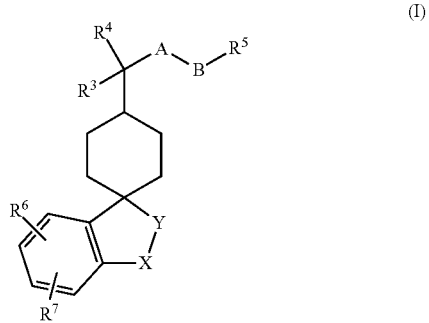

wherein:
-A-B— is a bond, —NH—CO— or —CO—NH—;
—X—Y— is —O—$CR^1R^2$— or —$CR^1R^2$—O—;
$R^1$ and $R^2$ are independently H or $C_1$-$C_6$ alkyl optionally substituted with one, two, or three substituents that are independently F, OH or CN;
$R^3$ and $R^4$ are independently H or $C_1$-$C_6$ alkyl optionally substituted with one, two, or three substituents that are independently F, OH or CN;
$R^5$ is $C_1$-$C_6$ alk-O—$C_1$-$C_6$ alkyl;
aryl optionally substituted with one, two, or three substituents that are independently selected from: halo, CN, $C_1$-$C_6$ alkyl, —O$C_1$-$C_6$ alkyl, and 5- to 6-membered heteroaryl optionally substituted with $C_1$-$C_6$ alkyl;
$C_3$-$C_{10}$ cycloalkyl optionally substituted with one, two, or three substituents independently selected from: halo, CN, $C_1$-$C_6$ alkyl, —O$C_1$-$C_6$ alkyl, and 5- to 6-membered heteroaryl optionally substituted with $C_1$-$C_6$ alkyl;

5- to 6-membered cycloheteroalkyl optionally substituted with one, two, or three substituents independently selected from: halo, CN, $C_1$-$C_6$ alkyl, —$OC_1$-$C_6$ alkyl, and 5- to 6-membered heteroaryl optionally substituted with $C_1$-$C_6$ alkyl; or 5- to 10-membered heteroaryl optionally substituted with one, two, or three substituents that are independently selected from: halo, CN, $C_1$-$C_6$ alkyl, —$OC_1$-$C_6$ alkyl, and 5- to 6-membered heteroaryl optionally substituted with $C_1$-$C_6$ alkyl; and $R^6$ and $R^7$ are independently H, halo, $C_1$-$C_6$ alkyl, —$OC_1$-$C_6$ alkyl, or $C_1$-$C_6$ haloalkyl;

or a pharmaceutically acceptable salt, a stereoisomer, or a tautomer thereof.

2. The compound according to claim 1, wherein:
$R^1$ and $R^2$ are independently H or $C_1$-$C_4$ alkyl optionally substituted with one OH;
$R^3$ and $R^4$ are independently H or $C_1$-$C_4$ alkyl;
$R^5$ is phenyl optionally substituted with one, two, or three substituents that are independently selected from: halo, CN, $C_1$-$C_6$ alkyl, and —$OC_1$-$C_6$ alkyl;
$C_6$-$C_{10}$ cycloalkyl optionally substituted with one, two, or three substituents independently selected from: halo, CN, $C_1$-$C_6$ alkyl, and —$OC_1$-$C_6$ alkyl; or
5- to 10-membered heteroaryl optionally substituted with one, two, or three substituents that are independently selected from: halo, CN, $C_1$-$C_6$ alkyl, and —$OC_1$-$C_6$ alkyl; and
$R^6$ and $R^7$ are independently H, F, Cl, $CH_3$, $CF_3$, or $OCH_3$.

3. The compound according to claim 1, wherein:
$R^5$ is selected from: phenyl, cyclohexyl, bicyclo[2.2.2]octanyl, adamantanyl, and 9- to 10 membered heteroaryl; wherein each moiety is optionally substituted with one or two substituents that are independently selected from: halo, CN, $C_1$-$C_4$ alkyl, and —$OC_1$-$C_4$ alkyl.

4. The compound according to claim 1, wherein:
—X—Y— is —O—$CH_2$—, —O—CH($CH_2OH$)—, or —$CH_2$—O—;
$R^3$ is H or $CH_3$;
$R^4$ is H;
$R^5$ is selected from:

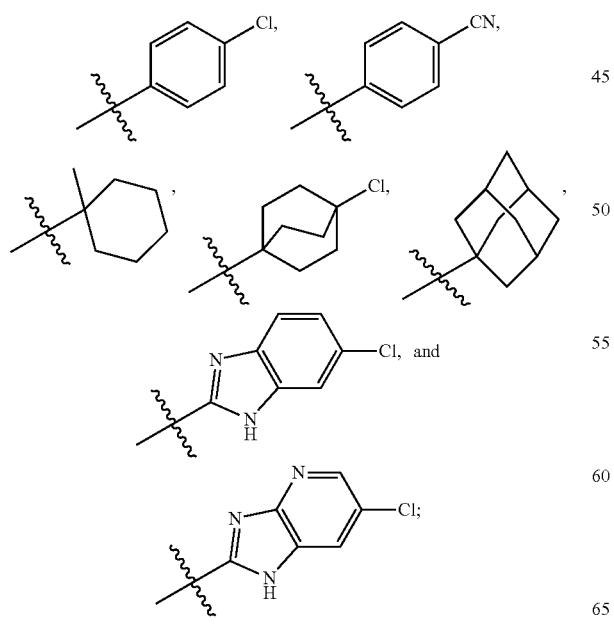

$R^6$ is H or $CH_3$; and
$R^7$ is H.

5. The compound according to claim 1, wherein -A-B— is a bond.

6. The compound according to claim 1, wherein -A-B— is —NH—CO—.

7. The compound according to claim 1, wherein -A-B— is —CO—NH—.

8. The compound according to claim 1, wherein the compound is selected from:

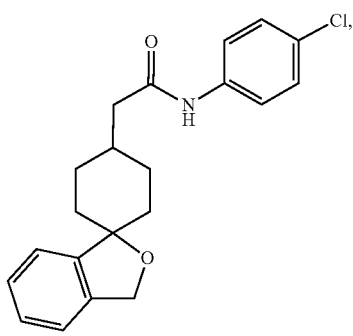

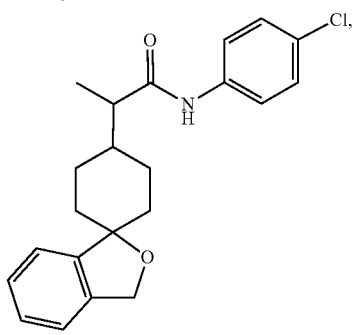

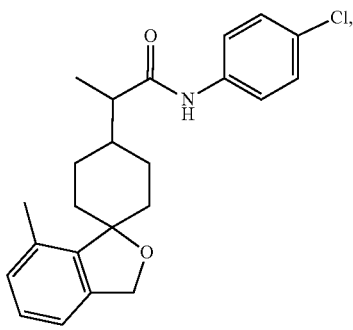

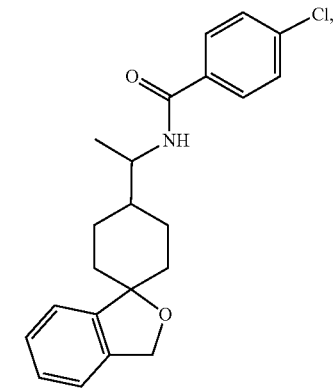

81
-continued
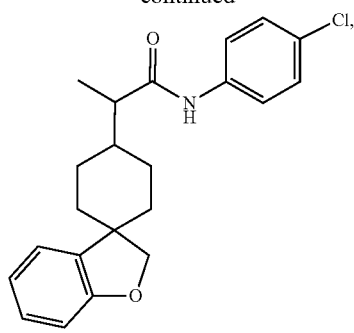
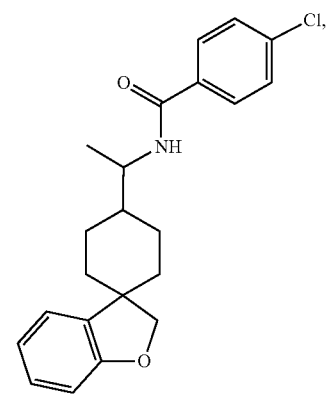
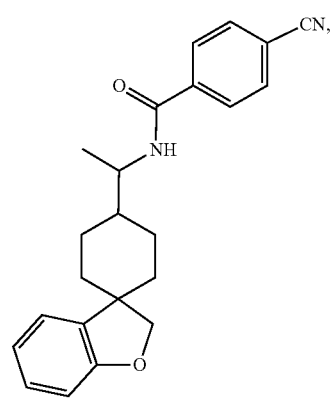
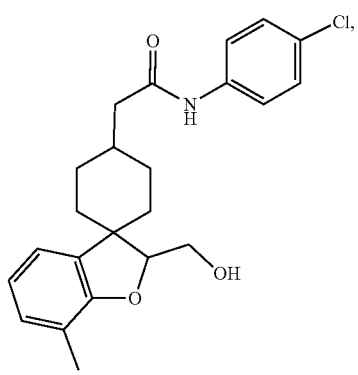
82
-continued
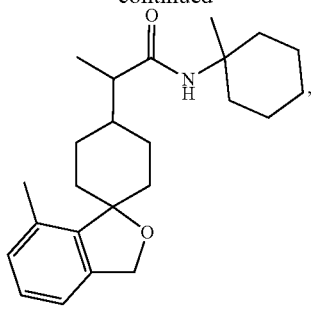
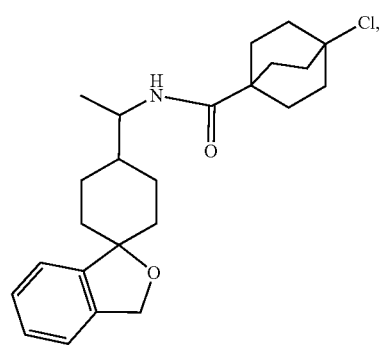
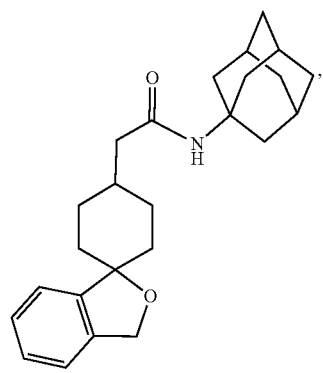
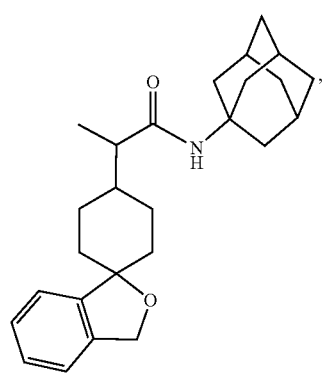

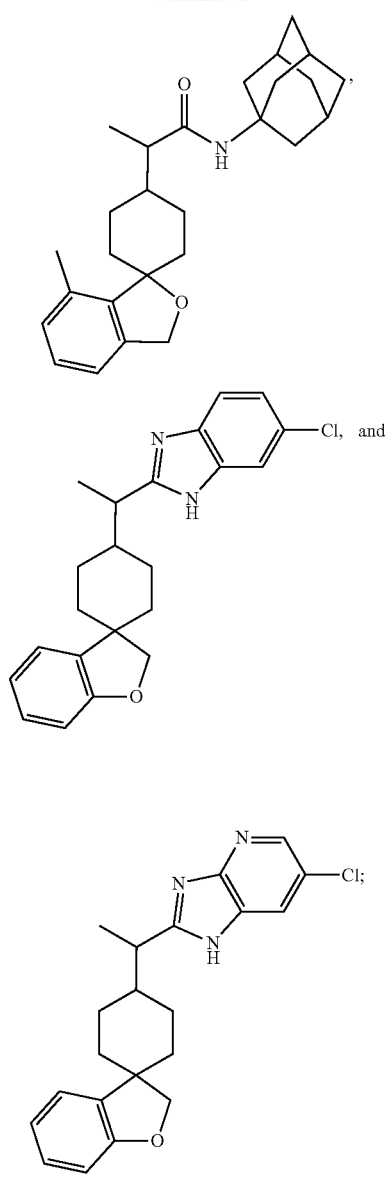
or a pharmaceutically acceptable salt, a stereoisomer, or a tautomer thereof.
9. The compound according to claim 1, wherein the compound is selected from:

85
-continued
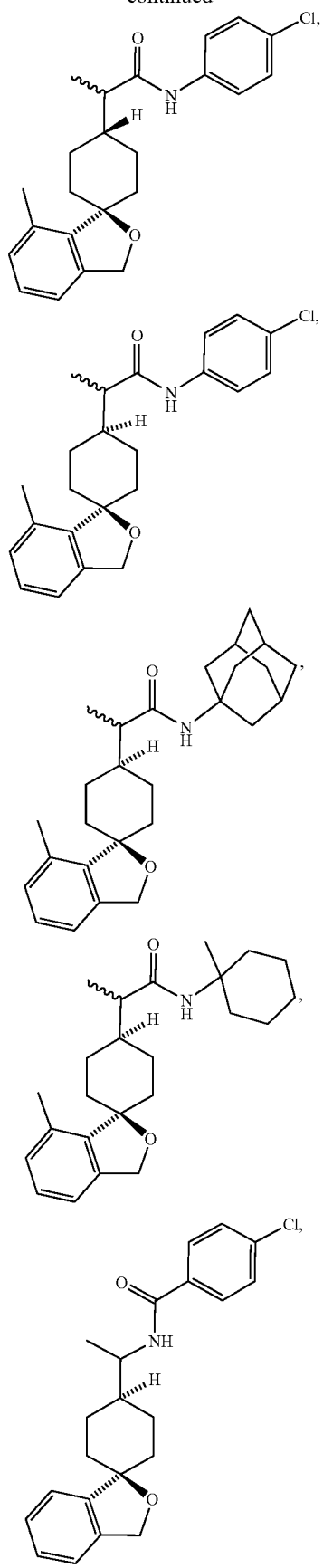
86
-continued
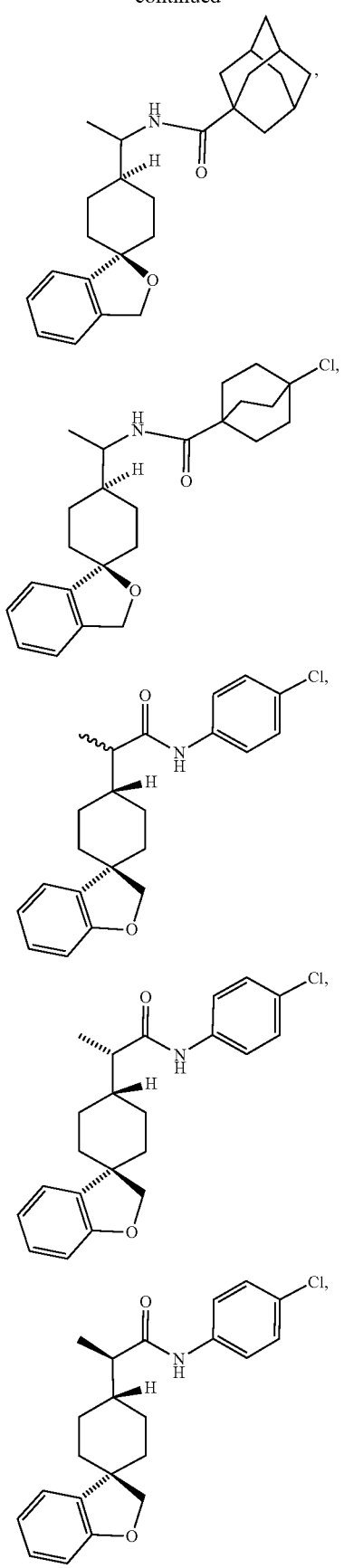

87
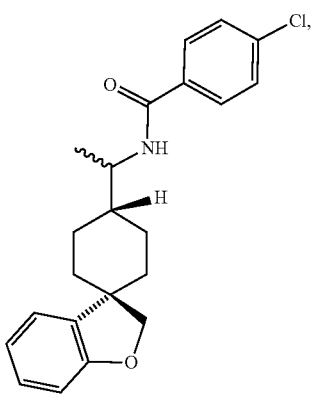
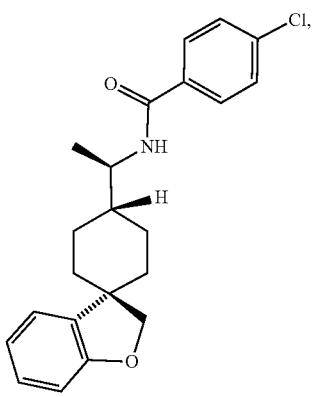
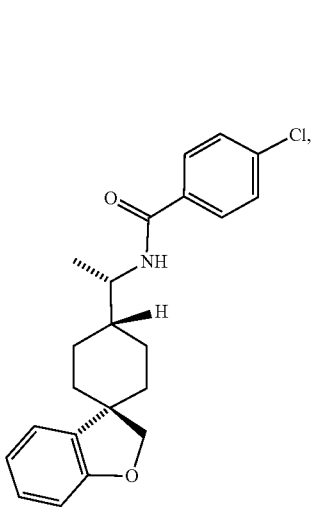
88
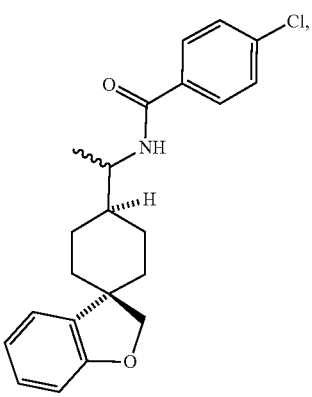
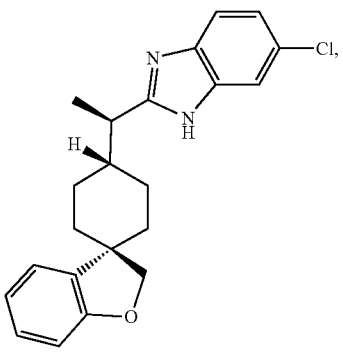
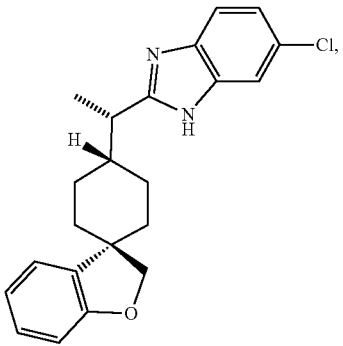
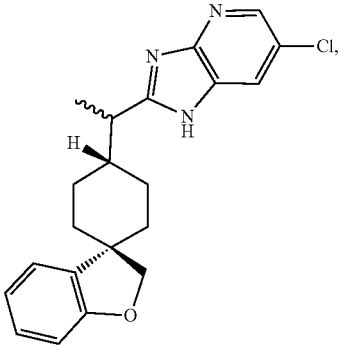

89
-continued

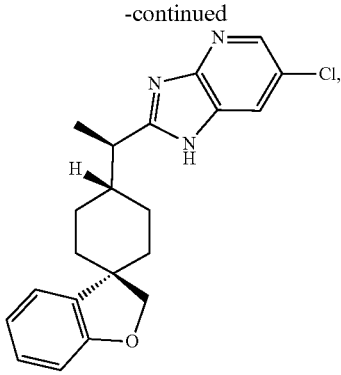

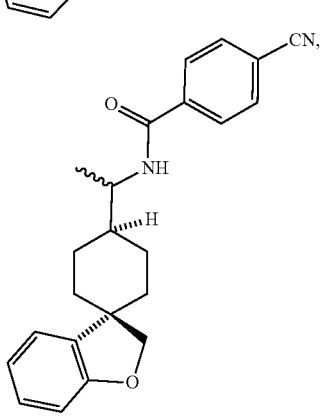

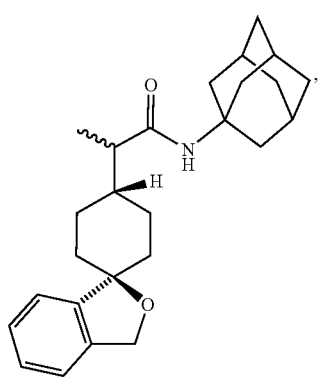

90
-continued

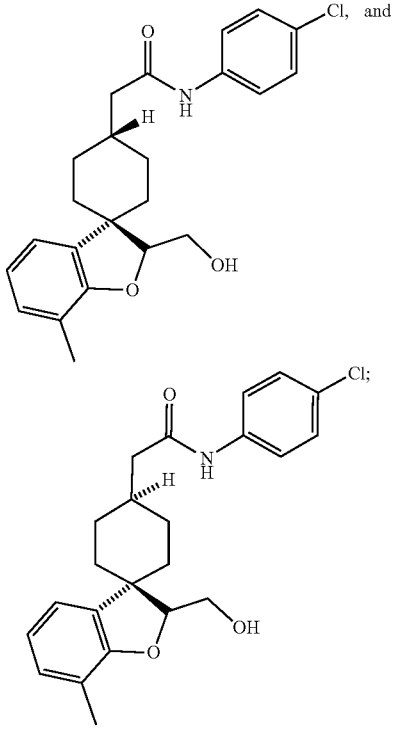

or a pharmaceutically acceptable salt thereof.

10. A pharmaceutical composition comprising a compound according to claim 1 and a pharmaceutically acceptable excipient.

11. The pharmaceutical composition of claim 10, further comprising ipilimumab, nivolumab, or pembrolizumab, or a combination thereof.

12. A method of treating cancer in a patient in need of such treatment comprising administering to the patient a therapeutically effective amount of a compound according to claim 1; wherein the cancer is bladder cancer, ovarian cancer, breast cancer, pancreatic cancer, prostate cancer, colon cancer, blood cancer or lung cancer.

13. The method of claim 12, wherein the cancer is bladder cancer.

14. The method of claim 12, wherein the cancer is ovarian cancer.

15. The method of claim 12, wherein the cancer is breast cancer.

16. The method of claim 12, wherein the cancer is pancreatic cancer.

17. The method of claim 12, wherein the cancer is prostate cancer.

18. The method of claim 12, wherein the cancer is colon cancer.

19. The method of claim 12, wherein the cancer is blood cancer.

20. The method of claim 12, wherein the cancer is lung cancer.

* * * * *